(12) United States Patent
Matray et al.

(10) Patent No.: US 12,145,956 B2
(45) Date of Patent: *Nov. 19, 2024

(54) PROGRAMMABLE POLYMERIC DRUGS

(71) Applicant: SONY GROUP CORPORATION, Tokyo (JP)

(72) Inventors: Tracy Matray, Snohomish, WA (US); Sharat Singh, Rancho Santa Fe, CA (US); C. Frederick Battrell, Wenatchee, WA (US); Michael Vanbrunt, Covington, WA (US)

(73) Assignee: SONY GROUP CORPORATION, Tokyo (JP)

( * ) Notice: Subject to any disclaimer, the term of this patent is extended or adjusted under 35 U.S.C. 154(b) by 910 days.

This patent is subject to a terminal disclaimer.

(21) Appl. No.: 16/639,496

(22) PCT Filed: Oct. 5, 2018

(86) PCT No.: PCT/US2018/054725
§ 371 (c)(1),
(2) Date: Feb. 14, 2020

(87) PCT Pub. No.: WO2019/071208
PCT Pub. Date: Apr. 11, 2019

(65) Prior Publication Data
US 2021/0032277 A1   Feb. 4, 2021

Related U.S. Application Data

(60) Provisional application No. 62/568,706, filed on Oct. 5, 2017.

(51) Int. Cl.
*C07F 9/24*    (2006.01)
*A61K 47/58*   (2017.01)
*A61K 47/68*   (2017.01)
*A61K 49/00*   (2006.01)

(52) U.S. Cl.
CPC .......... *C07F 9/2408* (2013.01); *A61K 47/605* (2017.08); *A61K 47/6809* (2017.08); *A61K 47/6849* (2017.08); *A61K 47/6851* (2017.08); *A61K 47/6883* (2017.08); *A61K 49/0043* (2013.01); *A61K 49/0054* (2013.01)

(58) Field of Classification Search
CPC .................................................. A61K 47/605
See application file for complete search history.

(56) References Cited

U.S. PATENT DOCUMENTS

| | | | |
|---|---|---|---|
| 4,450,305 A | 5/1984 | Kamhi |
| 4,476,229 A | 10/1984 | Fino et al. |
| 4,778,753 A | 10/1988 | Yamanishi et al. |
| 5,053,054 A | 10/1991 | Kirchanski |
| 5,268,486 A | 12/1993 | Waggoner et al. |
| 5,318,894 A | 6/1994 | Pugia |
| 5,582,977 A | 12/1996 | Yue et al. |
| 5,698,391 A | 12/1997 | Cook et al. |
| 5,886,177 A | 3/1999 | Cook et al. |
| 5,994,143 A | 11/1999 | Bieniarz et al. |
| 6,005,093 A | 12/1999 | Wood et al. |
| 6,140,480 A | 10/2000 | Kool |
| 6,171,859 B1 | 1/2001 | Herrnstadt et al. |
| 6,218,108 B1 | 4/2001 | Kool |
| 6,365,730 B1 | 4/2002 | Jennings et al. |
| 6,380,431 B1 | 4/2002 | Whipple et al. |
| 6,479,650 B1 | 11/2002 | Kool |
| 6,514,700 B1 | 2/2003 | Singh |
| 6,534,041 B1 | 3/2003 | Licha et al. |
| 6,627,400 B1 | 9/2003 | Singh et al. |
| 6,670,193 B2 | 12/2003 | Kool |
| 6,716,452 B1 | 4/2004 | Piccariello et al. |
| 6,852,709 B2 | 2/2005 | Leong et al. |
| 7,038,063 B2 | 5/2006 | Lee et al. |
| 7,060,708 B2 | 6/2006 | Piccariello et al. |
| 7,172,907 B2 | 2/2007 | Chen et al. |
| 7,423,133 B2 | 9/2008 | Kool et al. |
| 7,667,024 B2 | 2/2010 | Mao et al. |
| 7,897,684 B2 | 3/2011 | Bazan et al. |
| 8,008,522 B2 | 8/2011 | Lukhtanov et al. |
| 8,101,776 B2 | 1/2012 | Berens et al. |
| 8,153,706 B2 | 4/2012 | Vasudevan |
| 8,217,389 B2 | 7/2012 | Nakano et al. |
| 8,293,700 B2 | 10/2012 | Arranz |
| 8,349,308 B2 | 1/2013 | Yurkovetskiy et al. |

(Continued)

FOREIGN PATENT DOCUMENTS

| CA | 2263671 A1 | 2/1998 |
|---|---|---|
| CN | 102174078 A | 9/2011 |

(Continued)

OTHER PUBLICATIONS

Irani et al, Molecular Immunology, 2015, vol. 67, pp. 171-182 (Year: 2015).*
Shuman and Glickman, Nature Review Microbiology, 2007, vol. 5, pp. 852-861 (Year: 2007).*
Pelegrin et al, Trends in Microbiology, 2015, vol. 23, pp. 653-665 (Year: 2015).*
Dropulic and Cohen, Clinical Pharmacology & Therapeutics, 2010, vol. 88, pp. 610-619 (Year: 2010).*
McKinlay et al (Journal of the American Chemical Society, 2016, vol. 138, pp. 3510-3517) (Year: 2016).*

(Continued)

*Primary Examiner* — Karen A. Canella
(74) *Attorney, Agent, or Firm* — Seed IP Law Group LLP

(57) ABSTRACT

Compounds useful as biologically active compounds are disclosed. The compounds have the following structure (I): or a stereoisomer, tautomer or salt thereof, wherein $R^1$, $R^2$, $R^3$, L, $L^1$, $L^2$, $L^3$, M and n are as defined herein. Methods associated with preparation and use of such compounds is also provided.

20 Claims, 5 Drawing Sheets

(56) References Cited

U.S. PATENT DOCUMENTS

| | | |
|---|---|---|
| 8,354,515 B2 | 1/2013 | Ueno et al. |
| 8,431,545 B2 | 4/2013 | Kataoka et al. |
| 8,491,993 B2 | 7/2013 | Nguyen et al. |
| 8,546,590 B2 | 10/2013 | Gall |
| 8,632,947 B2 | 1/2014 | Bentley et al. |
| 8,802,738 B2 | 8/2014 | Emrick |
| 8,895,023 B2 | 11/2014 | Rademacher et al. |
| 8,906,603 B2 | 12/2014 | Castro et al. |
| 8,946,394 B2 | 2/2015 | Na et al. |
| 9,029,537 B2 | 5/2015 | Koch |
| 9,085,799 B2 | 7/2015 | Bazan et al. |
| 9,150,782 B2 | 10/2015 | Lee et al. |
| 9,400,273 B1 | 7/2016 | Liu et al. |
| 9,545,447 B2 | 1/2017 | Wooley et al. |
| 9,649,389 B2 | 5/2017 | Groves et al. |
| 9,687,291 B2 | 6/2017 | Shimizu et al. |
| 9,689,877 B2 | 6/2017 | Matray et al. |
| 9,696,310 B2 | 7/2017 | Margulies et al. |
| 9,714,946 B2 | 7/2017 | Bradner et al. |
| 9,765,220 B2 | 9/2017 | Matray et al. |
| 9,822,134 B2 | 11/2017 | Segev |
| 9,851,359 B2 | 12/2017 | Matray et al. |
| 9,884,070 B2 | 2/2018 | Denardo et al. |
| 9,910,051 B2 | 3/2018 | Beacham et al. |
| 9,913,992 B2 | 3/2018 | Demarest et al. |
| 9,932,578 B2 | 4/2018 | Feinstein et al. |
| 9,939,454 B2 | 4/2018 | Dzubay et al. |
| 10,036,754 B2 | 7/2018 | Matray et al. |
| 10,191,060 B2 | 1/2019 | Chiu et al. |
| 10,435,563 B2 | 10/2019 | Matray et al. |
| 10,617,670 B2 | 4/2020 | Sapra et al. |
| 10,709,791 B2 | 7/2020 | Stayton et al. |
| 10,834,091 B2 | 11/2020 | Deninno et al. |
| 10,865,310 B2 | 12/2020 | Matray et al. |
| 10,866,244 B2 | 12/2020 | Matray et al. |
| 10,954,391 B2 | 3/2021 | Matray et al. |
| 10,989,715 B2 | 4/2021 | Matray et al. |
| 11,013,756 B2 | 5/2021 | Haruta et al. |
| 11,084,932 B2 | 8/2021 | Battrell et al. |
| 11,142,647 B2 | 10/2021 | Matray et al. |
| 11,312,736 B1 | 4/2022 | Matray et al. |
| 11,352,502 B2 | 6/2022 | Matray et al. |
| 11,370,922 B2 | 6/2022 | Matray et al. |
| 11,377,563 B2 | 7/2022 | Matray et al. |
| 11,390,754 B2 | 7/2022 | Singh et al. |
| 11,434,374 B2 | 9/2022 | Matray et al. |
| 11,434,377 B2 | 9/2022 | Matray et al. |
| 11,453,783 B2 | 9/2022 | Matray et al. |
| 11,618,906 B2 | 4/2023 | Steele |
| 11,685,835 B2 | 6/2023 | Matray |
| 11,874,280 B2 | 1/2024 | Jackson et al. |
| 2001/0018503 A1 | 8/2001 | Whipple et al. |
| 2002/0012947 A1 | 1/2002 | Bevers et al. |
| 2002/0099013 A1 | 7/2002 | Piccariello et al. |
| 2002/0142329 A1 | 10/2002 | Matray et al. |
| 2003/0054361 A1 | 3/2003 | Heller |
| 2003/0207208 A1 | 11/2003 | Uenishi |
| 2003/0207264 A1 | 11/2003 | Packard et al. |
| 2004/0014981 A1 | 1/2004 | Lugade et al. |
| 2004/0067498 A1 | 4/2004 | Chenna et al. |
| 2004/0096825 A1 | 5/2004 | Chenna et al. |
| 2004/0138467 A1 | 7/2004 | French et al. |
| 2004/0186278 A1 | 9/2004 | Chen et al. |
| 2004/0224372 A1 | 11/2004 | Li et al. |
| 2004/0241768 A1 | 12/2004 | Whitten et al. |
| 2005/0054024 A1 | 3/2005 | Lawrence |
| 2005/0123935 A1 | 6/2005 | Haugland et al. |
| 2006/0008822 A1 | 1/2006 | Manoharan et al. |
| 2006/0035302 A1 | 2/2006 | Lee |
| 2006/0063186 A1 | 3/2006 | Benson et al. |
| 2007/0042398 A1 | 2/2007 | Peng et al. |
| 2007/0077549 A1 | 4/2007 | Buller et al. |
| 2007/0148094 A1 | 6/2007 | Uzgiris |
| 2007/0269902 A1 | 11/2007 | Beechem et al. |
| 2008/0227939 A1 | 9/2008 | Mizoshita et al. |
| 2009/0253792 A1 | 10/2009 | Mickle et al. |
| 2009/0299070 A1 | 12/2009 | Berens et al. |
| 2010/0039684 A1 | 2/2010 | Kolb et al. |
| 2010/0092386 A1 | 4/2010 | Segev |
| 2010/0129800 A1 | 5/2010 | Aymami Bofarull et al. |
| 2010/0192312 A1 | 8/2010 | Cremer et al. |
| 2011/0144065 A1 | 6/2011 | Denardo et al. |
| 2011/0224516 A1 | 9/2011 | Romey et al. |
| 2012/0021454 A1 | 1/2012 | Bikker et al. |
| 2012/0116079 A1 | 5/2012 | Lukhtanov et al. |
| 2012/0126175 A1 | 5/2012 | Ueno et al. |
| 2013/0059343 A1 | 3/2013 | Cheung |
| 2013/0102021 A1 | 4/2013 | Beacham et al. |
| 2013/0119363 A1 | 5/2013 | Sasaki et al. |
| 2013/0137755 A1 | 5/2013 | Segev |
| 2013/0202536 A1 | 8/2013 | Mustaev et al. |
| 2013/0244891 A1 | 9/2013 | Waggoner et al. |
| 2014/0023590 A1 | 1/2014 | Gao et al. |
| 2014/0193504 A1 | 7/2014 | Wooley et al. |
| 2014/0275508 A1 | 9/2014 | Scarr et al. |
| 2015/0030541 A1 | 1/2015 | Rogers |
| 2015/0110715 A1 | 4/2015 | Eder et al. |
| 2015/0159198 A1 | 6/2015 | McGall et al. |
| 2015/0232615 A1 | 8/2015 | Kwiatkowski |
| 2015/0258217 A1 | 9/2015 | Caravan |
| 2016/0039850 A1 | 2/2016 | Segev |
| 2016/0176903 A1 | 6/2016 | Segev |
| 2016/0264737 A1 | 9/2016 | Bartholomew et al. |
| 2016/0327859 A1 | 11/2016 | Idei et al. |
| 2016/0347907 A1 | 12/2016 | Dose |
| 2017/0286113 A1 | 10/2017 | Shanbhogue et al. |
| 2017/0326233 A1 | 11/2017 | Demeule et al. |
| 2018/0065998 A1 | 3/2018 | Battrell et al. |
| 2018/0079909 A1 | 3/2018 | Matray et al. |
| 2018/0092993 A1 | 4/2018 | Desai et al. |
| 2018/0141935 A1 | 5/2018 | Josel et al. |
| 2018/0163052 A1 | 6/2018 | Matray et al. |
| 2018/0164322 A1 | 6/2018 | Matray et al. |
| 2018/0237641 A1 | 8/2018 | Matray et al. |
| 2018/0312468 A1 | 11/2018 | Zhang et al. |
| 2019/0016898 A1 | 1/2019 | Matray et al. |
| 2019/0136065 A1 | 5/2019 | Singh et al. |
| 2019/0144678 A1 | 5/2019 | Matray et al. |
| 2019/0153232 A1 | 5/2019 | Matray et al. |
| 2019/0177549 A1 | 6/2019 | Matray et al. |
| 2019/0300716 A1 | 10/2019 | Matray et al. |
| 2020/0032139 A1 | 1/2020 | Behrendt et al. |
| 2020/0109287 A1 | 4/2020 | Matray et al. |
| 2020/0164085 A1 | 5/2020 | Brandish et al. |
| 2020/0222554 A1 | 7/2020 | Matray et al. |
| 2020/0284798 A1 | 9/2020 | Matray et al. |
| 2020/0330610 A1 | 10/2020 | Desai et al. |
| 2020/0353089 A1 | 11/2020 | Matray |
| 2020/0353094 A1 | 11/2020 | Matray |
| 2020/0360526 A1 | 11/2020 | Matray |
| 2020/0392345 A1 | 12/2020 | Matray et al. |
| 2021/0032277 A1 | 2/2021 | Matray |
| 2021/0032474 A1 | 2/2021 | Matray et al. |
| 2021/0095130 A1 | 4/2021 | Matray et al. |
| 2021/0096135 A1 | 4/2021 | Matray et al. |
| 2021/0109104 A1 | 4/2021 | Jackson et al. |
| 2021/0128591 A1 | 5/2021 | Matray |
| 2021/0128739 A1 | 5/2021 | Matray |
| 2021/0139440 A1 | 5/2021 | Ramsden et al. |
| 2021/0253864 A1 | 8/2021 | Matray |
| 2021/0261782 A1 | 8/2021 | Matray |
| 2021/0285953 A1 | 9/2021 | Matray et al. |
| 2021/0340380 A1 | 11/2021 | Matray |
| 2021/0395530 A1 | 12/2021 | Matray et al. |
| 2022/0160887 A1 | 5/2022 | Matray et al. |
| 2022/0168433 A1 | 6/2022 | Matray et al. |
| 2022/0168435 A1 | 6/2022 | Matray et al. |
| 2022/0175951 A1 | 6/2022 | Boitano et al. |
| 2022/0220314 A1 | 7/2022 | Singh et al. |
| 2022/0227794 A1 | 7/2022 | Matray et al. |
| 2022/0305127 A1 | 9/2022 | Thomas et al. |
| 2022/0372297 A1 | 11/2022 | Matray et al. |
| 2022/0380603 A1 | 12/2022 | Matray et al. |
| 2022/0402963 A1 | 12/2022 | Matray et al. |

(56) References Cited

U.S. PATENT DOCUMENTS

| | | |
|---|---|---|
| 2023/0012304 A1 | 1/2023 | Matray et al. |
| 2023/0129481 A1 | 4/2023 | Matray et al. |
| 2024/0043455 A1 | 2/2024 | Battrell et al. |

FOREIGN PATENT DOCUMENTS

| | | | |
|---|---|---|---|
| CN | 103319378 | | 9/2013 |
| CN | 104072727 | | 10/2014 |
| CN | 105917226 | A | 8/2016 |
| CN | 106589005 | A | 4/2017 |
| CN | 107106685 | A | 8/2017 |
| CN | 107709470 | A | 2/2018 |
| CN | 109071961 | A | 12/2018 |
| CN | 109153860 | A | 1/2019 |
| GB | 2 372 256 | | 8/2002 |
| JP | S61-207395 | | 9/1986 |
| JP | 4-282391 | A | 10/1992 |
| JP | 2000-17183 | A | 1/2000 |
| JP | 2014527071 | A | 10/2014 |
| JP | 2017537266 | A | 5/2016 |
| JP | 2017-124994 | A | 7/2017 |
| JP | 2018507863 | A | 3/2018 |
| JP | 2019516807 | A | 6/2019 |
| JP | 2020508523 | A | 3/2020 |
| JP | 2020508523 | | 12/2020 |
| JP | 2020536845 | A | 12/2020 |
| JP | 7069033 | B2 | 5/2022 |
| KR | 10-1041446 | B1 | 6/2011 |
| KR | 10-2015-0007795 | A | 1/2015 |
| KR | 10-2020-0133374 | A | 11/2020 |
| SU | 1121931 | A | 4/1988 |
| WO | 95/02700 | A1 | 1/1995 |
| WO | WO 9506731 | A2 | 3/1995 |
| WO | 98/32463 | A2 | 7/1998 |
| WO | 01/73123 | A2 | 10/2001 |
| WO | 02/22883 | A1 | 3/2002 |
| WO | 02/083954 | A1 | 10/2002 |
| WO | 2004/007751 | A2 | 1/2004 |
| WO | 2007/094135 | A1 | 8/2007 |
| WO | WO 2009113645 | A1 | 9/2009 |
| WO | 2010/026957 | A1 | 3/2010 |
| WO | 2013/012687 | A2 | 1/2013 |
| WO | WO-2014064687 | A1 * | 5/2014 ........... A61K 47/543 |
| WO | 2014/147642 | A1 | 9/2014 |
| WO | WO 2015091953 | A1 | 6/2015 |
| WO | WO 2015155753 | A2 | 10/2015 |
| WO | WO-2016074093 | A1 | 5/2016 |
| WO | WO 2016183185 | A1 | 11/2016 |
| WO | 2017/003639 | A2 | 1/2017 |
| WO | WO 2017062271 | A2 | 4/2017 |
| WO | 2017/089890 | A1 | 6/2017 |
| WO | WO 2017094897 | A1 | 6/2017 |
| WO | 2017/173348 | A1 | 10/2017 |
| WO | 2017/177065 | A2 | 10/2017 |
| WO | WO 2017197144 | A1 | 11/2017 |
| WO | WO 2018045278 | A1 | 3/2018 |
| WO | 2018/060722 | A1 | 4/2018 |
| WO | 2019/071208 | A1 | 4/2019 |
| WO | WO 2019126691 | A1 | 6/2019 |
| WO | WO 2019182765 | A1 | 9/2019 |
| WO | WO 2020006285 | A1 | 1/2020 |
| WO | WO 2020219959 | A1 | 10/2020 |
| WO | 2021/062176 | A2 | 4/2021 |
| WO | 2021/067483 | A1 | 4/2021 |

OTHER PUBLICATIONS

Nolting, B. 'Linker Technologies for Antibody-Drug Conjugates', Ch. 5, pp. 71-100, In: "Antibody-Drug Conjugates", L. Ducry, Ed. 2013, Humana Press) (Year: 2013).*

Hasegawa et al (Clinical and Experimental Immunology, 2012, vol. 167, pp. 269-274) (Year: 2012).*

Liu et al (International Journal of Oncology, 2015, vol. 46, pp. 721-731) (Year: 2015).*

Oh et al (Muscle and Nerve, 1997, vol. 20, pp. 1146-1152) (Year: 1997).*

The abstract of Ciccotelli et al (Journal of Immunology, 2015, 194 (1 suppl) 214.5) (Year: 2015).*

Midoux et al (British Journal of Pharmacology, 2009, vol. 157, pp. 166-178) (Year: 2009).*

"What is an Analyte?," Google Search, dated Mar. 22, 2018, retrieved from https://www.google.com/search?q=what+is+an+analyte &rlz=lClGCEB_enUS775US775&oq-what+is+an+analyte&aqs= chrome..69i57j0I5.3231j0j7&s . . . 2 pages.

Arian et al., "1,9-Dialkoxyanthracene as a $^1O_2$-Sensitive Linker," *J. Am. Chem. Soc.* 133:3972-3980, 2011.

Babitskaya et al., "Bromoacyl Analogues of Phosphatidylcholine with Intramolecular Fluorescence Quenching and Their Use as Substrates for Continuous Monitoring of Phospholipase $A_2$ Activity," *Applied Biochemistry and Microbiology* 40(4):351-356, 2004.

Beaucage et al., "The Functionalization of Oligonucleotides Via Phosphoramidite Derivatives," *Tetrahedron* 49(10):1925-1963, 1993.

Becker et al., "New Thermotropic Dyes on Amino-Substituted Perylendicarboximides," *Chem. Eur. J.* 6(21):3984-3990, 2000.

Bergstrom et al., "A NaPi2b Antibody-Drug Conjugate Induces Durable Complete Tumor Regressions in Patient-Derived Xenograft Models of NSCLC," *IASLC 17th World Conference on Lung Cancer*, Vienna, Austria, Dec. 4-7, 2016 (8 pages).

Bergstrom et al., "Potent Promise," *Innovations in Pharmaceutical Technology* 49:16-20, 2014.

Bergstrom et al., "XMT-1522 induces tumor regressions in pre-clinical models representing HER2-positive and HER2 low-expressing breast cancer," Mersana Therapeutics, Abstract P4-14-28, 2015, 1 page.

Braeckmans et al., "Three-dimensional fluorescence recovery after photobleaching with the confocal scanning laser microscope," *Biophysical Journal* 85:2240-2252, 2003.

Braga et al., "Intracellular macromolecular mobility measured by fluorescence recovery after photobleaching with confocal laser scanning microscopes," *Molecular Biology of the Cell* 15:4749-4760, 2004.

Brinkley, "A brief survey of methods for preparing protein conjugates with dyes, haptens and crosslinking reagents," *Bioconjugate Chem* 3:2-13, 1992.

CAPLUS Accession No. 1975: 171341, Holy, "Nucleic acid components and their analogs. CLXXII. Aliphatic analogs of nucleosides, nucleotides, and oligonucleotides," *Collection of Czechoslovak Chemical Communications* 40(1):187-214, 1975. (1 page).

Chattopadhyay et al., "Brilliant Violet Fluorophores: A New Class of Ultrabright Fluorescent Compounds for Immunofluorescence Experiments," *Cytometry Part A* 81A:456-466, 2012.

Chong et al., "Oxygen Quenching of Pyrene-Lipid Fluorescence in Phosphatidylcholine Vesicles—A Probe for Membrane Organization," *Biophys. J.* 47:613-621, 1985.

Cuppoletti et al., "Oligomeric fluorescent labels for DNA," *Bioconjug. Chem.* 16(3):528-534, 2005.

Dai et al., "DNA-polyfluorophore excimers as sensitive reporters for esterases and lipases," *Chemical Communications* 46:1221-1223, 2010.

Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.

DiVittorio et al., "Synthetic peptides with selective affinity for apoptotic cells," *Organic & Biomolecular Chemistry* 4:1966-1976, 2006.

Dubrovsky, "Semiconductor nanoparticles as reporters in multi-plexed immunoassay and cell analysis," *International Journal of Nanoscience* 8(1 & 2):163-167, 2009.

Gao et al., "Libraries of Composite Polyfluors Built from Fluorescent Deoxyribosides," *Journal of the American Chemical Society* 124:11590-11591, 2002.

Gao et al., "Modified DNA Analogues That Sense Light Exposure with Color Changes," *Journal of the American Chemical Society* 126:12748-12749, 2004.

(56) References Cited

OTHER PUBLICATIONS

Gordon et al., "Analysis of simulated and experimental fluorescence recovery after photobleaching. Data for two diffusing components," *Biophysical Journal* 68:766-778, 1995.

Hanhela et al., "Synthesis and Evaluation of Fluorescent Materials for Colour Control of Peroxyoxalate Chemiluminescence. III. Yellow and Red Fluorescent Emitters," *Australian Journal of Chemistry* 34:1701-1717, 1981.

Haraguchi, "Live Cell Imaging: Approaches for Studying Protein Dynamics in Living Cells," *Cell Structure and Function* 27:333-334, 2002.

Jain et al. "Current ADC Linker Chemistry," *Pharm. Res.* 32:3526-3540, 2015.

Koo et al., "Fluorescent DNA chemosensors: identification of bacterial species by their volatile metabolites," *Chemical Communications* 47:11435-11437, 2011.

Kozma et al., "Fluorescent Ligands for Adenosine Receptors," *Bioorganic & Medicinal Chemistry Letters* 23: 26-36, 2013.

Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.

Leung et al., "7-Amino-4-Methyl-6-Sulfocoumarin-3-Acetic Acid: A Novel Blue Fluorescent Dye for Protein Labeling," *Bioorganic & Medicinal Chemistry Letters* 9: 2229-2232, 1999.

Li et al., "Polymeric Drugs: Advances in the development of pharmacologically active polymers," *Journal of Controlled Release* 219:360-382, 2015.

Liu et al., "Detection of prostate-specific membrane antigen on HUVECs in response to breast tumor-conditioned medium," *International Journal of Oncology* 38:1349-1355, 2011.

Liu et al., "DNA-Based Micelles: Synthesis, Micellar Properties and Size-Dependent Cell Permeability," *Chem. Eur. J.* 16:3791-3797, 2010 (14 Pages).

Luo et al., "Sensitive and rapid quantification of C-reactive protein using quantum dot-labeled microplate immunoassay," *Journal of Translational Medicine* 10(24):1-9, 2012.

Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.

Molotkovsky et al., "Perylenoyl- and Anthrylvinyl-Labeled Lipids as Membrane Probes," *Biochimica et Biophysica Acta* 778:281-288, 1984.

Nussbaumer et al., "Amplification of Chirality by Supramolecular Polymerization of Pyrene Oligomers," *Angewandte Chemie International Edition* 50:5490-5494, 2011.

Paris et al., "Probing DNA sequences in solution with a monomer-excimer fluorescence color change," *Nucleic Acids Research* 26(16):3789-3793, 1998.

Petreus et al., "Polyester imides containing main-chain phosphorus," *Revue Roumaine de Chimie* 34(8):971-978, 1994 (with English Abstract).

Pownall et al., "Kinetics of Spontaneous and Plasma-Stimulated Sphingomyelin Transfer," *Biochimica et Biophysica Acta* 712:169-176, 1982.

Pubchem, "US20100012929A1-20100121-C00010_4," SID No. 140452858, retrieved Mar. 29, 2016 from URL https://pubchem.ncbi.nlm.nih.gov/substance/140452858#sectio . . . , 6 pages.

Ren et al., "An Antisense Oligodeoxynucleotide-Doxorubicin Conjugate: Preparation and Its Reversal Multidrug Resistance of Human Carcinoma Cell Line In Vitro," *Nucleosides, Nucleotides & Nucleic Acids* 23(10):1595-1607, 2004.

RN 230952-79-1, Registry Database Compound, 1999.

Singh et al., "Multiplexed measurement of membrane protein populations," *Caplus* 2003:769075, 2003. (2 pages).

Stuart et al., "Site-Specific DNA-Doxorubicin Conjugates Display Enhanced Cytotoxicity to Breast Cancer Cells," *Bioconjugate Chemistry* 25:406-413, 2014.

Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 25, 2010, 23 pages).

Tram et al., "Oligonucleotide Labeling Using BODIPY Phosphoramidite," *Nucleosides, Nucleotides & Nucleic Acids* 30(1):1-11, 2011.

Wang et al., "Cruciforms: Assembling Single Crystal Micro- and Nanostructures from One to Three Dimensions and Their Applications in Organic Field-Effect Transistors," *Chem. Mater.* 21:2840-2845, 2009.

Wang et al., "DNA Polyfluorophores for Real-Time Multicolor Tracking of Dynamic Biological Systems," *Angew. Chem. Int. Ed.* 51:7176-7180, 2012.

Wilson et al., "Efficient Quenching of Oligomeric Fluorophores on a DNA Backbone," *Journal of the American Chemical Society* 129(50):15426-15427, 2007.

Wilson et al., "Oligodeoxyfluorosides: Strong Sequence of Dependence of Fluorescence Emission," *Tetrahedron* 63(17):3427-3433, 2007 (18 Pages).

Avirah et al., "Infrared Absorbing Croconaine Dyes: Synthesis and Metal Ion Binding Properties," *J. Org. Chem.* 73(1):274-279, 2008.

Li et al., "Responsive nanogel-based dual fluorescent sensors for temperature and $Hg^{2+}$ ions with enhanced detection sensitivity," *J. Mater. Chem.* 20:10716-10723, 2010.

Stewart et al., "The Fluorescence of a Chelating Two-Photon-Absorbing Dye is Enhanced with the Addition of Transition Metal Ions but Quenched in the Presence of Acid," *Proc. of SPIE* 9939(993904):1-10, 2016.

Zhang et al., "FRET Imaging of Enzyme-Responsive HPMA Copolymer Conjugate," *Macromolecular Bioscience* 17(1600215):1-8, 2017.

Doi et al., "Hetero-Selective DNA-Like Duplex Stabilized by Donor-Acceptor Interactions," *Chem. Eur. J.* 21:15974-15980, 2015.

Franceschin et al., "Synthesis of a Dibromoperylene Phosphoramidite Building Block and Its Incorporation at the 5' End of a G-Quadruplex Forming Oligonucleotide: Spectroscopic Properties and Structural Studies of the Resulting Dibromoperylene Conjugate," *Bioconjugate Chem* 22:1309-1319, 2011.

Johansson, "Choosing Reporter-Quencher Pairs for Efficient Quenching Through Formation of Intramolecular Dimers," *Methods in Molecular Biology* 335:17-29, 2006.

Masuko et al., "Fluorescence resonance energy transfer from pyrene to perylene labels for nucleic acid hybridization assays under homogenous solution conditions," *Nucleic Acids Research* 28(8):e34, 2000 (8 pages).

Saito et al., "Dual-labeled oligonucleotide probe for sensing adenosine via FRET: A novel alternative to SNPs genotyping," *Chem. Commun.*:2133-2135, 2007.

Takakusa et al., "Design and Synthesis of an Enzyme-Cleavable Sensor Molecule for Phosphodiesterase Activity Based on Fluorescence Resonance Energy Transfer," *J. Am. Chem. Soc.* 124(8):1653-1657, 2002.

Vinogradov et al., "Total synthesis and biochemical characterization of mirror image barnase," *Chem Sci.* 6: 2997-3002, 2015.

Breul et al., "Fluorescent monomers as building blocks for dye labeled polymers: synthesis and application in energy conversion, biolabeling and sensors," Chem. Soc. Rev. 42(12):5366-5407, 2013.

Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015, 1 page.

Rupcich et al., "Quenching of Fluorophore-Labeled DNA Oligonucleotides by Divalent Metal Ions: Implications for Selection, Design, and Applications of Signaling Aptamers and Signaling Deoxyribozymes," J. Am. Chem. Soc. 126(3):780-790, 2006.

Yu et al., "Targeted Delivery of an Anti-Inflammatory PDE4 Inhibitor to Immune Cells via an Antibody-drug Conjugate," Molecular Therapy 24(12):2078-2089, Dec. 2016.

(56) References Cited

OTHER PUBLICATIONS

Lapeyre et al., "Aryldithioethyloxycarbonyl (Ardec): A New Family of Amine Protecting Groups Removable under Mild Reducing Conditions and Their Applications to Peptide Synthesis," Chem. Eur. J. 12:3655-3671, 2006.
Mthembu et al., "Breaking a Couple: Disulfide Reducing Agents," ChemBioChem 21, 2020. (10 pages).
Poupart et al., "Aminopropargyl derivative of terpyridine-bis(methyl-enamine) tetraacetic acid chelate of europium (Eu (TMT)-AP3): a new reagent for fluorescent labelling of proteins and peptides," Org. Biomol. Chem. 4:4165-4177, Oct. 2006.
Finniss et al., "A versatile acid-labile linker for antibody-drug conjugates," Med. Chem, Commun; 5; Apr. 1, 2014, 4 pages.
Dropulic et al., "Update on New Antivirals Under Development for the Treatment of Double-Stranded DNA Virus Infections," Clinical Pharmacology & Therapeutics 88(5):610-619, Nov. 2010.
Irani et al., "Molecular properties of human IgG subclasses and their implications for designing therapeutic monoclonal antibodies against infectious diseases," Molecular Immunology 67:171-182, 2015.
McKinlay et al., "Cell-Penetrating, Guanidinium-Rich Oligophosphoesters: Effective and Versatile Molecular Transporters for Drug and Probe Delivery," J. Am. Chem. Soc. 138:3510-3517, Feb. 22, 2016.
Mersana Therapeutics, URL=http://www.mersana.com, download date Jan. 3, 2019, 9 pages.
Nolting, "Linker Technology for Antibody-Drug Conjugates," in Ducry (ed.), Antibody-Drug Conjugates, Humana Press, Totowa, NJ, 2013, Ch. 5, pp. 71-100.
Pelegrin et al., "Antiviral Monoclonal Antibodies: Can They Be More Than Simple Neutralizing Agents?" Trends in Microbiology 23(10):653-665, Oct. 2015.
Shuman et al., "Bacterial DNA repair by non-homologous end joining," Nature Reviews Microbiology 5:852-861, Nov. 2007.
Yurkovetskiy et al., "Advantages of Polyacetal Polymer-based Antibody Drug Conjugates: Application to Low Expression Targets," Mersana Therapeutics, technical paper #2645, 2014, 1 page.
STIC Search Report from American Chemical Society, for U.S. Appl. No. 17/255,353, dated Sep. 7, 2023. (143 pages).
Gupta et al., "Dendrimers: Novel Polymeric Nanoarchitectures for Solubility Enhancement," Biomacromolecules 7(3):649-658, Mar. 2006 [Published online Feb. 15, 2006]. (10 pages).
Shuey et al., "Cyclohexanediol Bisphosphates as Models for Phospholipid-Metal Ion Binding Sites," Bioorganic Chemistry 21:95-108, Mar. 1993. (14 pages).
Samal et al., "Cationic polymers and their therapeutic potential," Chemical Society Reviews 41:7147-7194, Aug. 2012. (48 pages).
Sun et al., "Self-assembled biodegradable micellar nanoparticles of amphiphilic and cationic block copolymer for siRNA delivery," Biomaterials 29:4348-4355, available online Aug. 2008. (8 pages).
Tabujew et al., "Chapter One: Functionalization of Cationic Polymers for Drug Delivery Applications," RSC Polymer Chemistry Series 13, 2015. (29 pages).
Wu Yi et al., "$^{Py}$A-Modified Oligodeoxyadenylates: Expanded Fluorescence Phenomena and Structural Formation," Chemistry—An Asian Journal 7:60-63, Nov. 2011. (4 pages).
Chen et al., "Synthesis and properties of new segmented block poly(urethane-urea)s containing phosphatidylcholine analogues and polybutadienes," Macro-Molecular Chemistry and Physics 197(5):1587-1597, May 1996. (11 pages).
Franzini et al., "Identification of Structure-Activity Relationships from Screening a Structurally Compact DNA-Encoded Chemical Library," Angewandte Chemie International Edition 54:3927-3931, Feb. 3, 2015 [with supporting information]. (41 pages).
Khandare et al., "Polymer-drug conjugates: Progress in polymeric prodrugs," Progress in Polymer Science 31(4):359-397, Apr. 2006. (39 pages).
Liu et al., "Increased Cytotoxicity and Decreased In Vivo Toxicity of FdUMP[10] Relative to 5-FU," Nucleosides & Nucleotides 18(8):1789-1802, Aug. 1999. (14 pages).

Petersen et al., "Acyclic, achiral enamide nucleoside analogues. The importance of the C=C bond in the analogue for its ability to mimic natural nucleosides," Organic & Biomolecular Chemistry 1:3293-3296, Sep. 4, 2003. (4 pages).
Striebel et al., "Enhancing sensitivity of human herpes virus diagnosis with DNA microarrays using dendrimers," Experimental and Molecular Pathology 77:89-97, Oct. 2004 [Published online Jul. 15, 2004]. (9 pages).
Bargh et al., "Cleavable linkers in antibody-drug conjugates," Chemical Society Reviews 48(16):4361-4374, Aug. 21, 2019. (15 pages).
CAPLUS Accession No. 1991:467753, Mielewczyk et al., "5' end fluorescent labelling of oligonucleotides with riboflavin-derived phosphitylating reagent," Acta Biochimica Polonica 36(3-4):225-233, 1989. (1 page).
CAPLUS Accession No. 1995:665426, Chen et al., "Synthesis of Novel Phosphoramidite Reagents for the Attachment of Antisense Oligonucleotides to Various Regions of the Benzophenanthridine Ring System," Bioconjugate Chemistry 6(4):473-482, Jul. 1, 1995. (1 page).
CAPLUS Accession No. 1995:733249, WO9506731A2, filed Mar. 9, 1995. (1 page).
CAPLUS Accession No. 1995:849926, Reed et al., "Structure-Activity Relationships of Cytotoxic Cholesterol-Modified DNA Duplexes," Journal of Medicinal Chemistry 38(22):4587-4596, Oct. 27, 1995. (1 page).
CAPLUS Accession No. 1997:497709, Puri et al., "Synthesis of 5'-polyarene-tethered oligo-DNAs and the thermal stability and spectroscopic properties of their duplexes and triplexes," Tetrahedron 53(30):10409-10432, Jul. 28, 1997. (1 page).
Chen et al., "Synthesis of Novel Phosphoramidite Reagents for the Attachment of Antisense Oligonucleotides to Various Regions of the Benzophenanthridine Ring System," Bioconjugate Chemistry 6(4):473-482, Jul. 1, 1995. (10 pages).
Kolpashchikov, "Binary Probes for Nucleic Acid Analysis," Chemical Reviews 110(8):4709-4723, Jun. 28, 2010. (15 pages).
Lee et al., "The spectroscopic analysis for binding of amphipathic and antimicrobial model peptides containing pyrenylalanine and tryptophan to lipid bilayer," Biochimica et Biophysica Acta 984:174-182, Sep. 4, 1989. (9 pages).
Liso et al., "Polymeric drugs derived from Ibuprofen with improved antiinflammatory profile," Journal of Biomedical Materials Research 32:553-560, Dec. 1996. (8 pages).
Lvnitski et al., "Introducing charge transfer functionality into prebiotically relevant β-sheet peptide fibrils," Chemical Communications 50:6733-6736, May 12, 2014. (4 pages).
Marras et al., "Efficiencies of fluorescence resonance energy transfer and contact-mediated quenching in oligonucleotide probes," Nucleic Acids Research 30(21):e122, Nov. 1, 2002. (8 pages).
Mielewczyk et al., "5' end fluorescent labelling of oligonucleotides with riboflavin-derived phosphitylating reagent," Acta Biochimica Polonica 36(3-4):225-233, 1989. (9 pages).
Pawelczyk et al., "Molecular Consortia-Various Structural and Synthetic Concepts for More Effective Therapeutics Synthesis," International Journal of Molecular Sciences 19:1104, Apr. 6, 2018. (19 pages).
Puri et al., "Synthesis of 5'-polyarene-tethered oligo-DNAs and the thermal stability and spectroscopic properties of their duplexes and triplexes," Tetrahedron 53(30):10409-10432, Jul. 28, 1997. (24 pages).
Reed et al., "Structure-Activity Relationships of Cytotoxic Cholesterol-Modified DNA Duplexes," Journal of Medicinal Chemistry 38(22):4587-4596, Oct. 27, 1995. (10 pages).
Wang et al., "Novel dexamethasone-HPMA copolymer conjugate and its potential application in treatment of rheumatoid arthritis," Arthritis Research & Therapy 9(1):R2, Jan. 18, 2007. (9 pages).
Wang, "Modern Synthetic Methods and Technologies of Polymers," Common Knowledge Evidence, Tongji University Press, 1st Edition, Jul. 2013, pp. 210-211. (includes portion of Chinese Office Action with English Summary of relevance) (20 pages).
Xu et al., "Synthesis of [D-Pyrenylalanine$^{4,4'}$]gramicidin S by Solid-Phase-Synthesis and Cyclization-Cleavage Method with Oxime Resin," Chemistry Letters 21:191-194, Feb. 1992. (4 pages).

(56) References Cited

OTHER PUBLICATIONS

U.S. Appl. No. 17/602,718, filed Oct. 8, 2021, Matray Tracy.
U.S. Appl. No. 17/602,722, filed Oct. 8, 2021, Matray Tracy.
U.S. Appl. No. 16/961,403, filed Jul. 10, 2020, Matray Tracy.
Aviñó et al., "Solid-phase synthesis of oligomers carrying several chromophore units linked by phosphodiester backbones," *Bioorganic & Medicinal Chemistry Letters 18*:2306-2310, 2008.
Bag et al., "Triazolyl-donor-acceptor chromophore-decorated unnatural amino acids and peptides: FRET events in a β-turn conformation," *Chem. Commun. 50*:433-435, 2014.
Boldyrev et al., "Synthesis and Characteristics of New Fluorescent Probes Based on Cardiolipin," *Russian Journal of Bioorganic Chemistry 35*(2):219-224, 2009.
Buckhout-White et al., "Assembling programmable FRET-based photonic networks using designer DNA scaffolds," *Nature Communications 5*:5615, Dec. 11, 2014. (16 pages).
CAS Registry No. 862288-26-4, American Chemical Society, 2021. (1 page).
Chang et al., "A General Approach for Generating Fluorescent Probes to Visualize Piconewton Forces at the Cell Surface," *J. Am. Chem. Soc. 138*:2901-2904, 2016. (4 pages).
Damian et al., "Synthesis and DNA Interaction of Platinum Complex/Peptide Chimera as Potential Drug Candidates," *Eur. J. Org. Chem.* 6161-6170, 2010.
De Vos et al., "New Non Nucleosidic Phosphoramidites for the Solid Phase Multi-Labelling of Oligonucleotides: Comb- and Multifork-Like Structures," *Nucleosides & Nucleotides 13*(10):2245-2265, 1994.
Drescher et al., "General Synthesis and Aggregation Behaviour of New Single-Chain Bolaphospholipids: Variations in Chain and Headgroup Structures," *Chemistry—A European Journal 14*(22):6796-6804, 2008.
Griesang et al., "Four-Color, Enzyme-Free Interrogation of DNA Sequences with Chemically Activated, 3'-Fluorphore-Labeled Nucleotides," *Angew. Chem. Int. Ed. 45*:6144-6148, 2006.
Guryev et al., "Control of the Fluorescence of Dye-Antibody Conjugates by (2-Hydroxypropyl)-β-cyclodextrin in Fluorescence Microscopy and Flow Cytometry," *Analytical Chemistry 83*:7109-7114, Aug. 16, 2011.
Kashida et al., "A Cationic Dye Triplet as a Unique "Glue" That Can Connect Fully Matched Termini of DNA Duplexes," *Chem. Eur. J. 17*:2614-2622, 2011.
Krueger at al., "Fluorescent Amino Acids: Modular Building Blocks for the Assembly of New Tools for Chemical Biology," *ChemBioChem 14*:788-799, 2013.
Lewis et al., "Orientation Control of Fluorescence Resonance Energy Transfer Using DNA as a Helical Scaffold," *J. Am. Chem. Soc. 127*(28):10002-10003, 2005.
Moss, "Nomenclature of Fused and Bridged Fused Ring Systems," *Pure & Appl. Chem. 70*(1):143-216, 1998.
Phares et al., "Improving the Stability and Sensing of Electrochemical Biosensors by Employing Trithiol-Anchoring Groups in a Six-Carbon Self-Assembled Monolayer," *Anal. Chem. 81*(3):1095-1100, Feb. 1, 2009.
Rochat et al., "Water-Soluble Cationic Conjugated Polymers: Response to Electron-Rich Bioanalytes," *J. Am. Chem. Soc. 135*:17703-17706, 2013.
Sun et al., "Dual-Color Fluorescence Imaging of Magnetic Nanoparticles in Live Cancer Cells Using Conjugated Polymer Probes," *Scientific Reports 6*:22368, 2016. (12 pages).
Sun et al., "High yield production of high molecular weight poly-(ethylene glycol)/ a-cyclodextrin polyrotaxanes by aqueous one-pot approach," *Polymer 53*:2884-2889, 2012.
Sun et al., "Ultrabright and Multicolorful Fluorescence of Amphiphilic Polyethyleneimine Polymer Dots for Efficiently Combined Imaging and Therapy," *Scientific Reports 3*:3036, 2013. (6 pages).
Teyssot et al., "Aromatic Nitrogen Donors for Efficient Copper(1)-NHC CuAAC under Reductant-Free Conditions," *Eur. J. Org. Chem.* 3507-3515, 2010.
Vybornyi et al., "Formation of Two-Dimensional Supramolecular Polymers by Amphiphilic Pyrene Oligomers," *Angew. Chem. Int. Ed. 52*:114488-11493, 2013.
Wang et al., Fluorescence-Based Evaluation of the Partitioning of Lipids and Lipidated Peptides into Liquid-Ordered Lipid Microdomains: A Model for Molecular Partitioning into "Lipid Rafts," *Biophysical Journal 79*:919-933, Aug. 2000.
Winiger et al., "Long-Distance Electronic Energy Transfer in Light-Harvesting Supramolecular Polymers," *Angew. Chem. Int. Ed. 53*:13609-13613, 2014.
Zhao et al., "Mussel-Inspired One-Pot Synthesis of a Fluorescent and Water-Soluble Polydopamine-Polyethyleneimine Copolymer," *Macromol. Rapid Commun. 36*:909-915, 2015.

\* cited by examiner

PROGRAMMABLE POLYMERIC DRUGS

BACKGROUND

Field

Embodiments of the present invention are generally directed to dimeric and polymeric biologically active compounds having spacing groups, and methods for their preparation and use in various therapeutic methods.

Description of the Related Art

Targeted drug conjugates, unlike, e.g., chemotherapy, are intended to target only diseased cells and spare healthy cells. Typically, conjugates are composed of a targeting molecule that is linked to a biologically active payload or drug. By combining the unique targeting capability with the therapeutic effectiveness of a biologically active drug, conjugates can deliver the drug only to the intended target and minimize potential side effects.

Antibody-drug conjugates (ADCs) are one class of targeted drug conjugates that are of particular interest for cancer treatment. ADCs combine the targeting features of monoclonal antibodies with cancer-killing ability of cytotoxic agents to provide a therapeutic with several advantages over other chemotherapeutics. However, challenges related to the complexity of ADC constructs, specifically the chemical linker between antibody and drug, has caused significant difficulties for development of new and effective therapeutics. Although the first ADC was approved in 2001, it took almost a decade before the next ADC was approved. As of today, only Adcetris® and Kadcyla® are commercially available globally (Zevalin® has been approved in China only). Pioneers Pfizer/Wyeth withdrew Mylotarg® in 2010 after safety issues were observed during a comparative clinical trial.

Thus, there exists a need in the art for potent, targeting drug conjugates having a large therapeutic index. Ideally, such drug conjugates should provide sensitive discrimination between healthy and diseased tissues (e.g., tumor cells). The present invention fulfills this need and provides further related advantages.

BRIEF SUMMARY

In brief, embodiments of the present invention are generally directed to compounds useful as a targeted drug conjugate, optionally comprising fluorescent and/or colored dyes that enable selective delivery to targets, such as tumor cells, as well as reagents for their preparation. Methods for preparation of such molecules as well as use of the same for providing therapeutic treatment to a patient in need thereof are also described.

Embodiments of the presently disclosed compounds include one or more biologically active moieties covalently linked by a linker ("L"). Advantageously, embodiments of the present invention provide compounds that can be incorporated during polymer synthesis or attached post-synthetically. In addition, embodiments described herein allow incorporation of multiple biologically active moieties within the same compound as well as the optional inclusion of a targeting moiety.

In one embodiment, compounds having the following structure (I) are provided:

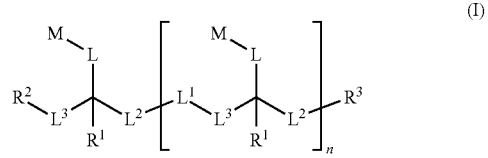

or a stereoisomer, tautomer or salt thereof, wherein $R^1$, $R^2$, $R^3$, $L^1$, $L^2$, $L^3$, M and n are as defined herein. Compounds of structure (I) find utility in a number of applications, including use as therapeutic agents for various treatment methods.

In another embodiment, a method of treating a disease is provided, the method comprising administering to a subject in need thereof a therapeutically effective amount of a compound of structure (I) or a composition comprising a compound of structure (I), wherein each M is independently a biologically active moiety effective for treating the disease.

These and other aspects of the invention will be apparent upon reference to the following detailed description.

BRIEF DESCRIPTION OF THE DRAWINGS

In the figures, identical reference numbers identify similar elements.

The sizes and relative positions of elements in the figures are not necessarily drawn to scale and some of these elements are enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
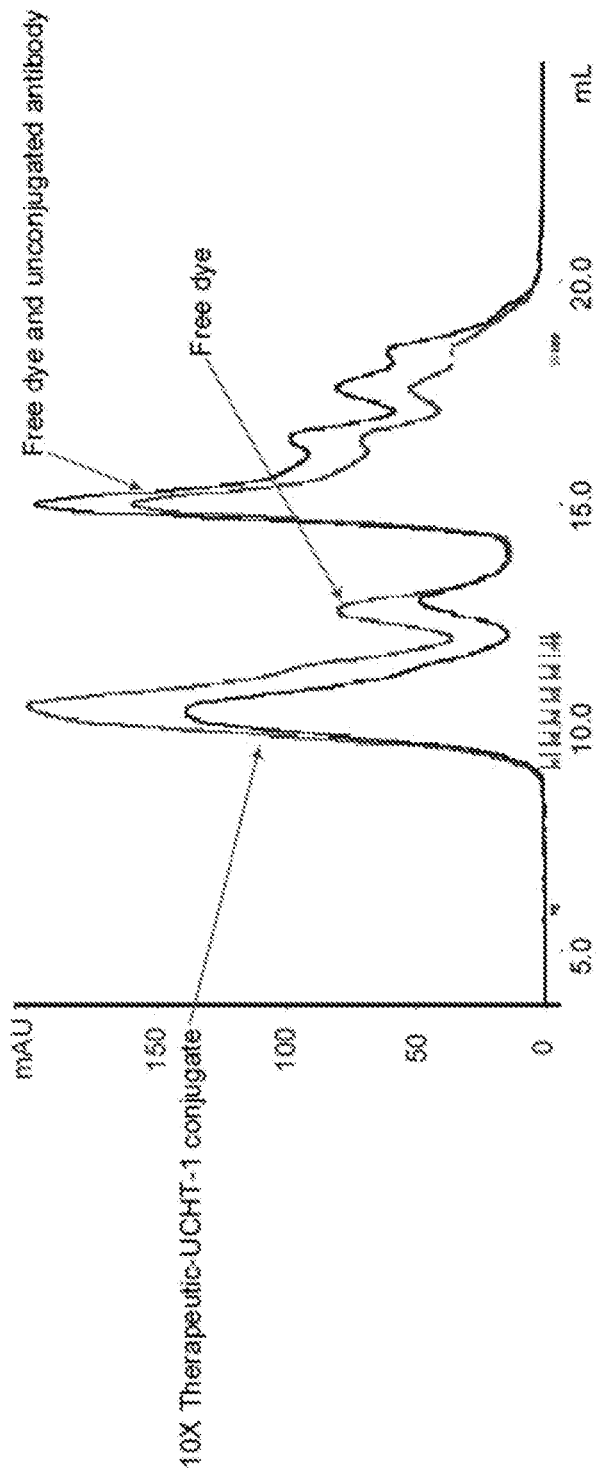
FIG. 1 provides an SEC spectra showing Compound 7 conjugated to UCHT-1 antibody.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ group.
"Carboxy" refers to the —$CO_2H$ group.
"Cyano" refers to the —CN group.
"Formyl" refers to the —C(=O)H group.
"Hydroxy" or "hydroxyl" refers to the —OH group.
"Imino" refers to the =NH group.
"Nitro" refers to the —$NO_2$ group.
"Oxo" refers to the =O substituent group.
"Sulfhydryl" refers to the —SH group.
"Thioxo" refers to the =S group.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(=$R_a$)($R_b$)$R_c$, wherein each of $R_a$, $R_b$ and $R_c$ is as defined for compounds of structure (I).

"Alkoxy" refers to a group of the formula —$OR_a$ where $R_a$ is an alkyl group as defined above containing one to twelve carbon atoms. Unless stated otherwise specifically in the specification, an alkoxy group is optionally substituted.

"Alkoxyalkylether" refers to a group of the formula —$OR_aR_b$ where $R_a$ is an alkylene group as defined above containing one to twelve carbon atoms, and $R_b$ is an alkylether group as defined herein. Unless stated otherwise specifically in the specification, an alkoxyalkylether group is optionally substituted, for example substituted with an alcohol or —OP(=Ra)($R_b$)Rc, wherein each of Ra, Rb and Rc is as defined for compounds of structure (I).

"Heteroalkyl" refers to an alkyl group, as defined above, comprising at least one heteroatom (e.g., Si, N, O, P or S) within the alkyl group or at a terminus of the alkyl group. In some embodiments, the heteroatom is within the alkyl group (i.e., the heteroalkyl comprises at least one carbon-[heteroatom]x-carbon bond, where x is 1, 2 or 3). In other embodiments, the heteroatom is at a terminus of the alkyl group and thus serves to join the alkyl group to the remainder of the molecule (e.g., M1-H-A), where M1 is a portion of the molecule, H is a heteroatom and A is an alkyl group). Unless stated otherwise specifically in the specification, a heteroalkyl group is optionally substituted. Exemplary heteroalkyl groups include ethylene oxide (e.g., polyethylene oxide), optionally including phosphorous-oxygen bonds, such as phosphodiester bonds.

"Heteroalkoxy" refers to a group of the formula —$OR_a$ where $R_a$ is a heteroalkyl group as defined above containing one to twelve carbon atoms. Unless stated otherwise specifically in the specification, a heteroalkoxy group is optionally substituted.

"Heteroalkylene" refers to an alkylene group, as defined above, comprising at least one heteroatom (e.g., Si, N, O, P or S) within the alkylene chain or at a terminus of the alkylene chain. In some embodiments, the heteroatom is within the alkylene chain (i.e., the heteroalkylene comprises at least one carbon-[heteroatom]-carbon bond, where x is 1, 2 or 3). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. Exemplary heteroalkylene groups include ethylene oxide (e.g., polyethylene oxide) and the "C," "HEG," and "PEG 1K" linking groups illustrated below:

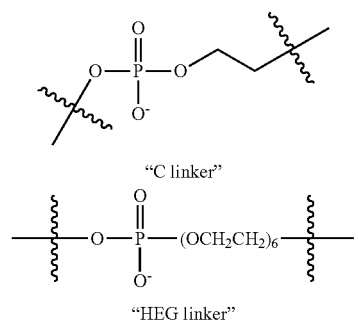

"C linker"

"HEG linker"

-continued

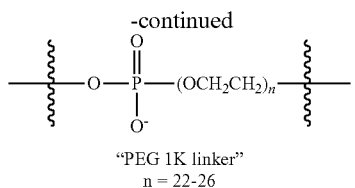

"PEG 1K linker"
n = 22-26

Multimers of the above C-linker, HEG linker and/or PEG 1K linker are included in various embodiments of heteroalkylene linkers. In some embodiments of the PEG 1K linker, n ranges from 20-25, for example n is 20, 21, 22, 23, 24, or 25. Multimers may comprise, for example, the following structure:

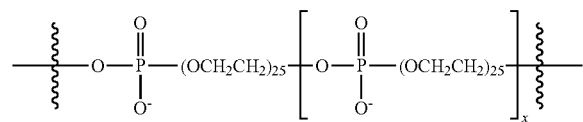

wherein x is 0 or an integer greater than 0, for example, x ranges from 0-100 (e.g., 1, 2, 3, 4, 5, 6, 7, 8, 9 or 10).

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatoms. Exemplary heteroatomic linkers include single atoms selected from the group consisting of Si, O, N, P and S, and multiple heteroatoms for example a linker having the formula —P(O$^-$)(═O)O— or —OP(O$^-$)(═O)O$^-$ and multimers and combinations thereof.

"Phosphate" refers to the —OP(═O)(R$_a$)R$_b$ group, wherein R$_a$ is OH, O$^-$ or OR$_c$; and R$_b$ is OH, O$^-$, OR$_c$, a thiophosphate group or a further phosphate group, wherein R, is a counter ion (e.g., Na$^+$ and the like).

"Phosphoalkyl" refers to the —OP(═O)(R$_a$)R$_b$ group, wherein R$_a$ is OH, O$^-$ or OR$_c$; and R$_b$ is -Oalkyl, wherein R$_c$ is a counter ion (e.g., Na$^+$ and the like). Unless stated otherwise specifically in the specification, a phosphoalkyl group is optionally substituted. For example, in certain embodiments, the -Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(═R$_a$)(R$_b$)R$_c$, wherein each of R$_a$, R$_b$ and R$_c$ is as defined for compounds of structure (I).

"Phosphoalkylether" refers to the —OP(═O)(R$_a$)R$_b$ group, wherein R$_a$ is OH, O$^-$ or OR$_c$; and R$_b$ is -Oalkylether, wherein R$_c$ is a counter ion (e.g., Na$^+$ and the like). Unless stated otherwise specifically in the specification, a phosphoalkylether group is optionally substituted. For example, in certain embodiments, the -Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether, thiophosphoalkylether or —OP(═R$_a$)(R$_b$)R$_c$, wherein each of R$_a$, R$_b$ and R$_c$ is as defined for compounds of structure (I).

"Thiophosphate" refers to the —OP(═R$_a$)(R$_b$)R$_c$ group, wherein R$_a$ is O or S, R$_b$ is OH, O$^-$, S$^-$, OR$_d$ or SR$_d$; and R$_c$ is OH, SH, O$^-$, S$^-$, OR$_d$, SR$_d$, a phosphate group or a further thiophosphate group, wherein R$_d$ is a counter ion (e.g., Na$^+$ and the like) and provided that: i) R$_a$ is S; ii) R$_b$ is S or SR$_d$; iii) R$_c$ is SH, S$^-$ or SR$_d$; or iv) a combination of i), ii) and/or iii).

"Thiophosphoalkyl" refers to the —OP(═R$_a$)(R$_b$)R$_c$ group, wherein R$_a$ is O or S, R$_b$ is OH, O$^-$, S$^-$, OR$_d$ or SR$_d$; and R$_c$ is -Oalkyl, wherein R$_d$ is a counter ion (e.g., Na$^+$ and the like) and provided that: i) R$_a$ is S; ii) R$_b$ is S or SR$_d$; or iii)R$_a$ is S and R$_b$ is S or SR$_d$. Unless stated otherwise specifically in the specification, a thiophosphoalkyl group is optionally substituted. For example, in certain embodiments, the -Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(═R$_a$)(R$_b$)R$_c$, wherein each of R$_a$, R$_b$ and R$_c$ is as defined for compounds of structure (I).

"Thiophosphoalkylether" refers to the —OP(═R$_a$)(R$_b$)R$_c$ group, wherein R$_a$ is O or S, R$_b$ is OH, O$^-$, S$^-$, OR$_d$ or SR$_d$; and R$_c$ is -Oalkylether, wherein R$_d$ is a counter ion (e.g., Na$^+$ and the like) and provided that: i) R$_a$ is S; ii) R$_b$ is S$^-$ or SR$_d$; or iii)R$_a$ is S and R$_b$ is S$^-$ or SR$_d$. Unless stated otherwise specifically in the specification, a thiophosphoalkylether group is optionally substituted. For example, in certain embodiments, the -Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(═R$_a$)(R$_b$)R$_c$, wherein each of R$_a$, R$_b$ and R$_c$ is as defined for compounds of structure (I).

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptly, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tertracyclic, and the like.

The term "substituted" used herein means any of the above groups (e.g., alkyl, alkylene, alkenylene, alkynylene, heteroalkylene, heteroalkenylene, heteroalkynylene, alkoxy, alkylether, alkoxyalkylether, heteroalkyl, heteroalkoxy, phosphoalkyl, phosphoalkylether, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In some embodiments, the optional substituent is $-OP(=R_a)(R_b)R_c$, wherein each of $R_a$, $R_b$ and $R_c$ is as defined for compounds of structure (I). In addition, each of the foregoing substituents may also be optionally substituted with one or more of the above substituents.

"Conjugation" or "bio-conjugation" refers to a chemical strategy for forming a stable covalent bond between two molecules. The term "bio-conjugation" is generally used when one of the molecules is a biomolecule (e.g., an antibody). The product or compound resulting from such a strategy is a conjugate, is conjugated, or a grammatically equivalent.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

The term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the invention (e.g., compounds of structure (I) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A "reactive group" is a moiety capable of reacting with a second reactive groups (e.g., a "complementary reactive group") to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin, thiirane and the like.

"Solid support" refers to any solid substrate known in the art for solid-phase support of molecules, for example a "microparticle" refers to any of a number of small particles useful for attachment to compounds of the invention, including, but not limited to, glass beads, magnetic beads, polymeric beads, nonpolymeric beads, and the like. In certain embodiments, a microparticle comprises polystyrene beads.

A "solid support reside" refers to the functional group remaining attached to a molecule when the molecule is cleaved from the solid support. Solid support residues are known in the art and can be easily derived based on the structure of the solid support and the group linking the molecule thereto.

A "targeting moiety" is a moiety that selectively binds or associates with a particular target, such as a tumor cell antigen. "Selectively" binding or associating means a targeting moiety preferentially associates or binds with the desired target relative to other targets. In some embodiments the compounds disclosed herein include linkages to targeting moieties for the purpose of selectively binding or associating the compound with a tumor cell antigen (i.e., the target of the targeting moiety), thus allowing delivery of the biologically active moiety to the tumor cell. Exemplary targeting moieties include, but are not limited to, antibodies, antigens, nucleic acid sequences, enzymes, proteins, cell surface receptor antagonists, and the like. In some embodiments, the targeting moiety is a moiety, such as an antibody, that selectively binds or associates with a target feature on or in a cell, for example a target feature on a cell membrane or other cellular structure, thus allowing for delivery of a biologically active moiety to or into cells of interest. Small molecules that selectively bind or associate with a desired biological target are also contemplated as targeting moieties in certain embodiments. One of skill in the art will understand other biological targets, and the corresponding targeting moiety, that will be useful in various embodiments.

"Physiologically cleavable linker" refers to a molecular linkage that can be split or separated a prescribed manner, resulting in two or more separate molecules while in the presence of an in vivo or in vitro environment of an organism or cell system. Generally, physiological conditions that induce such a cleavage or scission event may include a temperature ranging from about 20 to 40° C., an atmospheric pressure of about 1 atm (101 kPa or 14.7 psi), a pH of about 6 to 8, a glucose concentration of about 1 to 20 mM, atmospheric oxygen concentration, and earth gravity. In some embodiments, physiological conditions include enzymatic conditions (i.e., enzymatic cleavage). Bond cleavage or scission can be homolytic or heterolytic.

Embodiments of the invention disclosed herein are also meant to encompass all compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively.

Isotopically-labeled compounds of structure (I) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds described herein. Embodiments of the present invention include all solvates of the described compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

Embodiments of the compounds of the invention (e.g., compounds of structure I), or their salts, tautomers or solvates may contain one or more stereocenters and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other features giving rise to geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

As noted above, in one embodiment of the present invention, compounds useful as covalent linkers between biologically active moieties and targeting moieties are provided. In other embodiments, compounds useful as synthetic intermediates for preparation of compounds comprising one or more biologically active moieties are provided. In general terms, embodiments of the present invention are directed to polymers with pendant biologically active moieties. The biologically active moieties are linked by a linking moiety. Without wishing to be bound by theory, it is believed the linker helps to shield or suspend the biological activity until release of the drug at the desired target. In another aspect, the linker provides a link between the biologically active moiety and a targeting moiety, which acts to increase accumulation of the biologically active moiety at the desired target. That is, the biological activity is only operative or increased due to accumulation at the intended target, thus minimizing potential side effects of the therapeutic (e.g., cytotoxicity).

In other embodiments is provided a compound having the following structure (I):

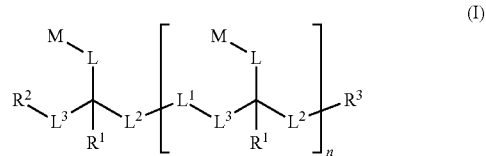

or a stereoisomer, pharmaceutically acceptable salt or tautomer thereof, wherein:

M is, at each occurrence, independently a biologically active moiety, or fragment thereof, a prodrug of a biologically active moiety, or fragment thereof, a fluorescent dye, an imaging agent, or a radioisotope binding site, provided at least one occurrence of M is not a fluorescent dye;

L is a physiologically cleavable linker;

$L^1$, $L^2$ and $L^3$ are, at each occurrence, independently an optional alkylene, alkenylene, alkynylene, heteroalkylene, heteroalkenylene, heteroalkynylene or heteroatomic linker;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q, or a protected form thereof, or L';

$R_a$ is O or S;

$R_b$ is OH, SH, O⁻, S⁻, OR$_d$ or SR$_d$;

$R_c$ is OH, SH, O⁻, S⁻, OR$_d$, OL', SR$_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with a complementary reactive group Q' on a targeting moiety;

L' is, at each occurrence, independently a linker comprising a covalent bond to Q, a targeting moiety, a linker comprising a covalent bond to a targeting moiety, a linker comprising a covalent bond to a solid support, a linker comprising a covalent bond to a solid support residue, a linker comprising a covalent bond to a nucleoside or a linker comprising a covalent bond to a further compound of structure (I); and n is an integer of one or greater.

The various linkers and substituents (e.g., M, Q, $R^1$, $R^2$, $R^3$, $R_c$, L, $L^1$, $L^2$, $L^3$ and L') in the compound of structure (I) are optionally substituted with one more substituent. For example, in some embodiments the optional substituent is selected to optimize the water solubility, permeability, retention, or other property of the compound of structure (I). In certain embodiments, each alkyl, alkoxy, alkylether, alkoxyalkylether, phosphoalkyl, thiophosphoalkyl, phosphoalkylether and thiophosphoalkylether in the compound of structure (I) is optionally substituted with one more substituent selected from the group consisting of hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether. In certain embodiments the optional substituent is —OP(=$R_a$)($R_b$)$R_c$, where $R_a$, $R_b$ and $R_c$ are as defined for the compound of structure (I). In certain embodiments, substituents are selected to increase cellular or tissue permeation. In related embodiments, substituents are selected to increase cellular or tissue retention In some embodiments, $L^1$ is at each occurrence, independently an optional alkylene, alkenylene, alkynylene, heteroalkylene, heteroalkenylene, heteroalkynylene or heteroatomic linker. In other embodiments, $L^1$ is a heteroalkylene linker. For example, in some embodiments, the compound has the following structure (IA):

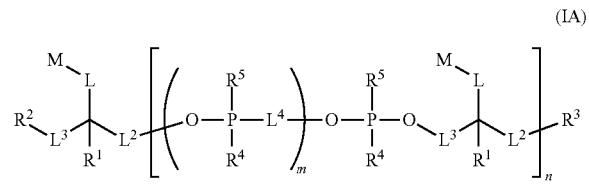

(IA)

wherein:

$L^4$ is, at each occurrence, independently an alkylene, alkenylene, alkynylene, heteroalkylene, heteroalkenylene or heteroalkynylene linker;

$R^4$ is, at each occurrence, independently OH, SH, O⁻, S⁻, $OR_d$ or $SR_d$;

$R^5$ is, at each occurrence, independently oxo, thioxo or absent; and m is, at each occurrence, independently an integer of zero or greater.

In some embodiments, $L^4$ is at each occurrence, independently a heteroalkylene linker. In other more specific embodiments, $L^4$ is at each occurrence, independently an alkylene oxide linker. For example, in some embodiments $L^4$ is polyethylene oxide, and the compound has the following structure (IB):

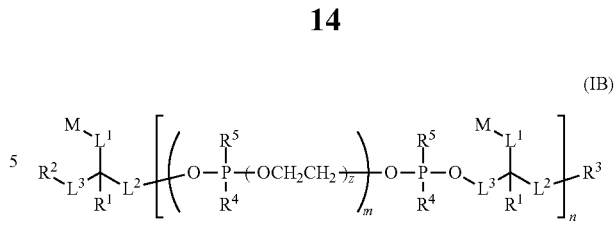

(IB)

wherein z is an integer from 1 to 100. In some embodiments of (IB), z is an integer from 3 to 6, for example about 6. In some embodiments z is 3. In some embodiments z is 4. In some embodiments, z is 5. In some embodiments, z is 6.

The linker L can be used as a point of attachment of the M moiety to the remainder of the compound. For example, in some embodiments a synthetic precursor to the compound of structure (I) is prepared, and the M moiety is attached to the synthetic precursor using any number of facile methods known in the art, for example methods referred to as "click chemistry." For this purpose any reaction which is rapid and substantially irreversible can be used to attach M to the synthetic precursor to form a compound of structure (I). Exemplary reactions include the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2]cycloaddition, alkene and tetrazine inverse-demand Diels-Alder, alkene and tetrazole photoreaction and various displacement reactions, such as displacement of a leaving group by nucleophilic attack on an electrophilic atom. Exemplary displacement reactions include reaction of an amine with: an activated ester; an N-hydroxysuccinimide ester; an isocyanate; an isothioscyanate or the like. In some embodiments the reaction to form L may be performed in an aqueous environment.

Accordingly, in some embodiments L is at each occurrence a linker comprising a functional group capable of formation by reaction of two complementary reactive groups, for example a functional group which is the product of one of the foregoing "click" reactions. In various embodiments, for at least one occurrence of L, the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester (e.g., N-hydroxysuccinimide ester), ketone, α,β-unsaturated carbonyl, alkene, maleimide, α-haloimide, epoxide, aziridine, tetrazine, tetrazole, phosphine, biotin or thiirane functional group with a complementary reactive group, for example, reaction of an amine with an N-hydroxysuccinimide ester or isothiocyanate.

In other embodiments, for at least one occurrence of L, the functional group can be formed by reaction of an alkyne and an azide. In other embodiments, for at least one occurrence of L, the functional group can be formed by reaction of an amine (e.g., primary amine) and an N-hydroxysuccinimide ester or isothiocyanate.

In more embodiments, for at least one occurrence of L, the functional group comprises an alkene, ester, amide, thioester, disulfide, carbocyclic, heterocyclic or heteroaryl group. In more embodiments, for at least one occurrence of L, the functional group comprises an alkene, ester, amide, thioester, thiourea, disulfide, carbocyclic, heterocyclic or heteroaryl group. In other embodiments, the functional group comprises an amide or thiourea. In some more specific embodiments, for at least one occurrence of L, L is a linker comprising a triazolyl functional group. While in other embodiments, for at least one occurrence of L, L is a linker comprising an amide or thiourea functional group.

Some embodiments provide an L that is able to be cleaved under the appropriate conditions (e.g., physiological conditions). Accordingly, in some embodiments, L comprises an amide bond, an ester bond, a disulfide bond, a hydrazone, a phosphotriester, a diester, β-glucuronide, a double bond, a triple bond, an ether bond, a ketone, a diol, a cyano, a nitro or combinations thereof.

In some embodiments, L comprises tert-butyloxycarbonyl, paramethoxybenzyl, dialkyl or diaryldialkoxysilane, orthoester, acetal, β-thiopropionate, ketal, phosphoramidate, hydrazone, vinyl ether, imine, aconityl, trityl, polyketal, bisarylhydrazone, diazobenzene, vivinal diol, pyrophosphate diester, or valine citrulline.

In certain embodiments, L is, at each occurrence, independently a linker that is cleavable at a pH ranging from 6 to 8. For example, in some embodiments L is a linker that is cleavable at pH 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, or 8.0.

In certain embodiments, L is, at each occurrence, independently a linker that is cleavable at a temperature ranging from 20° C. to 40° C., from 25° C. to 35° C., from 30° C. to 35° C., from 30° C. to 37° C., from 35° C. to 37° C., from 35° C. to 40° C., from 32° C. to 38° C. In certain embodiments, L is, at each occurrence, independently a linker that is cleavable at a temperature of about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C.

In certain embodiments, L is, at each occurrence, independently a linker that is cleavable by an enzyme. For example, in some embodiments, the enzyme is a hydrolase, an oxidoreductase or a lyase. In certain embodiments, the enzyme is an EC 4.1 (e.g., EC 4.1.1, EC 4.1.2, EC 4.1.3 or EC 4.1.99), EC 4.2, EC 4.3, EC4.4, EC 4.5, EC 4.6, or EC 4.99 enzyme.

In certain embodiments, L comprises one of the following structures:

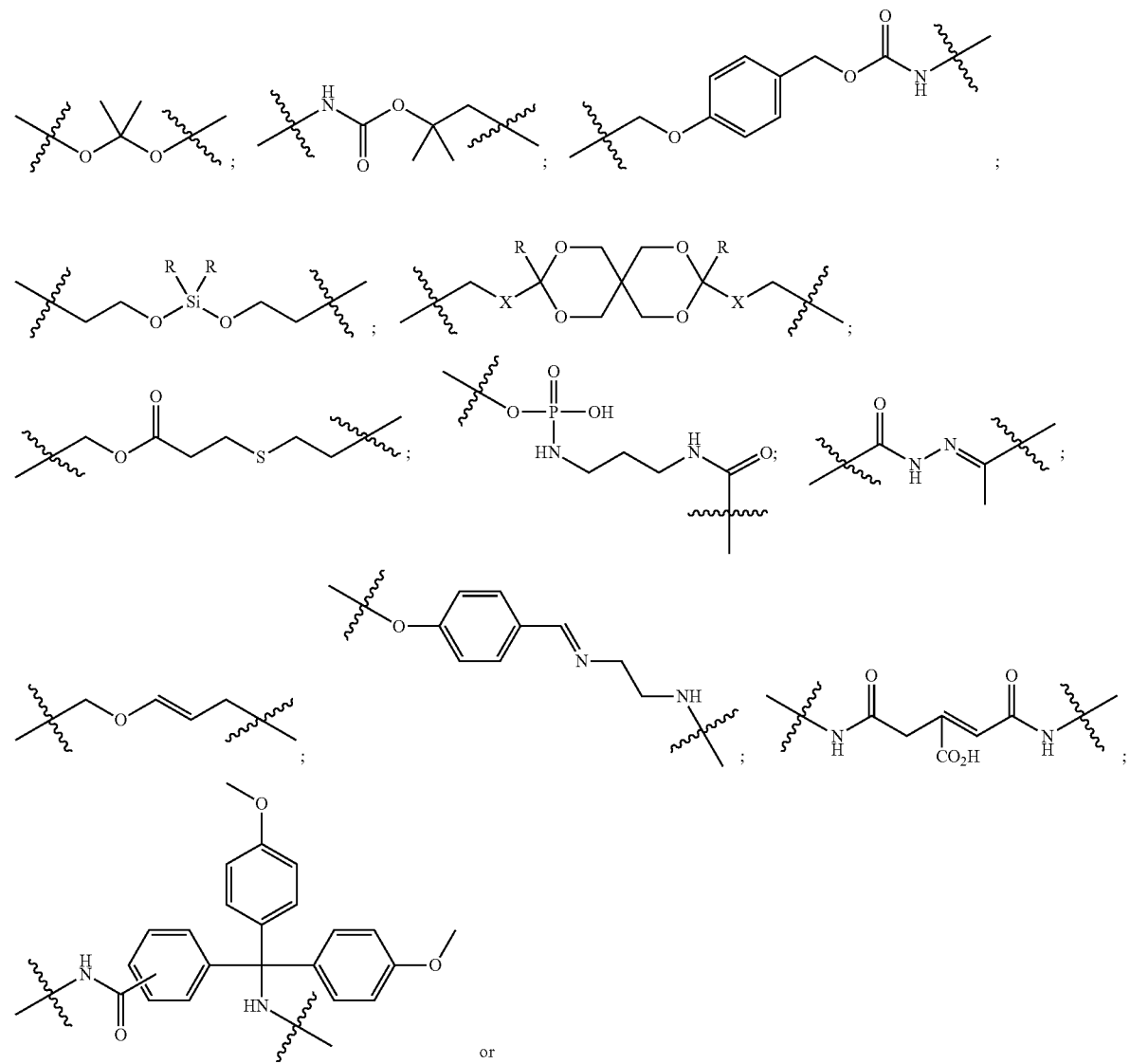

or

-continued

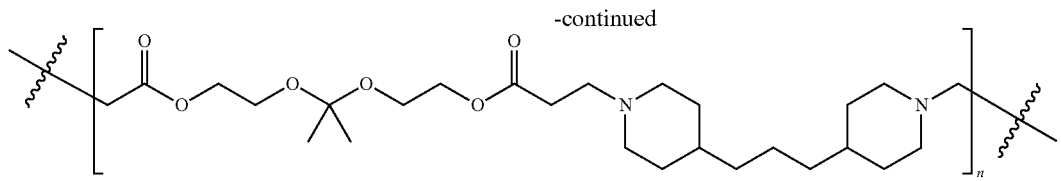

wherein:

R is H, methyl, ethyl, isopropyl, tert-butyl, or phenyl;

X is O or $CH_2$; and n is an integer greater than 0.

In still other embodiments, for at least one occurrence of L, L-M has the following structure:

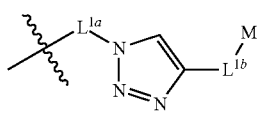

wherein $L^{1a}$ and $L^{1b}$ are each independently optional linkers.

In different embodiments, for at least one occurrence of L, L-M has the following structure:

wherein $L^{1a}$ and $L^{1b}$ are each independently optional linkers.

In various embodiments of the foregoing, $L^{1a}$ or $L^{1b}$, or both, is absent.

In other embodiments, $L^{1a}$ or $L^{1b}$, or both, is present.

In some embodiments $L^{1a}$ and $L^{1b}$, when present, are each independently alkylene or heteroalkylene. For example, in some embodiments $L^{1a}$ and $L^{1b}$, when present, independently have one of the following structures:

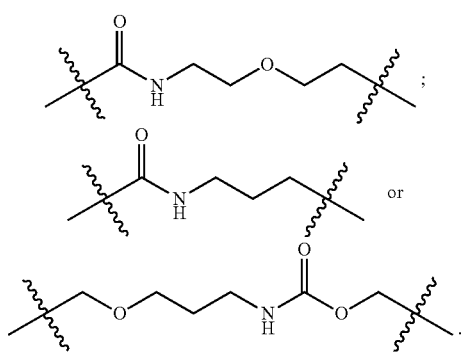

In still other different embodiments of structure (I), L is at each occurrence, independently an optional alkylene or heteroalkylene linker. In certain embodiments, L1 has one of the following structures:

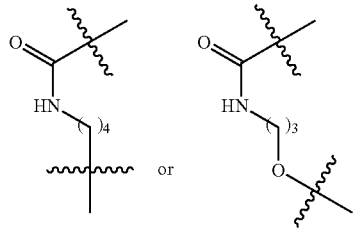

In more embodiments, L2 and L3 are, at each occurrence, independently C1-C6 alkylene, C2-C6 alkenylene or C2-C6 alkynylene. For example, in some embodiments the compound has the following structure (IC):

(IC)

wherein:

$x^1$, $x^2$, $x^3$ and $x^4$ are, at each occurrence, independently an integer from 0 to 6; and z is an integer from 1 to 100.

In certain embodiments of the compound of structure (IC), at least one occurrence of $x^1$, $x^2$, $x^3$ or $x^4$ is 1. In other embodiments, $x^1$, $x^2$, $x^3$ and $x^4$ are each 1 at each occurrence. In other embodiments, $x^1$ and $x^3$ are each 0 at each occurrence. In some embodiments, $x^2$ and $x^4$ are each 1 at each occurrence. In still other embodiments, $x^1$ and $x^3$ are each 0 at each occurrence, and $x^2$ and $x^4$ are each 1 at each occurrence.

In some more specific embodiments of the compound of structure (IC), L comprises a triazolyl functional group. In some other specific embodiments of the compound of structure (IC), L comprises an amide or thiourea functional group. In other embodiments of the compound of structure (IB), L comprises an optional alkylene or heteroalkylene linker.

In some embodiments, $L^4$ is, at each occurrence, independently $C_1$-$C_6$ alkylene or $C_2$-$C_6$ alkynylene. For example, in some embodiments the compound has the structure (ID):

(ID)

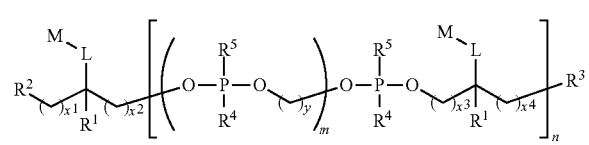

$x^1$, $x^2$, $x^3$ and $x^4$ are, at each occurrence, independently an integer from 0 to 6; and y is an integer from 1 to 6. In some embodiments, y is 1. In some embodiments, y is 2. In some embodiments y is 3, 4, 5, or 6. In certain embodiments, at least one occurrence of $x^1$, $x^2$, $x^3$ or $x^4$ is 1. In more specific embodiments, $x^1$, $x^2$, $x^3$ and $x^4$ are each 1 at each occurrence.

In still other embodiments of any of the compounds of structure (I), $R^4$ is, at each occurrence, independently OH, O or $OR_d$. It is understood that "$OR_d$" and "$SR_d$" are intended to refer to O and S associated with a cation. For example, the disodium salt of a phosphate group may be represented as:

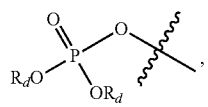

where $R_d$ is sodium ($Na^+$).

In other embodiments of any of the compounds of structure (I), $R^5$ is, at each occurrence, oxo.

In some different embodiments of any of the foregoing compounds, $R^1$ is, at each occurrence, H.

In other various embodiments, $R^2$ and $R^3$ are each independently OH or $-OP(=R_a)(R_b)R_c$. In some different embodiments, $R^2$ or $R^3$ is OH or $-OP(=R_a)(R_b)R_c$, and the other of $R^2$ or $R^3$ is Q or a linker comprising a covalent bond to Q.

In still more different embodiments of any of the foregoing compounds of structure (I), $R^2$ and $R^3$ are each independently $-OP(=R_a)(R_b)R_c$. In some of these embodiments, $R_c$ is OL'. In some more specific embodiments, L' is a targeting moiety or a linker to a targeting moiety. In related embodiments, L' is a linker to a targeting moiety, the linker comprising an alkylene oxide or phosphodiester moiety, or combinations thereof.

In other embodiments, $R^2$ and $R^3$ are each independently $-OP(=R_a)(R_b)OL'$, and L' is an alkylene or heteroalkylene linker to: Q, a targeting moiety, an analyte (e.g., analyte molecule), a solid support, a solid support residue, a nucleoside or a further compound of structure (I).

The linker L' can be any linker suitable for attaching Q, a targeting moiety, an analyte (e.g., analyte molecule), a solid support, a solid support residue, a nucleoside or a further compound of structure (I) to the compound of structure (I). Advantageously certain embodiments include use of L' moieties selected to increase or optimize water solubility of the compound. In certain embodiments, L' is a heteroalkylene moiety. In some other certain embodiments, L' comprises an alkylene oxide or phosphodiester moiety, or combinations thereof.

In certain embodiments, L' has the following structure:

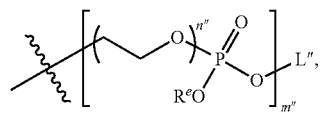

wherein:

m" and n" are independently an integer from 1 to 10;

$R^e$ is H, an electron pair or a counter ion;

L" is the targeting moiety or a linkage to the targeting moiety.

In some embodiments, m" is an integer from 4 to 10, for example 4, 6 or 10. In other embodiments n" is an integer from 3 to 6, for example 3, 4, 5 or 6.

In certain embodiments, the targeting moiety is an antibody or cell surface receptor antagonist. In related embodiments, the antibody or cell surface receptor antagonist is an epidermal growth factor receptor (EGFR) inhibitor, a hepatocyte growth factor receptor (HGFR) inhibitor, an insulin-like growth factor receptor (IGFR) inhibitor, a folate, or a MET inhibitor. In certain embodiments, the antibody or cell surface receptor antagonist is a tyrosine kinase inhibitor (e.g., gefitinib, erlotinib), lapatinib, Vandetanib, neratinib, osimertinib, Tovantinib (ARQ197), Crizotinib, Cabozantinib, tyrphostins (e.g., AG538, AG1024), pyrrolo(2,3-d)-pyrimidine derivatives (e.g., NVP-AEW541), monoclonal antibody (e.g., figitumumab, cetuximab, panitumumab, necitumumab, ganitumab, cixutumumab, dalotuzumab, robatumumab, onartuzumab, K1, labetuzumab, milatuzumab, lorvotuzumab, inotuzumab), BMS-777607, PF-02341066, PF-04217903, AMG-458, MK-2461, JNJ-38877605, GSK 1363089 (foretinib), XL880, XL 184, ARQ197, E7050, or INCB28060.

In certain embodiments, the antibody or cell surface receptor antagonist targets EGFR (e.g., EGFRvIII), HER 2, folate receptors, CD19, CD20, CD22, CD27L, CD30, CD33, CD37, CD56, CD66e, CD70, CD74, CD79b, CA6, CD138, CA 6, mesothelin, nectin 4, STEAPI, MUC16, MaPi2b, GCC, Trop-2, AGS-5, ENPP3, carbonic anhydrase IX, GPNMB, PDMA, In some other embodiments, L" is an alkylene or heteroalkylene moiety.

In some other certain embodiments, L" comprises an alkylene oxide, phosphodiester moiety, sulfhydryl, disulfide or maleimide moiety or combinations thereof.

In other more specific embodiments of any of the foregoing compounds of structure (I), $R^2$ or $R^3$ has one of the following structures:

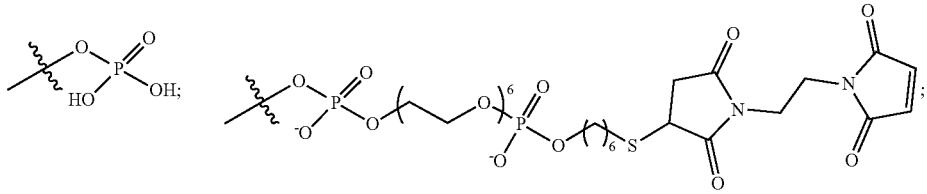

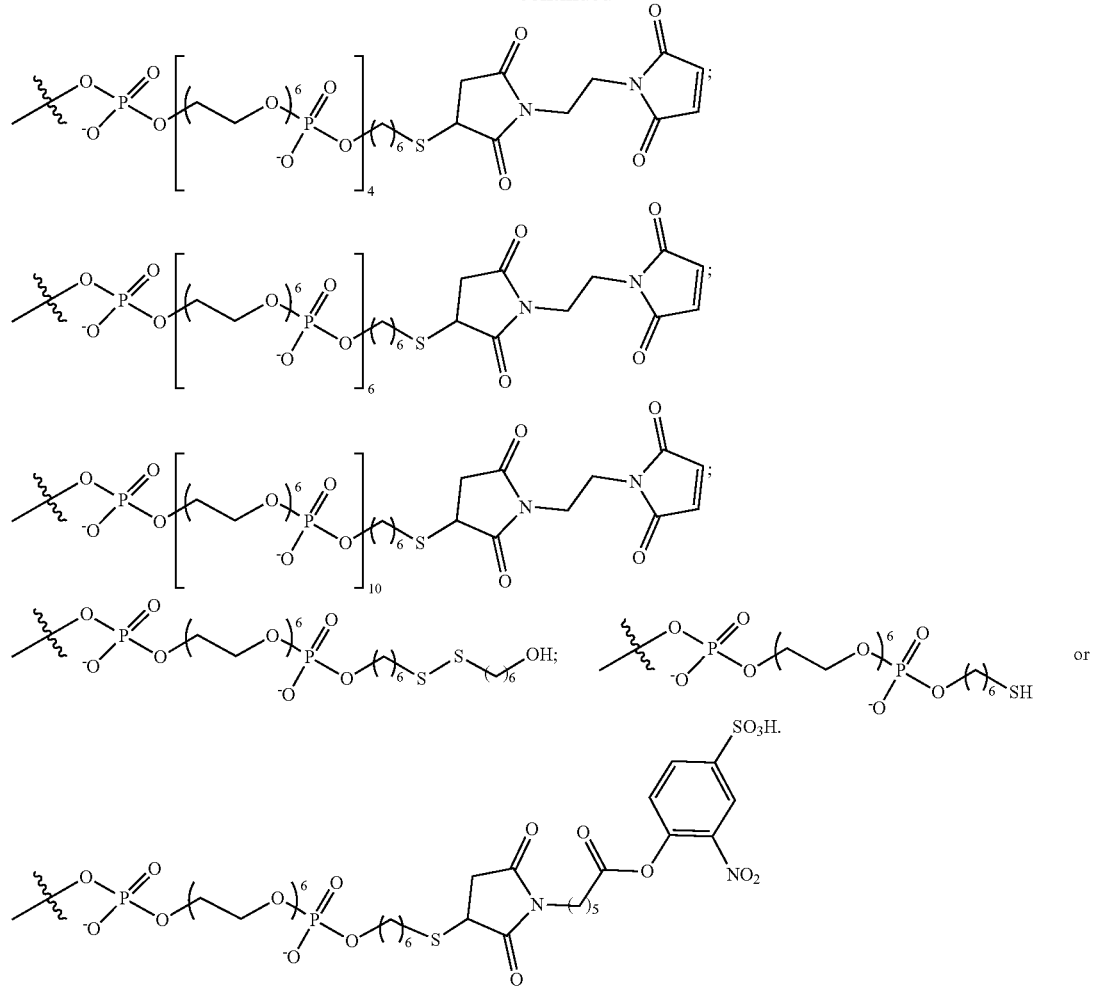

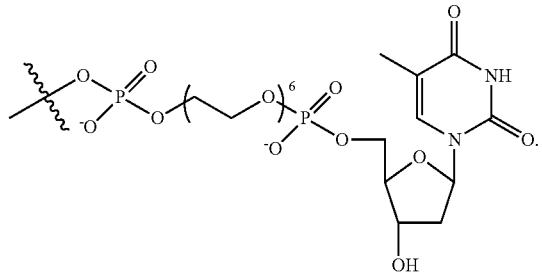

One of skill in the art will understand that the dT group depicted above is included for ease of synthesis and economic efficiencies only, and is not required. Other solid supports can be used and would result in a different nucleoside or solid support residue being present on L', or the nucleoside or solid support residue can be removed or modified post synthesis.

Certain embodiments of compounds of structure (I) can be prepared according to solid-phase synthetic methods analogous to those known in the art for preparation of oligonucleotides. Accordingly, in some embodiments, L' is a linkage to a solid support, a solid support residue or a nucleoside. Solid supports comprising an activated deoxythymidine (dT) group are readily available, and in some embodiments can be employed as starting material for preparation of compounds of structure (I). Accordingly, in some embodiments $R^2$ or $R^3$ has the following structure:

In still other embodiments, Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (I) (e.g., in the $R^2$ or $R^3$ position), and Q and Q' comprise complementary reactive groups such that reaction of the compound of structure (I) and the further compound of structure (I) results in covalently bound dimer of the compound of structure (I). Multimer compounds of structure (I) can also be prepared in an analogous manner and are included within the scope of embodiments of the invention.

The type of Q group and connectivity of the Q group to the remainder of the compound of structure (I) is not limited, provided that Q comprises a moiety having appropriate reactivity for forming the desired bond.

In certain embodiments, Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (I) comprise Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

The Q groups can be conveniently provided in protected form to increase storage stability or other desired properties, and then the protecting group removed at the appropriate time for coupling with, for example, a targeting moiety or analyte. Accordingly, Q groups include "protected forms" of a reactive group, including any of the reactive groups described above and in the Table 1 below. A "protected form" of Q refers to a moiety having lower reactivity under predetermined reaction conditions relative to Q, but which can be converted to Q under conditions, which preferably do not degrade or react with other portions of the compound of structure (I). One of skill in the art can derive appropriate protected forms of Q based on the particular Q and desired end use and storage conditions. For example, when Q is SH, a protected form of Q includes a disulfide, which can be reduce to reveal the SH moiety using commonly known techniques and reagents.

Exemplary Q moieties are provided in Table I below.

TABLE 1

| Exemplary Q Moieties | |
|---|---|
| Structure | Class |
| [structure] —SH | Sulfhydryl |
| [structure] —N=C=S | Isothiocyanate |
| [structure with O-CH3, NH2+Cl-] | Imidoester |
| [structure with O, N=N+=N-] | Acyl Azide |
| [pentafluorophenyl ester structure] | Activated Ester |
| [tetrafluorophenyl ester structure] | Activated Ester |
| [sulfo-nitrophenyl ester structure, SO3-, NO2] | Activated Ester |
| [thiosuccinimide linked sulfo-nitrophenyl ester] | Activated Ester |
| [NHS ester structure] | Activated Ester |
| [sulfo-NHS ester structure, SO3-] | Activated Ester |
| [structure: S(=O)2-X], X = halo | Sulfonyl halide |
| [maleimide structure] | Maleimide |
| [thiosuccinimide-ethyl-maleimide structure] | Maleimide |

TABLE 1-continued

Exemplary Q Moieties

| Structure | Class |
|---|---|
| 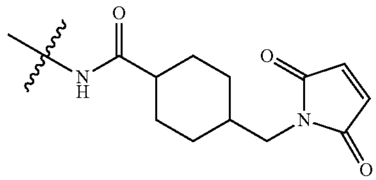 [SMILES: *NC(=O)C1CCC(CN2C(=O)C=CC2=O)CC1] | Maleimide |
| X = halo | α-haloimide |
| 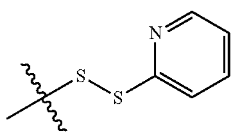 [SMILES: *SSc1ccccn1] | Disulfide |
| 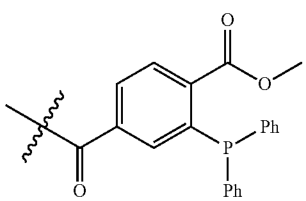 [SMILES: *C(=O)c1ccc(C(=O)OC)c(P(c2ccccc2)c2ccccc2)c1] | Phosphine |
| 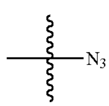 | Azide |
| 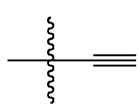 | Alkyne |
| 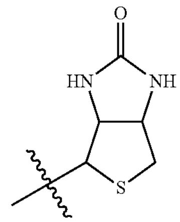 [SMILES: *C1SCC2NC(=O)NC21] | Biotin |
| 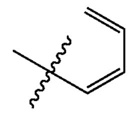 [SMILES: */C=C\C=C] | Diene |
| | Alkene/dienophile |
| EWG = electron withdrawing group | Alkene/dienophile |
| —NH$_2$ | Amino |

It should be noted that in some embodiments, wherein Q is SH, the SH moiety will tend to form disulfide bonds with another sulfhydryl group, for example on another compound of structure (I). Accordingly, some embodiments include compounds of structure (I), which are in the form of disulfide dimers, the disulfide bond being derived from SH Q groups.

Also included within the scope of certain embodiments are compounds of structure (I), wherein one, or both, of $R^2$ and $R^3$ comprises a linkage to a further compound of structure (I). For example, wherein one or both of $R^2$ and $R^3$ are —OP(=$R_a$)($R_b$)$R_c$, and $R_c$ is OL′, and L′ is a linker comprising a covalent bond to a further compound of structure (I). Such compounds can be prepared by preparing a first compound of structure (I) having for example about 10 "M" moieties (i.e., n=9) and having an appropriate "Q" for reaction with a complementary Q′ group on a second compound of structure (I). In this manner, compounds of structure (I), having any number of "M" moieties, for example 100 or more, can be prepared without the need for sequentially coupling each monomer. Exemplary embodiments of such compounds of structure (I) have the following structure (I′)

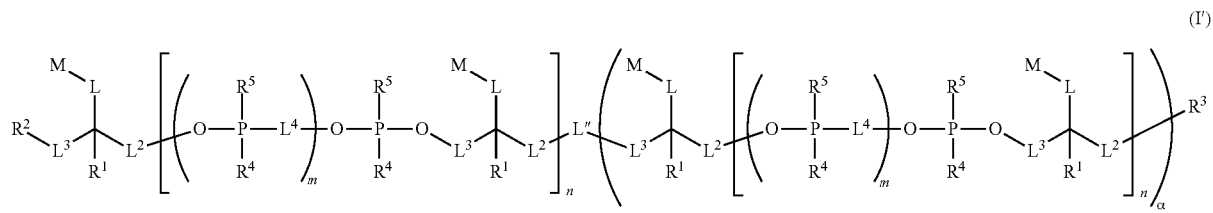

(I′)

wherein:
each occurrence of $R^1$, $R^2$, $R^3$, $R^4$, $R^5$, L, $L^2$, $L^3$, $L^4$, M, m and n are independently as defined for a compound of structure (I);

L" is a linker comprising a functional group resulting from reaction of a Q moiety with a corresponding Q' moiety; and α is an integer greater than 1, for example from 1 to 100, or 1 to 10.

Other compounds of structure (I') are derivable by those of ordinary skill in the art, for example by dimerizing or polymerizing compounds of structure (I) provided herein.

In other embodiments, the Q moiety is conveniently masked (e.g., protected) as a disulfide moiety, which can later be reduced to provide an activated Q moiety for binding to a desired targeting moiety. For example, the Q moiety may be masked as a disulfide having the following structure:

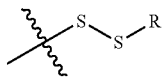

wherein R is an optionally substituted alkyl group. For example, in some embodiments, Q is provided as a disulfide moiety having the following structure:

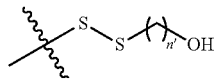

wherein n' is an integer from 1 to 10, for example 6.

In some other embodiments, one of $R^2$ or $R^3$ is OH or $-OP(=R_a)(R_b)R_c$, and the other of $R^2$ or $R^3$ is a linker comprising a covalent bond to a targeting moiety or a linker comprising a covalent bond to a solid support. For example, in some embodiments the targeting moiety is an antibody or cell surface receptor antagonist. In still different embodiments, the solid support is a polymeric bead or nonpolymeric bead.

The value for m is another variable that can be selected based on the desired solubility, permeation effect or therapeutic application. In some embodiments, m is, at each occurrence, independently an integer from 1 to 10. In other embodiments, m is, at each occurrence, independently an integer from 1 to 5, for example 1, 2, 3, 4 or 5.

In other embodiments, m is, at each occurrence, independently an integer greater than 2, and z is an integer from 3 to 10, for example in some embodiment m is, at each occurrence, independently an integer greater than 2, such as 3, 4, 5 or 6, and z is an integer from 3 to 6.

The solubility, permeation or retention can also be tuned by selection of different values of n. In certain embodiments, n is an integer from 1 to 100. In other embodiments, n is an integer from 1 to 10. In some embodiments n is 1. In some embodiments n is 2. In some embodiments n is 3. In some embodiments n is 4. In some embodiments n is 5. In some embodiments n is 6. In some embodiments n is 7. In some embodiments n is 8. In some embodiments n is 9. In some embodiments n is 10.

Tumor cell antigens include tumor-specific antigens and tumor-associated antigens, for example EGFR, HER 2, folate receptors, CD20, CD33, oncofetal antigens (e.g., alphafetoprotein, carcinoembryonic antigen, immature laminin receptor, TAG-72), CA-125, MUC-1, epithelial tumor antigen, tyrosinase, melanoma-associated antigen (MAGE), and abnormal products of RAS or p53. Tumor cell antigens may also include antigens characterized as oncofetal, oncoviral (e.g., HPV E6, E7), overexpressed/accumulated (e.g., BING-4, calcium activated chloride channel 2, 9D7, Ep-CAM, EphA3, HER2, telomerase, mesothelin, SAP-1, survivin), cancer-tetis (e.g., BAGE family, CAGE family, GAGE family, MAGE family, SAGE family, XAGE family), lineage-restricted, mutated, post-translationally altered, idiotypic, CT9 or CT10 (e.g., NY-ESO-1/LAGE-1, PRAME).

In some embodiments, M is at each occurrence, independently an NSAID, a kinase inhibitor, an anthracycline, and EGFR inhibitor or an alkylating agent.

In some embodiments, the biologically active moiety is an anti-cancer drug. In certain specific embodiments, M is at each occurrence, independently an anti-cancer drug, and the targeting moiety is an antibody specific for a tumor cell antigen. Anti-cancer drug, as used herein, includes derivatives. That is, and anti-cancer drug that has been modified or derivatized such that the drug can be conjugated or attached to another molecule (e.g., to include Q moieties). For example, maytansine is a cancer drug and maytansinoids are cancer drug derivatives.

In certain embodiments, the anti-cancer drug is an epidermal growth factor receptor (EGFR) inhibitor, phosphatidylinositol kinase (PI3K) inhibitor, insulin-like growth factor receptor (IGF1R) inhibitor, Janus kinase (JAK) inhibitor, a Met kinase inhibitor, a SRC family kinase inhibitor, a mitogen-activated protein kinase (MEK) inhibitor, an extracellular-signal-regulated kinase (ERK) inhibitor, a topoisomerase inhibitors (such as irinotecan, or such as etoposide, or such asdoxorubicin), taxanes (such as anti-microtubule agents including paclitaxel and docetaxel), anti-metabolite agents (such as 5-FU or such as gemcitabine), alkylating agents (such as cisplatin or such as cyclophosphamide), or a taxane.

Anti-cancer drugs that can be modified and incorporated into embodiments of compounds of the present disclosure include, for example, auristatin F; auristatin E; maytansine; calicheamicin; paclitaxel; doxorubicin; cryptophycin; erlotinib; CC-1065; carzelesin; SJG-136; DSB-120; afatinib; Iressa; methotrexate; DNA methylation agents (e.g., procarbazine, temozolomide, dacarbazine, N-methylo-N-nitrourea, N-methyl-N'-nitro-N-nitroguanine, and the like).

Other non-limiting examples of anti-cancer drugs include Gleevec® (Imatinib Mesylate), Velcade® (bortezomib), Casodex (bicalutamide), Iressa® (gefitinib), and Adriamycin, alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex®, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins or capecitabine. Also included as suitable cancer drugs are anti-hormonal agents that act to regulate or inhibit hormone action on tumors such as anti-estrogens including for example tamoxifen, (Nolvadexm), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomeRASe inhibitor RFS 2000; difluoromethylornithine (DMFO).

Where desired, embodiments of the compounds or composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

M is selected based on the desired therapeutic and/or optical properties, for example based on treating a specific disease or condition (e.g., cancer) or producing a particular color and/or fluorescence emission wavelength. In some embodiments, M is the same at each occurrence; however, it is important to note that each occurrence of M need not be an identical M, and certain embodiments include compounds wherein M is not the same at each occurrence. For example, in some embodiments, each M is not the same and the different M moieties are selected to have different therapeutic properties (e.g., cytotoxic and anti-inflammatory). In some embodiments, each M is not the same and the different M moieties are selected to have the same or similar therapeutic properties (e.g., cytotoxicity). In certain embodiments, each M is independently selected from the following:

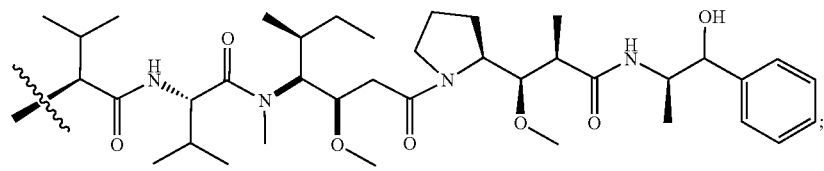

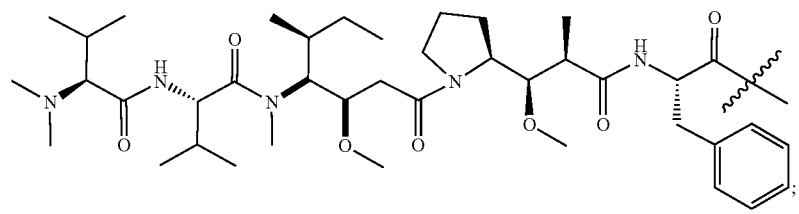

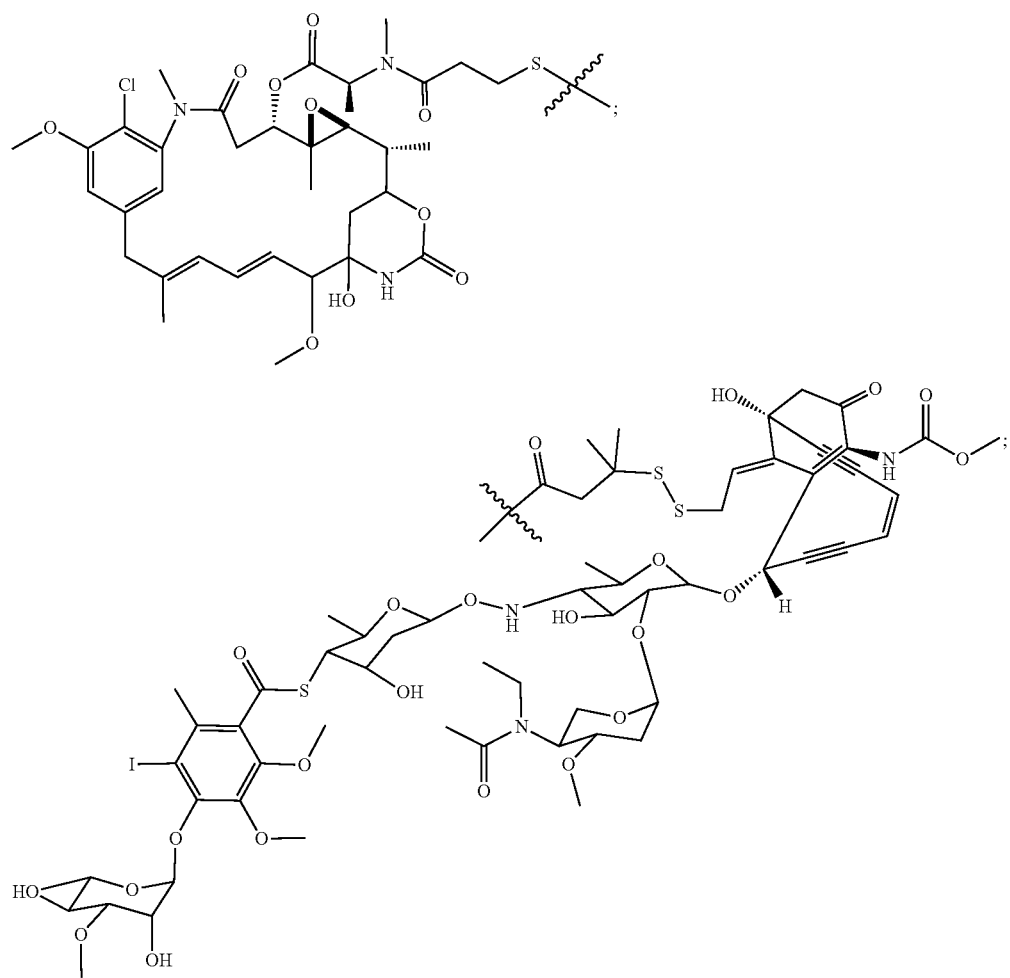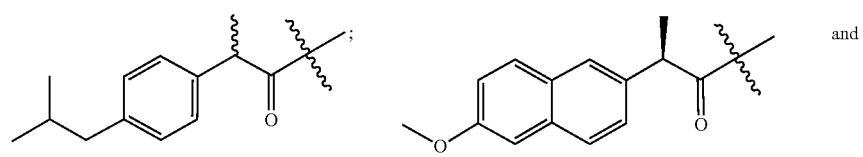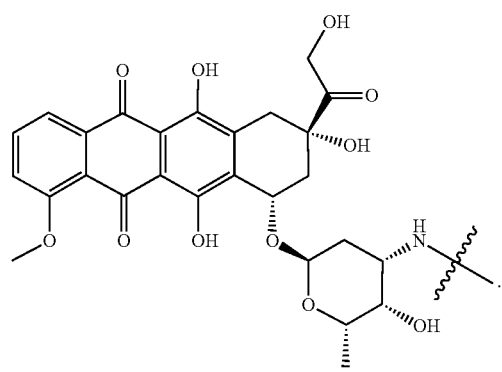

Although depicted having specific points of attachment (i.e., ⚡ with the remainder of the molecule for ease of illustration, the M moiety may be attached via any available point. One of skill in the art can determine an appropriate attachment point.
In certain embodiments, L-M has one of the following structures:
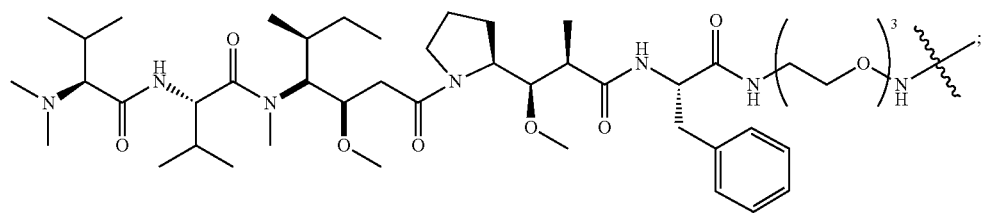
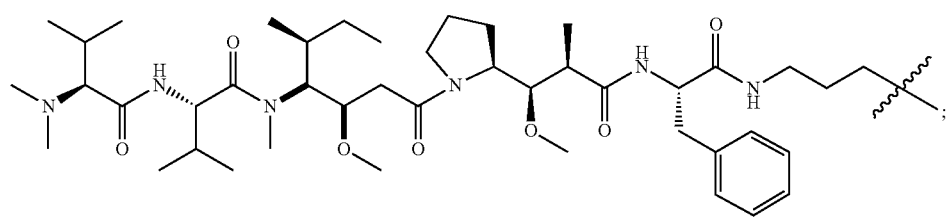
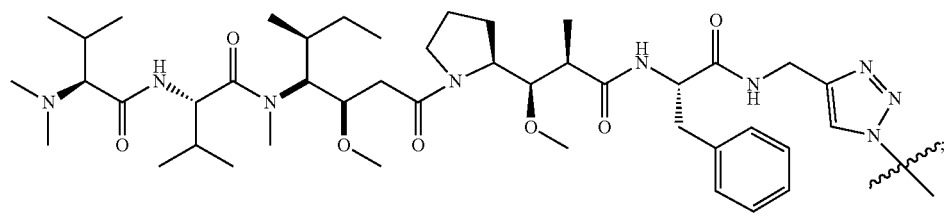
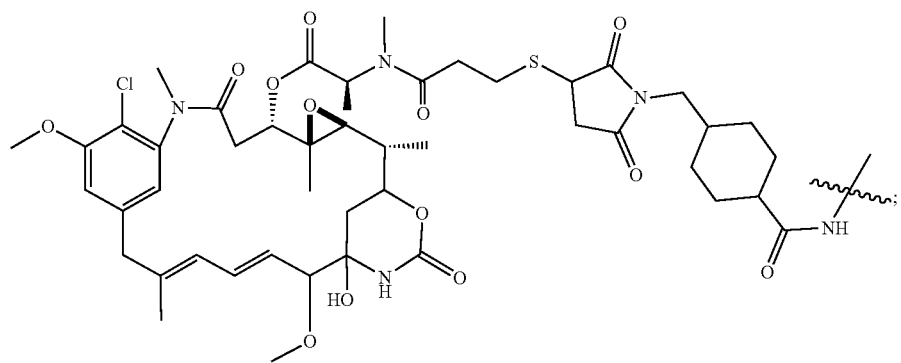

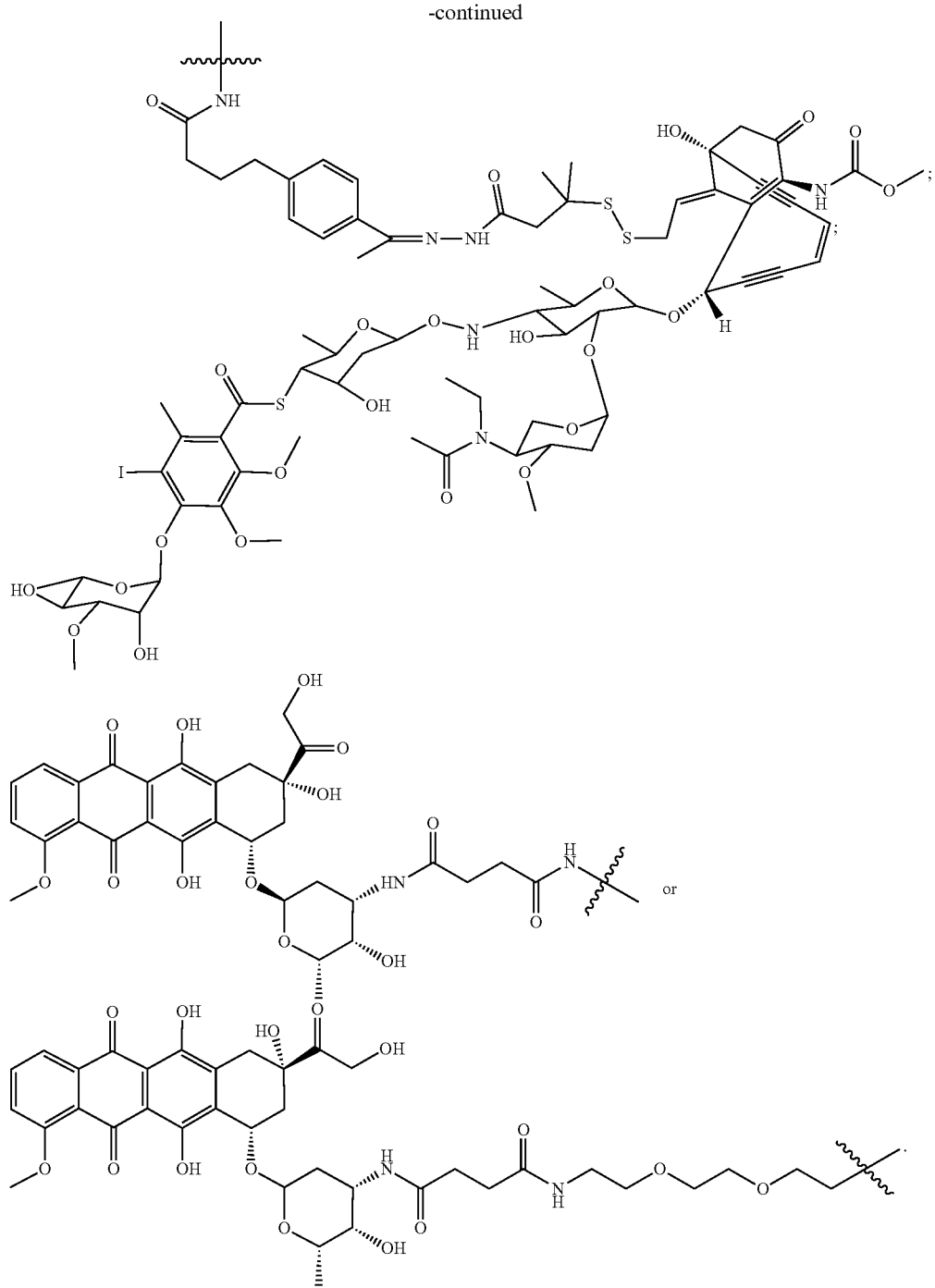

In still more embodiments of any of the foregoing, M is the same. In other embodiments, each M is different. In still more embodiments, one or more M is the same and one or more M is different.

In some embodiments selected occurrences of M are not the same and the different M moieties are selected to have absorbance and/or emissions for use in fluorescence resonance energy transfer (FRET) methods. For example, in such embodiments the different M moieties are selected such that absorbance of radiation at one wavelength causes emission of radiation at a different wavelength by a FRET mechanism. Exemplary M moieties can be appropriately selected by one of ordinary skill in the art based on the desired end use. Exemplary M moieties for FRET methods include fluorescein and 5-TAMRA (5-carboxytetramethyl-rhodamine, succinimidyl ester) dyes.

M may be attached to the remainder of the molecule from any position (i.e., atom) on M. One of skill in the art will recognize means for attaching M to the remainder of molecule. Exemplary methods include the "click" reactions described herein.

In some embodiments, M is a fluorescent or colored moiety. Any fluorescent and/or colored moiety may be used, for examples those known in the art and typically employed in colorimetric, UV, and/or fluorescent assays may be used. Examples of M moieties which are useful in various embodiments of the invention include, but are not limited to: Xanthene derivatives (e.g., fluorescein, rhodamine, Oregon green, eosin or Texas red); Cyanine derivatives (e.g., cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary M moieties include: Cyanine dyes, xanthate dyes (e.g., Hex, Vic, Nedd, Joe or Tet); Yakima yellow; Redmond red; tamra; texas red and alexa Fluor® dyes.

In still other embodiments of any of the foregoing, M comprises three or more aryl or heteroaryl rings, or combinations thereof, for example four or more aryl or heteroaryl rings, or combinations thereof, or even five or more aryl or heteroaryl rings, or combinations thereof. In some embodiments, M comprises six aryl or heteroaryl rings, or combinations thereof. In further embodiments, the rings are fused. For example in some embodiments, M comprises three or more fused rings, four or more fused rings, five or more fused rings, or even six or more fused rings.

In some embodiments, M is cyclic. For example, in some embodiments M is carbocyclic. In other embodiment, M is heterocyclic. In still other embodiments of the foregoing, M, at each occurrence, independently comprises an aryl moiety. In some of these embodiments, the aryl moiety is multicyclic. In other more specific examples, the aryl moiety is a fused-multicyclic aryl moiety, for example which may comprise at least 3, at least 4, or even more than 4 aryl rings.

In other embodiments of any of the foregoing compounds of structure (I), (IA), (IB), (IC), (ID) or (I'), M comprises at least one heteroatom. For example, in some embodiments, the heteroatom is nitrogen, oxygen or sulfur.

In still more embodiments of any of the foregoing, M comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, M is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety. In other embodiments, M is p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, M is a coumarin dye, resorufin dye, dipyrrometheneboron difluoride dye, ruthenium bipyridyl dye, energy transfer dye, thiazole orange dye, polymethine or N-aryl-1,8-naphthalimide dye.

In some embodiments, M is pyrene, perylene, perylene monoimide or 6-FAM or a derivative thereof. In some other embodiments, M has one of the following structures:

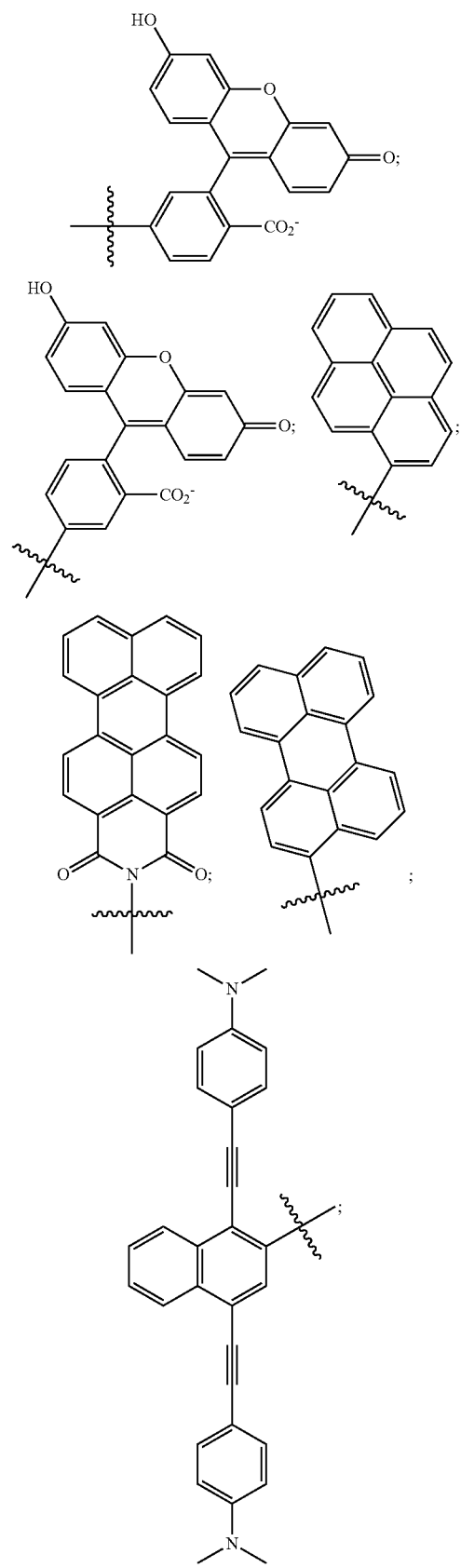

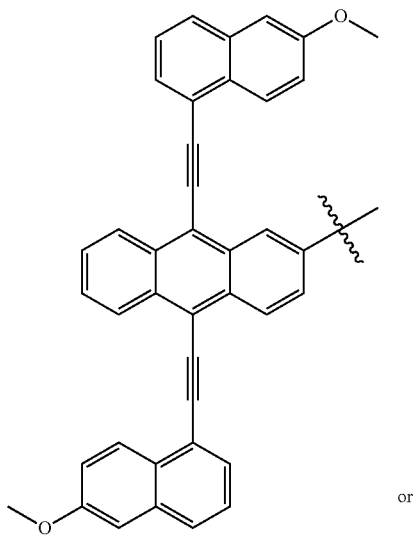

or

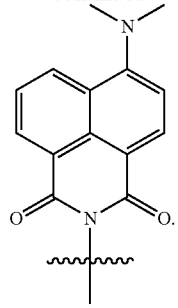

Although M moieties comprising carboxylic acid groups are depicted in the anionic form ($CO_2^-$) above, one of skill in the art will understand that this will vary depending on pH, and the protonated form ($CO_2H$) is included in various embodiments.

In some specific embodiments, the compound is a compound selected from Table 2. In some embodiments, the compound is a compound selected from Table 3. In some embodiments, the compound is a compound selected from Table 4. The compounds in Table 2 were prepared according to the procedures set forth in the Examples and their identity confirmed by mass spectrometry.

TABLE 2

Exemplary Compounds of Structure I

| Cpd. | Structure | MW Found Calc. |
|---|---|---|
| 1 | 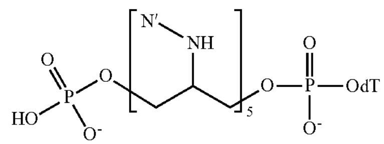 | 2068.9 / 2068.4 |
| 2 | 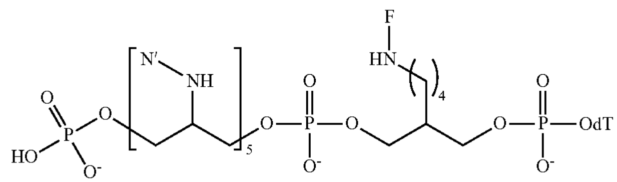 | 2636.4 / 2636.3 |
| 3 | | 2564.5 / 2588.7 |

TABLE 2-continued
Exemplary Compounds of Structure I
| Cpd. | Structure | MW Found Calc. |
|---|---|---|
| 4 | 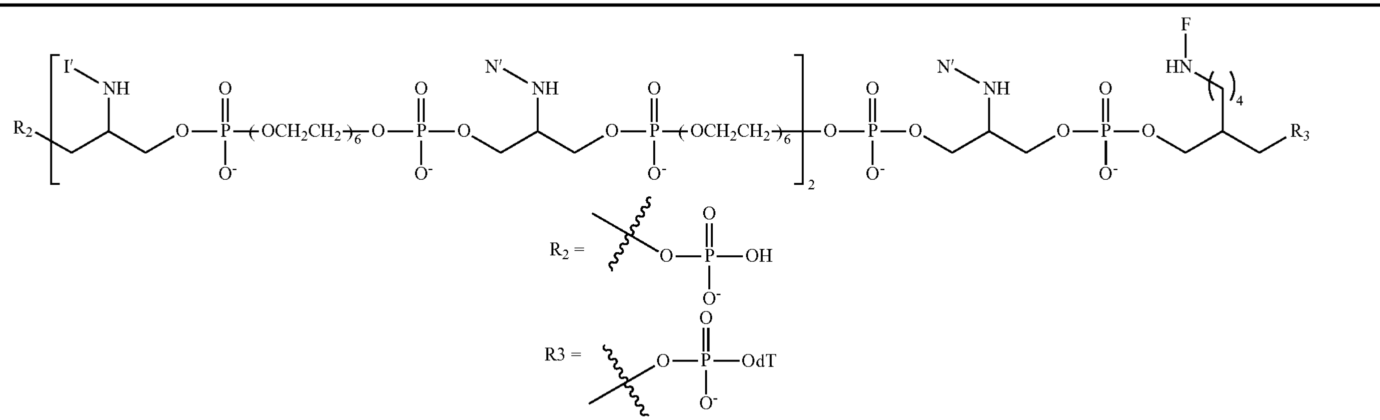 | 4286.0 4286.3 |
| 5 | 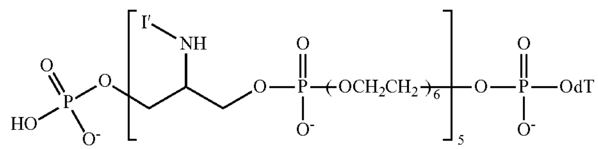 | 3670.5 3670.4 |
| 6 | 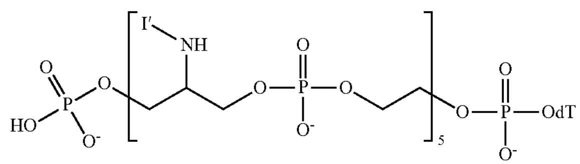 | 2569.3 2569.1 |
| 7 | 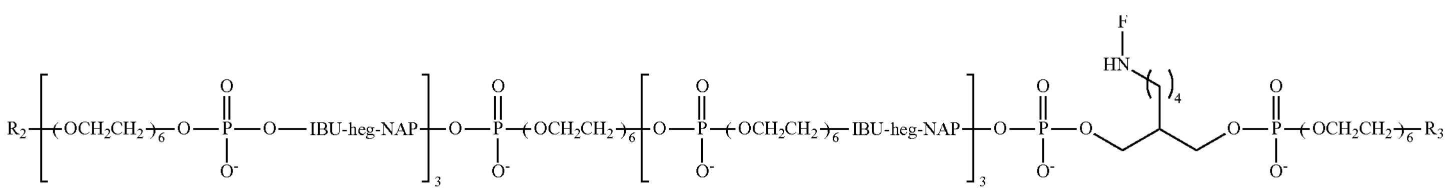 | 8803.2 8801.3 |
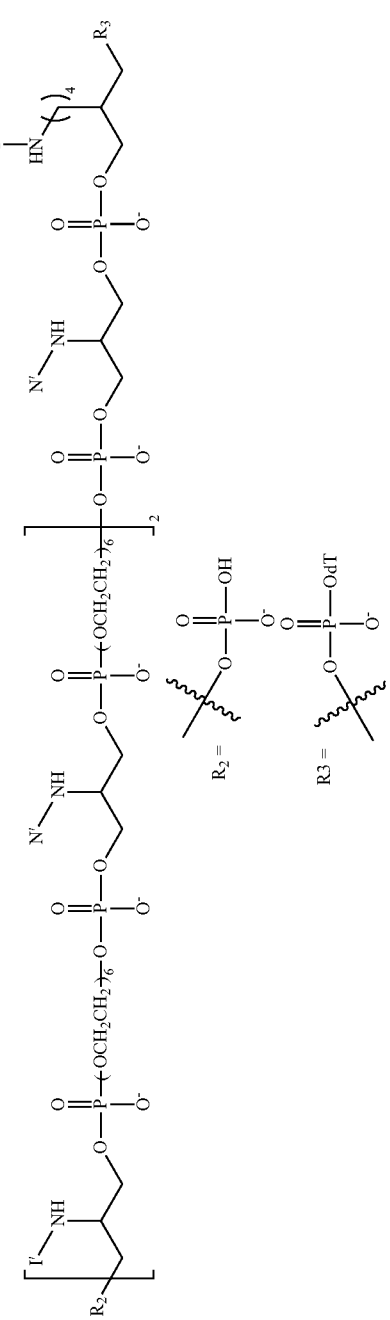

TABLE 2-continued

Exemplary Compounds of Structure I

| Cpd. | Structure | MW Found Calc. |
|---|---|---|
| 8 | 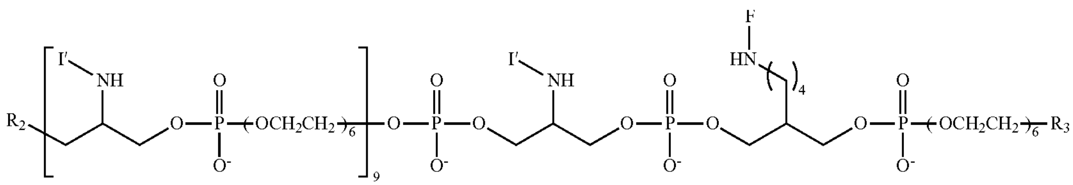 | 8339.0 8340.9 |
| 9 | 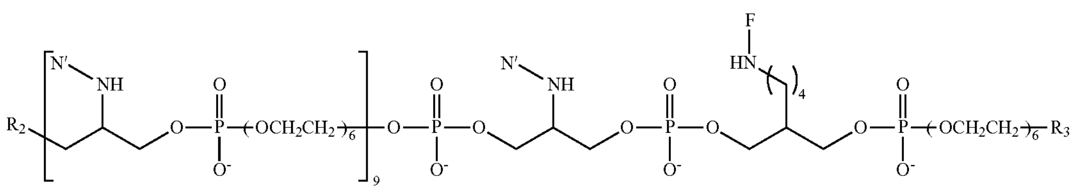 | 8578.8 8580.3 |

TABLE 2-continued
Exemplary Compounds of Structure I
| Cpd. | Structure | MW Found Calc. |
|---|---|---|
| 10 | 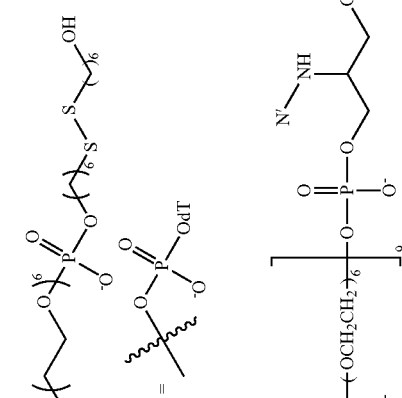 | 4982.6 4980.0 |
| 11 | 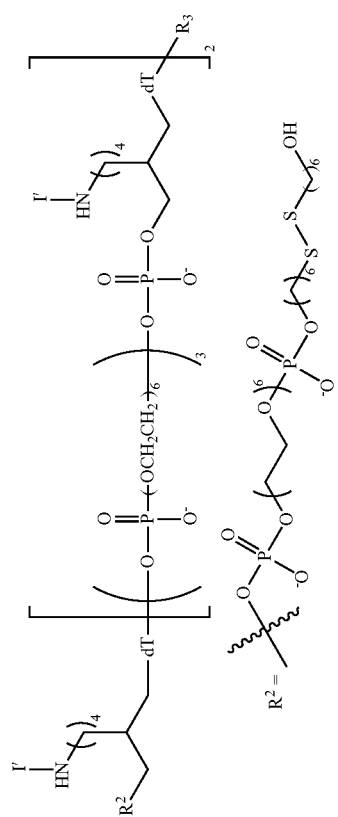 | Found 4523.6 |

TABLE 2-continued
Exemplary Compounds of Structure I
| Cpd. | Structure | MW Found Calc. |
|---|---|---|
| 12 | 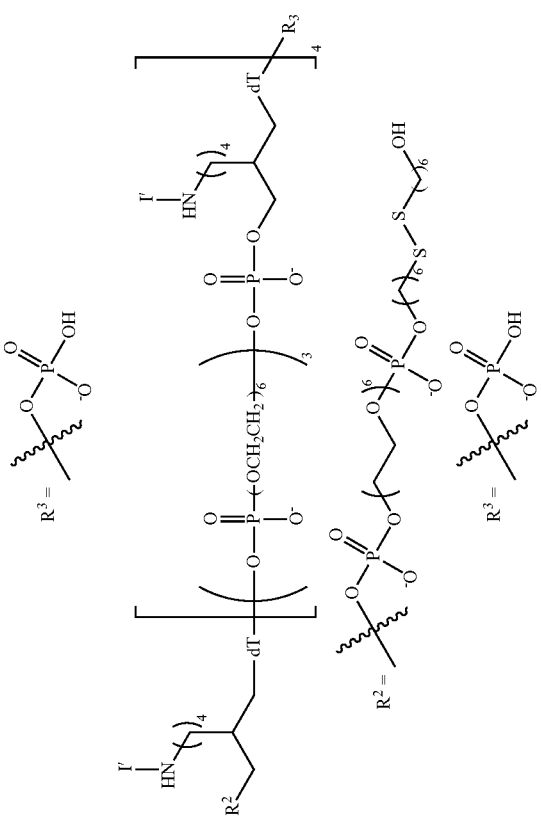 | TBD |
| 13 | 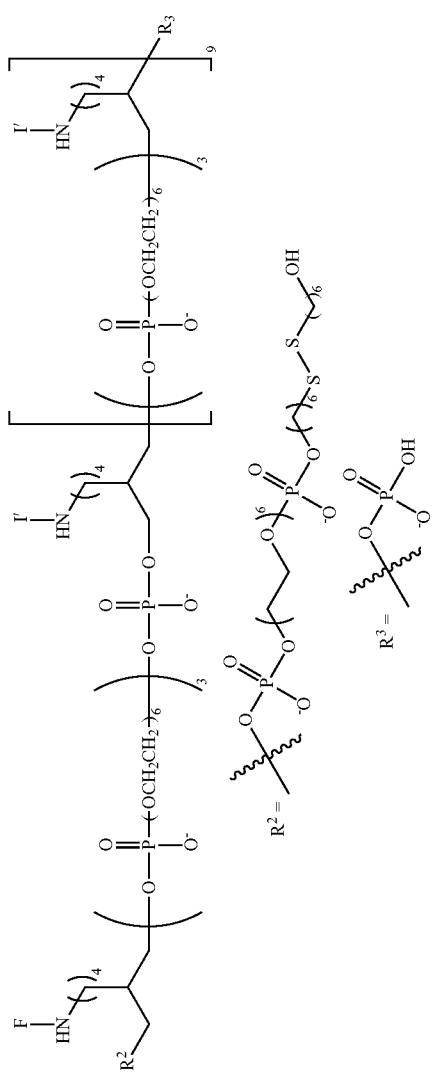 | TBD |

TABLE 2-continued
Exemplary Compounds of Structure I
| Cpd. | Structure | MW Found Calc. |
|---|---|---|
| 14 | 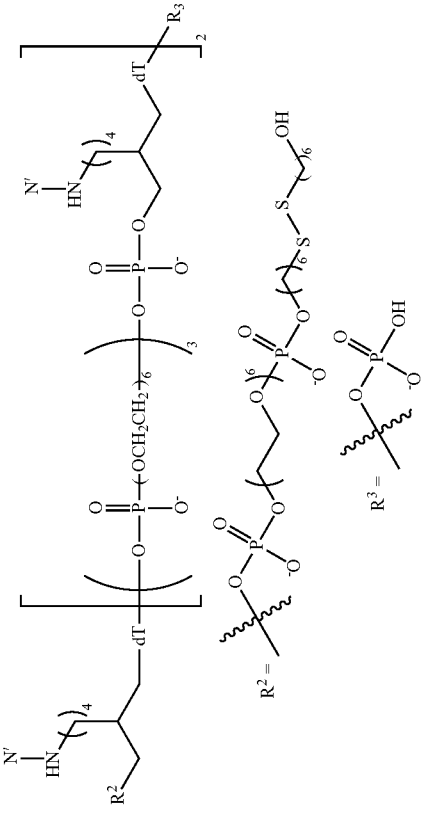 | Found 4595.7 |
| 15 | 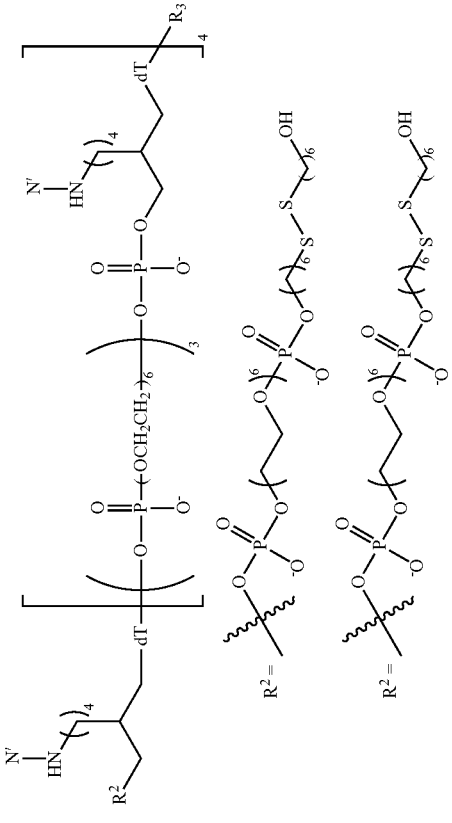 | TBD |

TABLE 2-continued

Exemplary Compounds of Structure I

| Cpd. | Structure | MW Found Calc. |
|---|---|---|
| 16 | 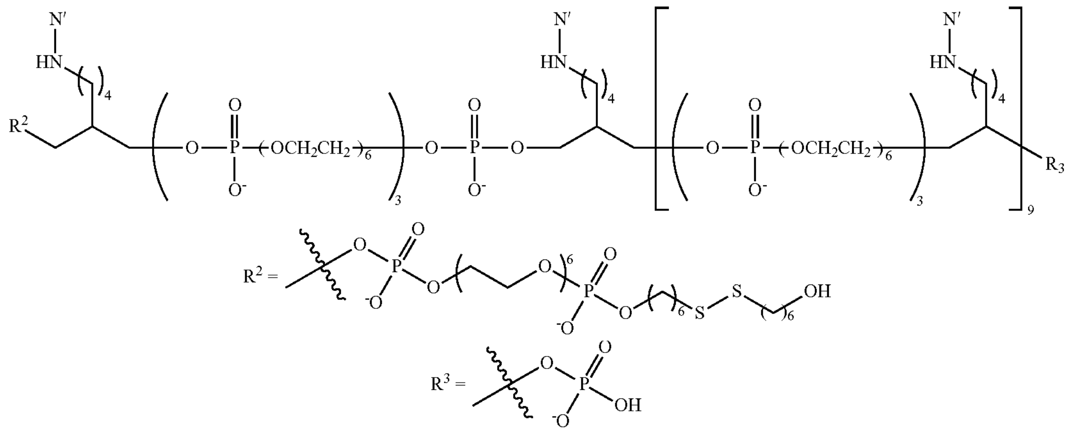 | TBD |
| 17 | 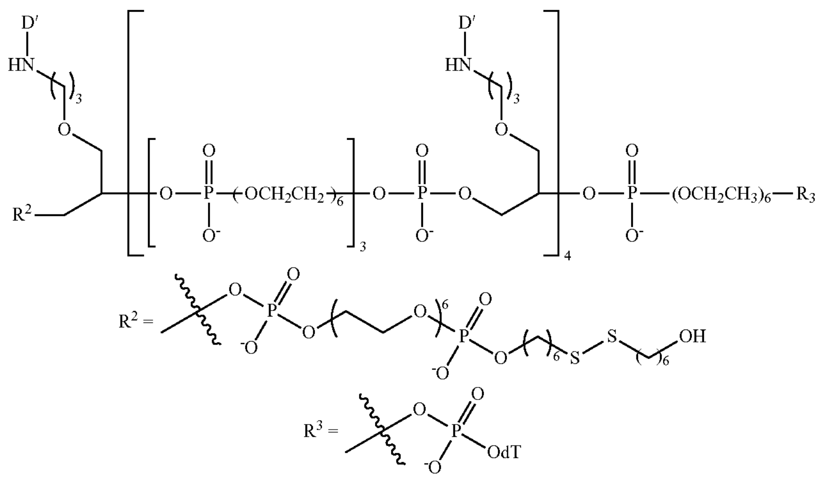 | 6425 |

TABLE 2-continued

Exemplary Compounds of Structure I

| Cpd. | Structure | MW Found Calc. |
|---|---|---|
| 18 | 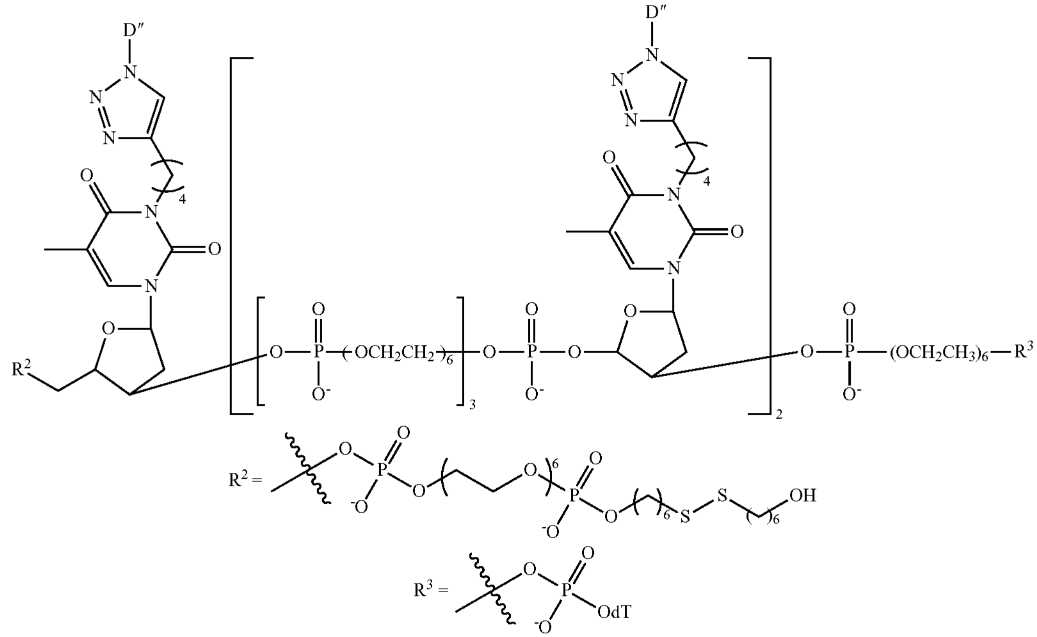 | 6878.0 6878.7 |
| 19† | 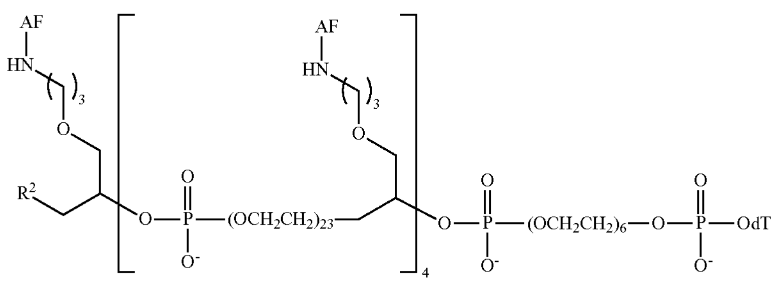 | — |

TABLE 2-continued
Exemplary Compounds of Structure I
| Cpd. | Structure | MW Found Calc. |
|---|---|---|
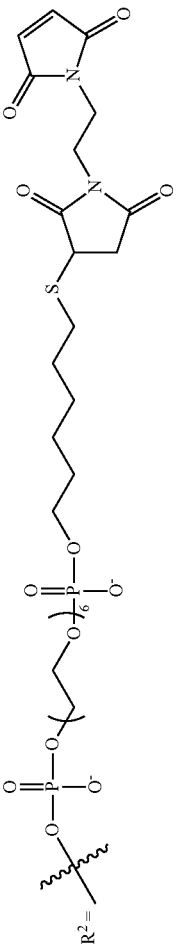
†Structure is shown as having 23 ethylene glycol repeat units, but actual structure may vary with respect to the number of ethylene glycol repeat units (e.g., about 21, 22, 23, 24, 25, 26 ethylene glycol repeat units)
*TBD = to be determined

TABLE 3

Exemplary Compounds of Structure I

| Compound | Structure |
|---|---|
| III-1 | 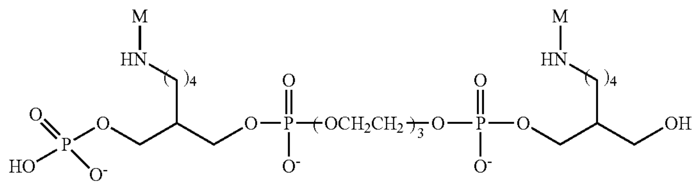 |
| III-2 | 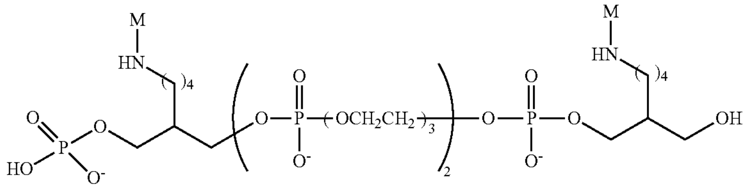 |
| III-3 | 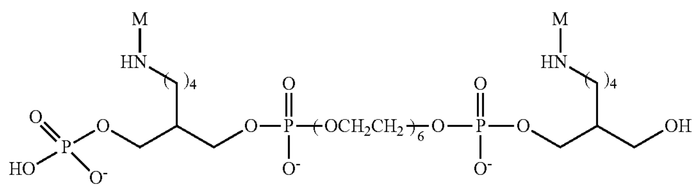 |
| III-4 | 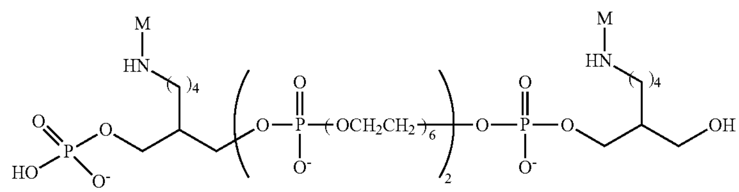 |
| III-5 | 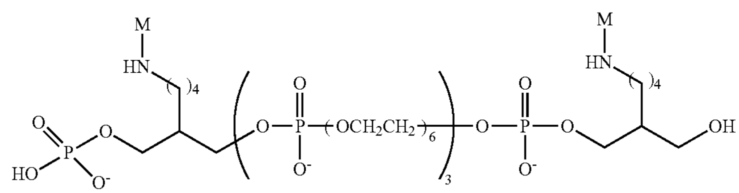 |
| III-6 | 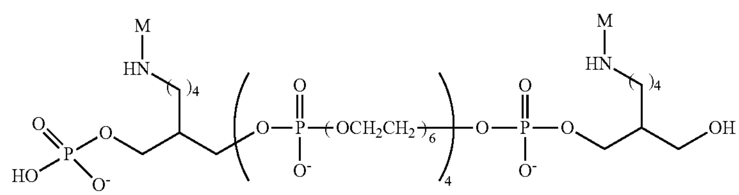 |
| III-7 | 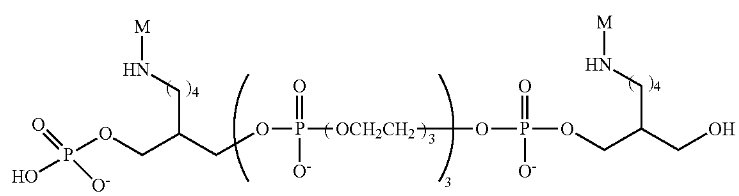 |
| III-8 | 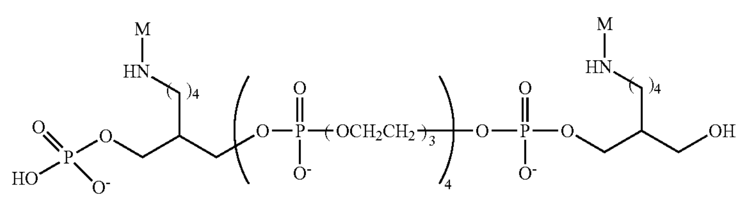 |

TABLE 3-continued
Exemplary Compounds of Structure I
| Compound | Structure |
|---|---|
| III-9 | 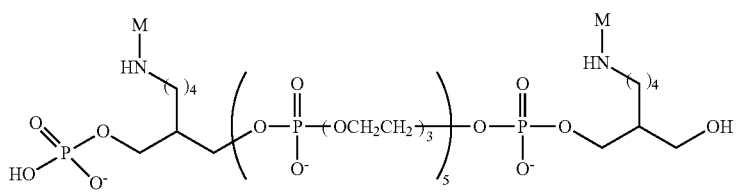 |
| III-10 | 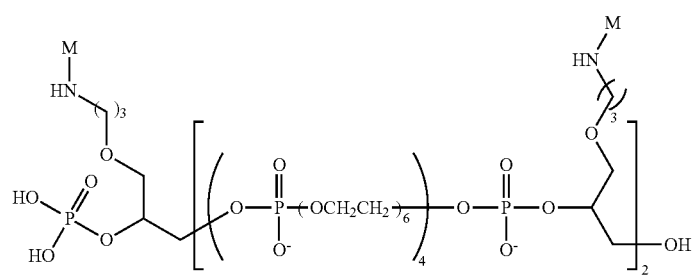 |
| III-11 | 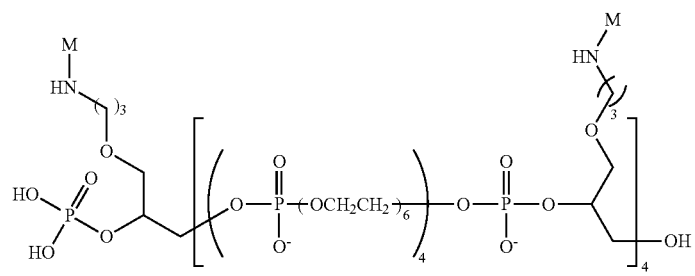 |
| III-12 | 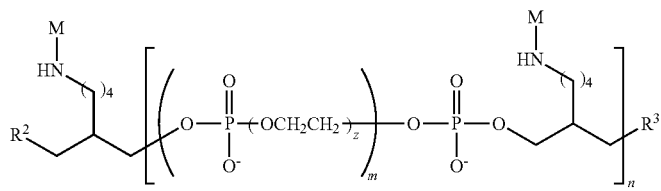
$z = 3, 4, 5$ or $6$
$m = 2, 3, 4$ or $5$
$n = 1\text{-}10$ |
| III-13 | 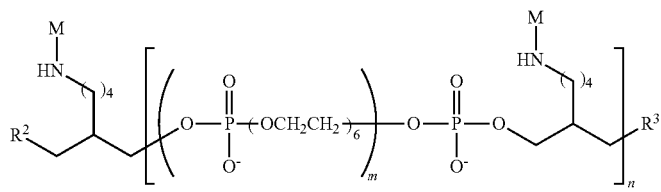 |
| III-14 | 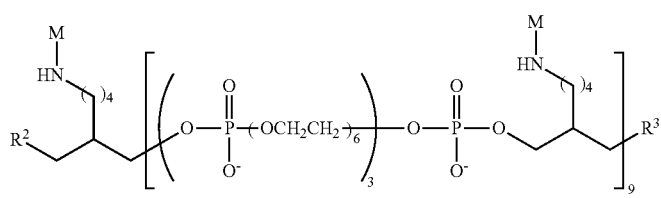 |

TABLE 3-continued
Exemplary Compounds of Structure I
| Compound | Structure |
|---|---|
| III-15 | 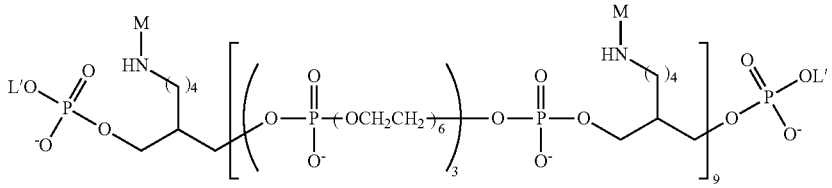 |
| III-16 | 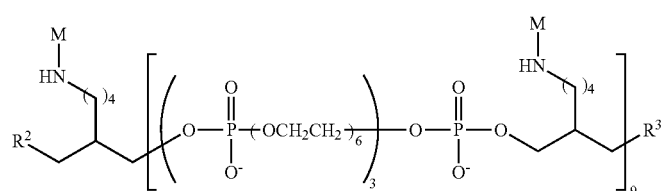 |
| III-17 | 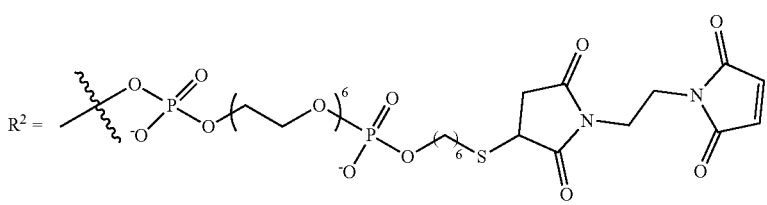 |
| III-18 | 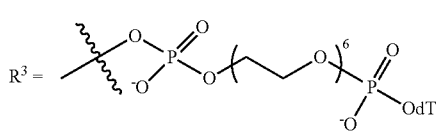 |

TABLE 3-continued

Exemplary Compounds of Structure I

| Compound | Structure |
|---|---|

III-19

III-20

A = antibody

III-21

TABLE 3-continued

Exemplary Compounds of Structure I

| Compound | Structure |
|---|---|

[Structure showing R² group with phosphate-PEG-phosphate-thiosuccinimide-maleimide]

m″ = 4 (I-21A)
m″ = 10 (I-21B)

[Structure showing R³ group with phosphate-PEG-phosphate-OdT]

III-22

[Structure showing the main backbone with M-HN groups, phosphate linkages, OCH₂CH₂ repeats, and R² / R³ substituents]

[Structure showing R² group with phosphate-PEG-phosphate-thiosuccinimide-succinimide-A]

m″ = 4 or 10
A = antibody

[Structure showing R³ group with phosphate-PEG-phosphate-OdT]

III-23

[Structure showing the main backbone with M-HN groups, phosphate linkages, OCH₂CH₂ repeats, and R² / R³ substituents]

[Structure showing R² group with phosphate-PEG-phosphate-SH]

m″ = 4 or 10

[Structure showing R³ group with phosphate-PEG-phosphate-OdT]

TABLE 3-continued

Exemplary Compounds of Structure I

| Compound | Structure |
|---|---|
| III-24 | (chemical structure) |
| III-25 | (chemical structure) |
| III-26† | (chemical structure) |

TABLE 3-continued

Exemplary Compounds of Structure I

| Compound | Structure |
|---|---|

III-27†

III-28†

A = antibody

III-29†

TABLE 3-continued

Exemplary Compounds of Structure I

| Compound | Structure |
|---|---|

III-30†

III-31 m″ = 4 or 10

TABLE 3-continued

Exemplary Compounds of Structure I

| Compound | Structure |
|---|---|
| III-32† | 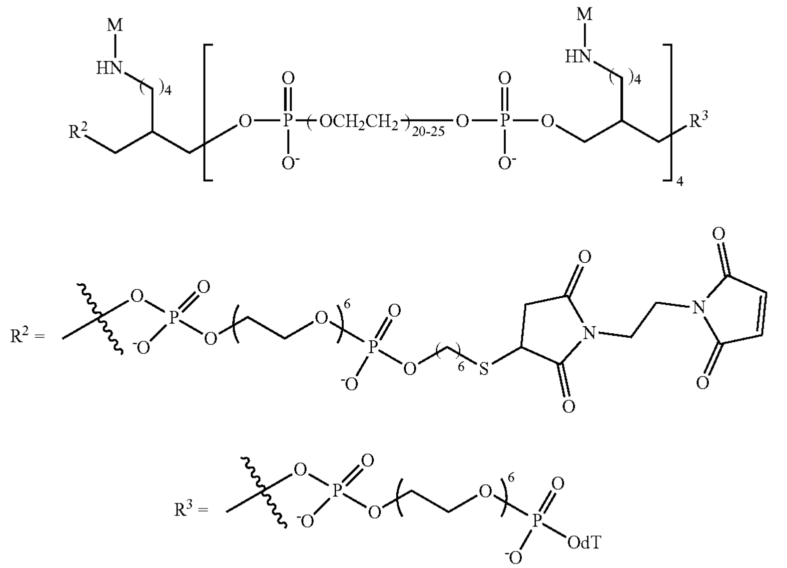 |
| III-33† | 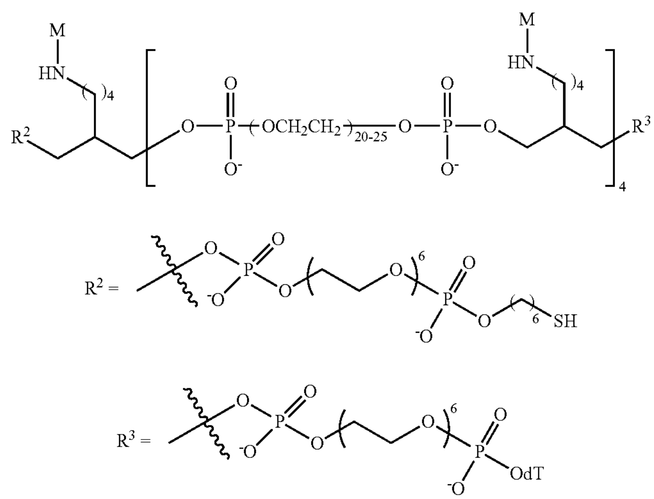 |
| III-34† | 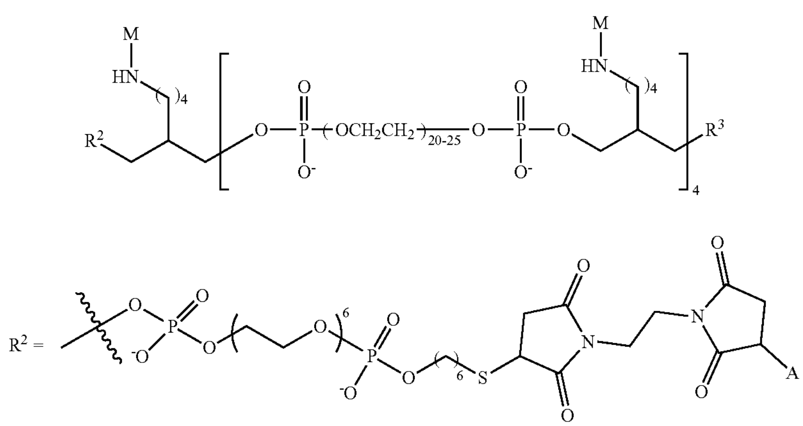 |

A = antibody

TABLE 3-continued

Exemplary Compounds of Structure I

| Compound | Structure |
|---|---|

III-35[†]

III-36[†]

III-37

TABLE 3-continued
Exemplary Compounds of Structure I
| Compound | Structure |
|---|---|
| | 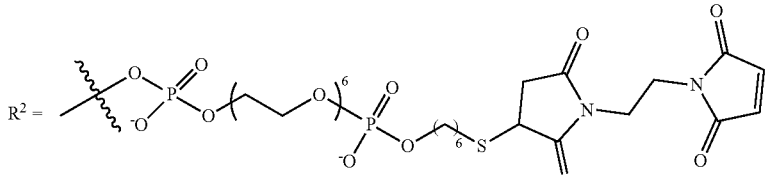 |
| III-38 | 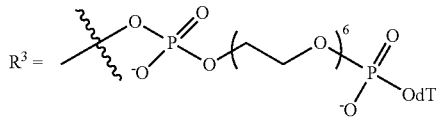<br>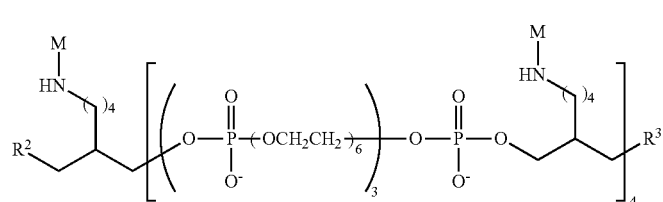 |
| III-39 | 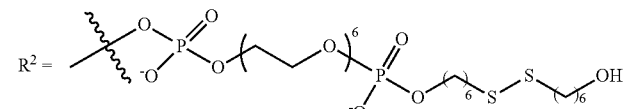<br>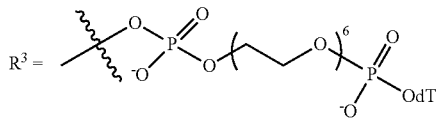 |
| III-40 | 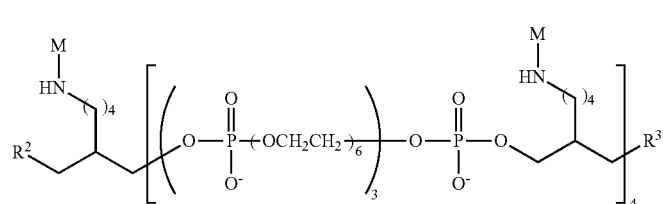 |

TABLE 3-continued

Exemplary Compounds of Structure I

| Compound | Structure |
|---|---|

A = antibody

III-41

III-42

TABLE 3-continued
Exemplary Compounds of Structure I
| Compound | Structure |
| --- | --- |
| III-43 | 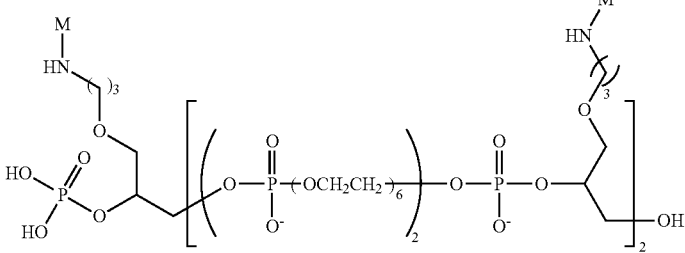 |
| III-44 | 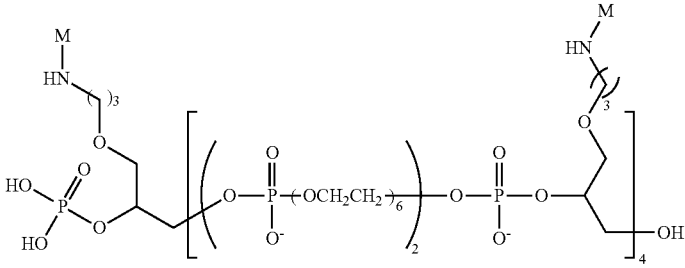 |
| III-45 | 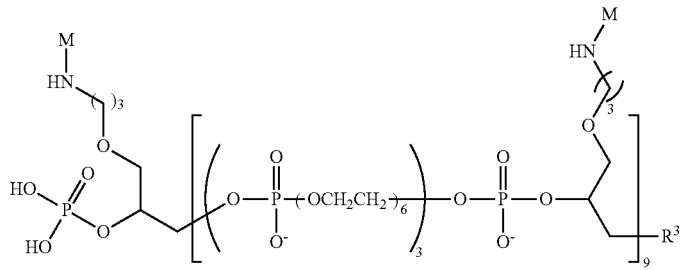 |
| III-46 | 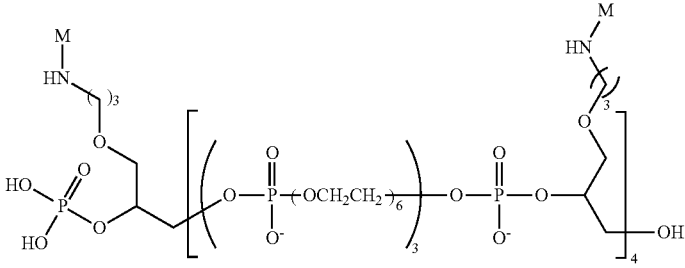 |
| III-47 | 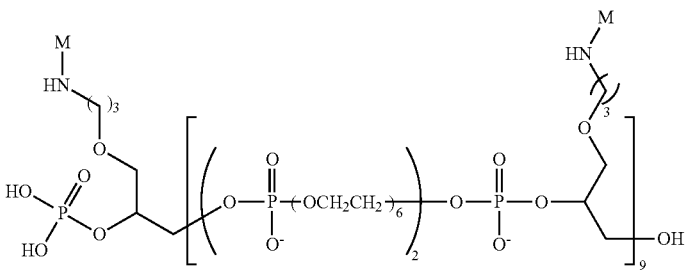 |

TABLE 3-continued

Exemplary Compounds of Structure I

| Compound | Structure |
|---|---|
| III-48 | 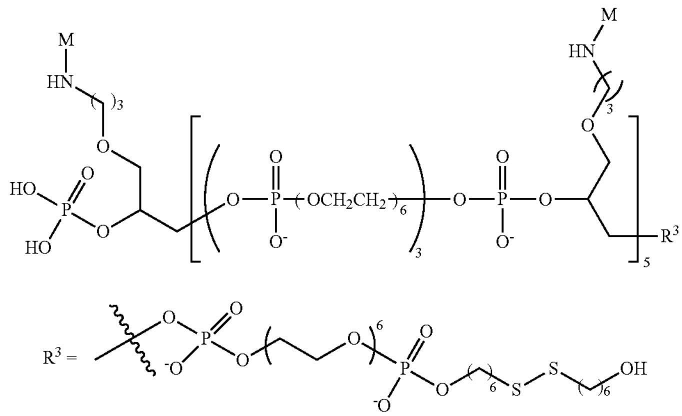 |
| III-49 | 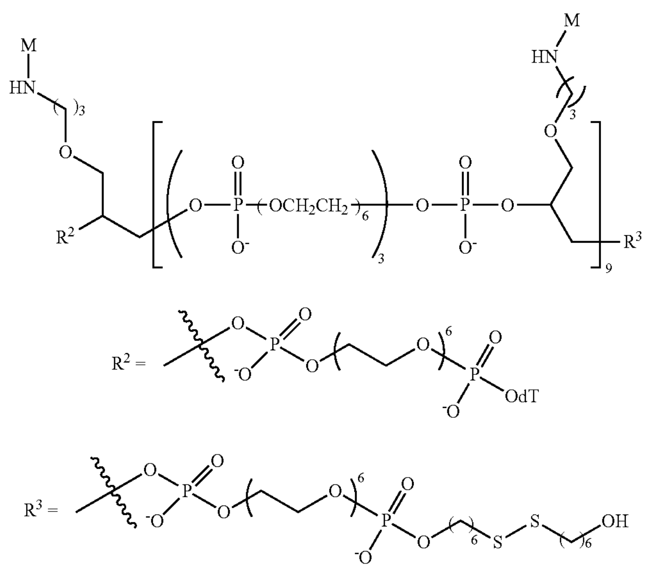 |
| III-50 | 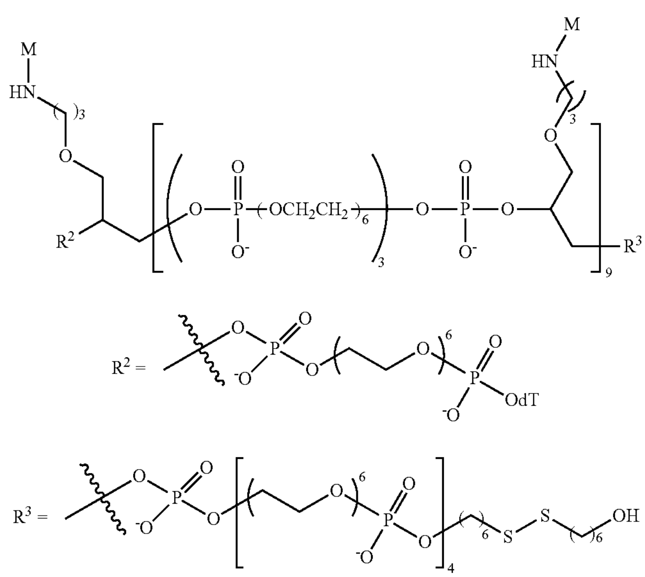 |

TABLE 3-continued
Exemplary Compounds of Structure I
| Compound | Structure |
|---|---|
| III-51 | 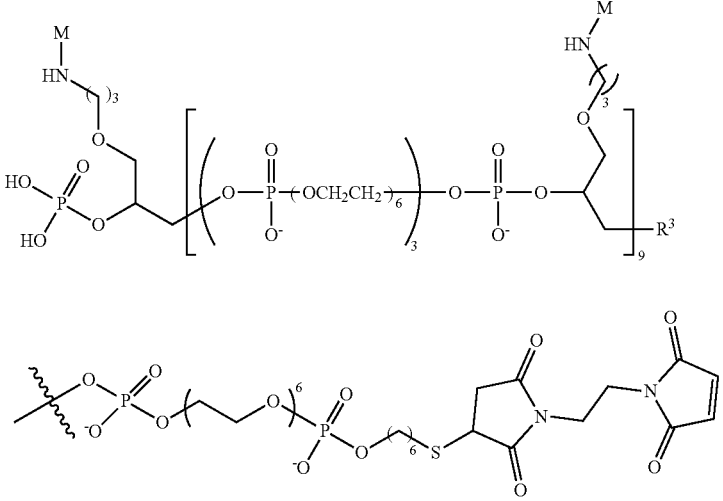 |
| III-52 | 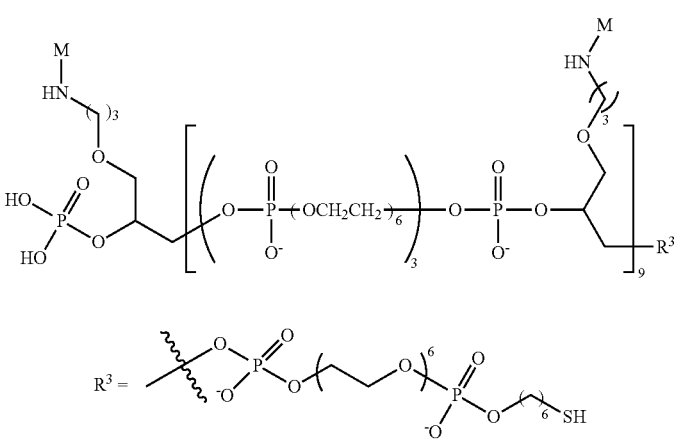 |
| III-53 | 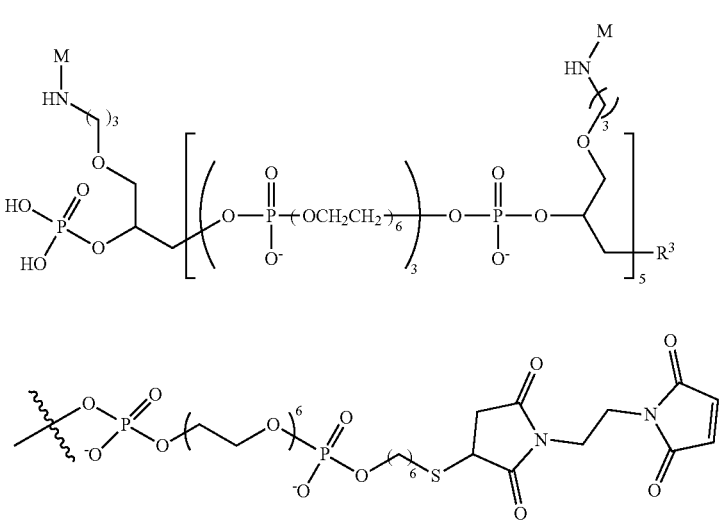 |

TABLE 3-continued
Exemplary Compounds of Structure I
| Compound | Structure |
|---|---|
| III-54 | 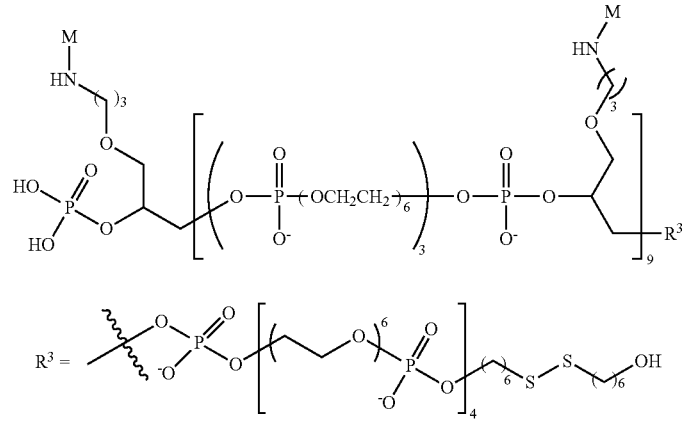 |
| III-55 | 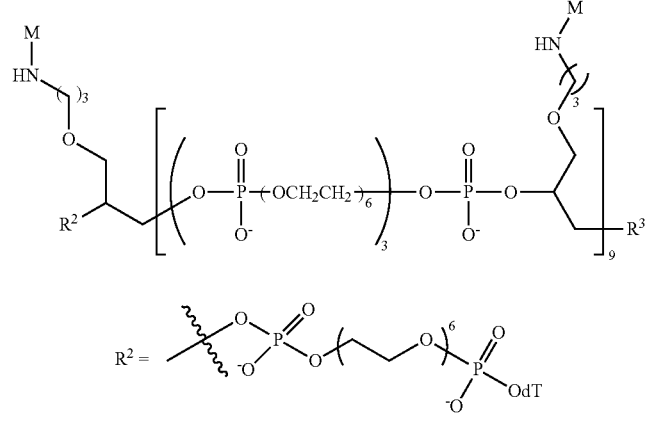 |
| III-56 | 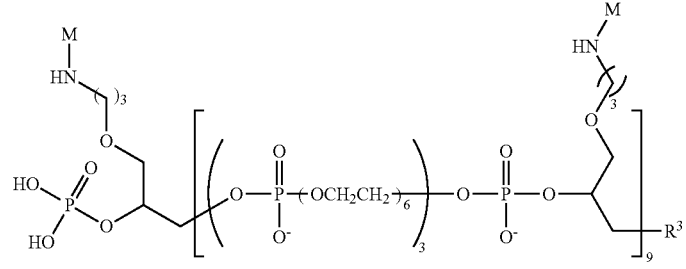 |

TABLE 3-continued

Exemplary Compounds of Structure I

| Compound | Structure |
|---|---|
| III-58 | 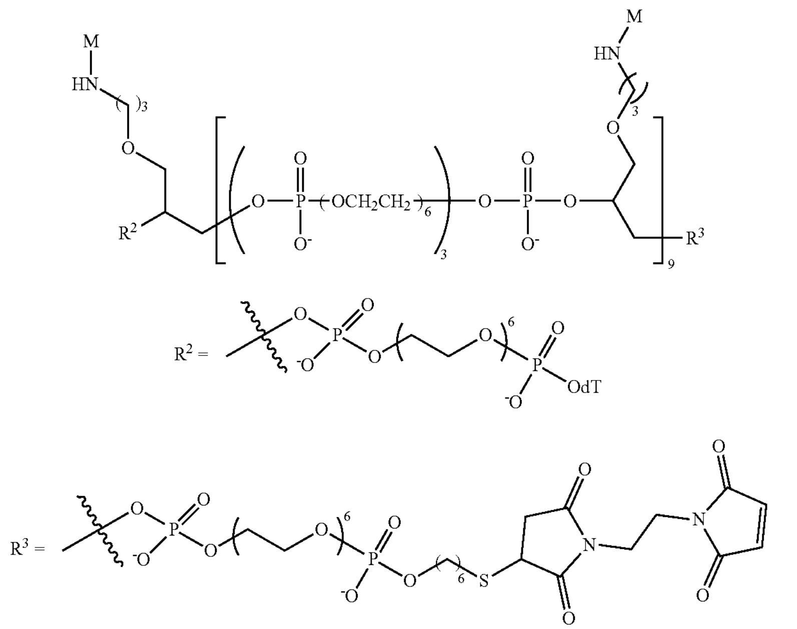 |
| III-59 | |
| III-59 | |

A = antibody

TABLE 3-continued
Exemplary Compounds of Structure I
| Compound | Structure |
|---|---|
| | 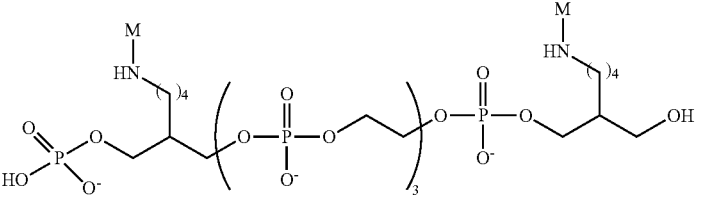 A = antibody |
| III-60 | 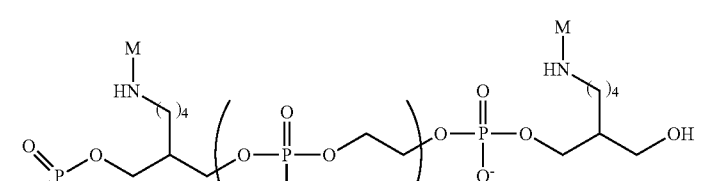 n = about 23 such that PEG M.W. = about 1,000 |
†Value of 20-25 is typically about 23, such that the molecular weight of the ethylene glycol moiety of the molecule is about 1000 g/mol.
TABLE 4
Exemplary Compounds of Structure I
| Cpd. | Structure |
|---|---|
| IV-1 | 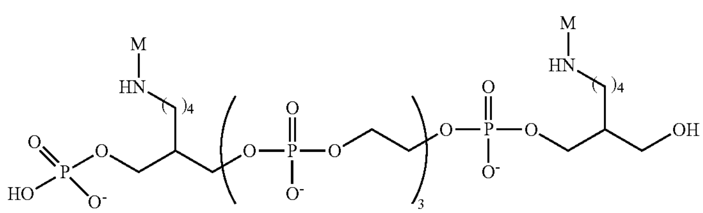 |
| IV-2 | 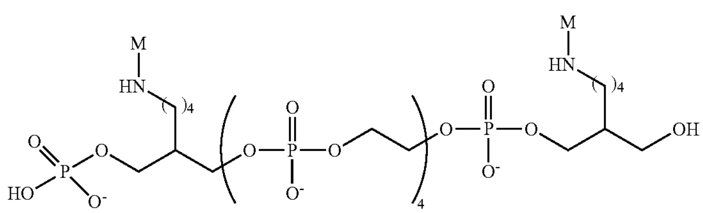 |
| IV-3 | 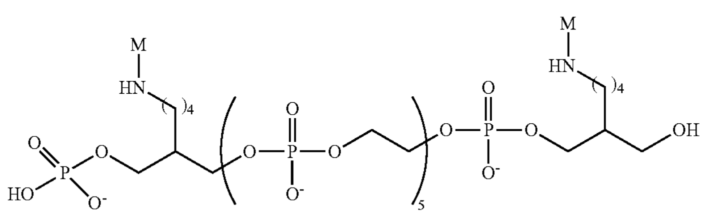 |
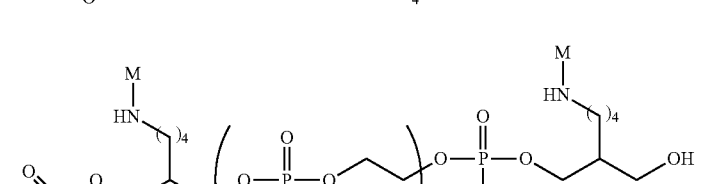

TABLE 4-continued

Exemplary Compounds of Structure I

| Cpd. | Structure |
|---|---|
| IV-4 | 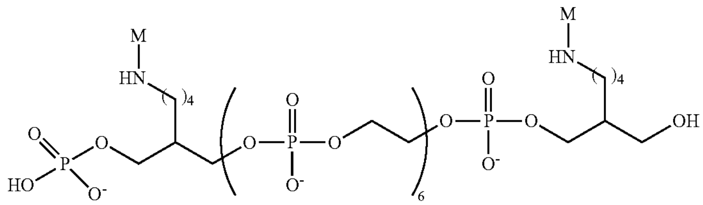 |
| IV-5 | 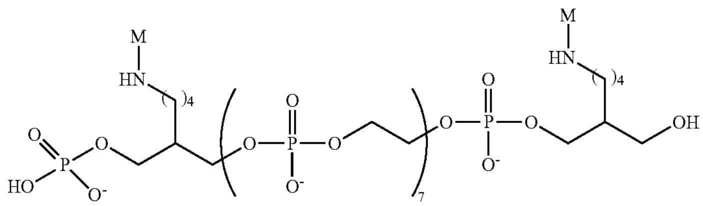 |
| IV-6 | 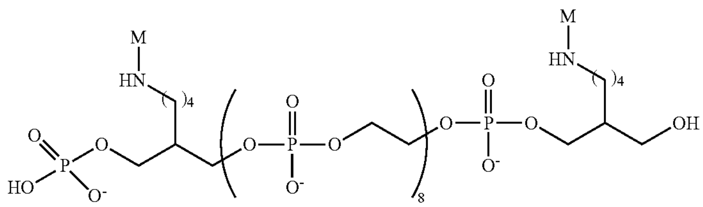 |
| IV-7 | 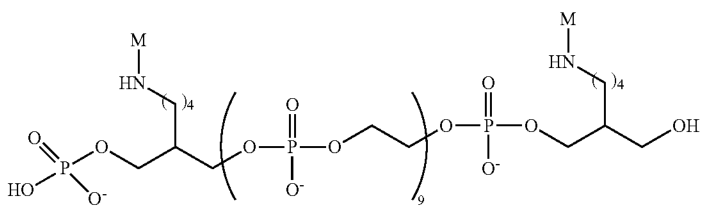 |
| IV-8 | 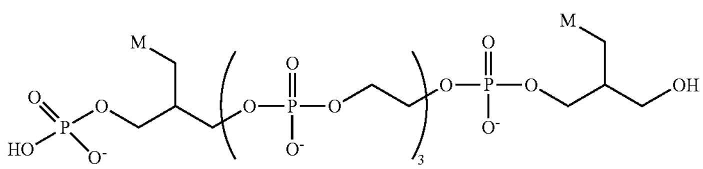 |
| IV-9 | 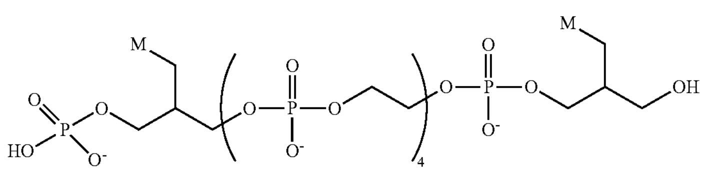 |
| IV-10 | 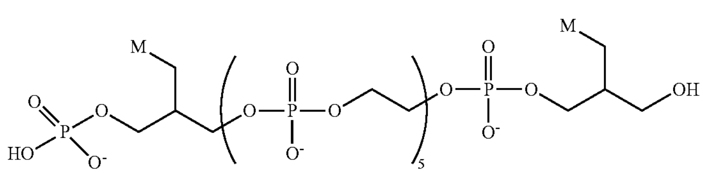 |
| IV-11 | 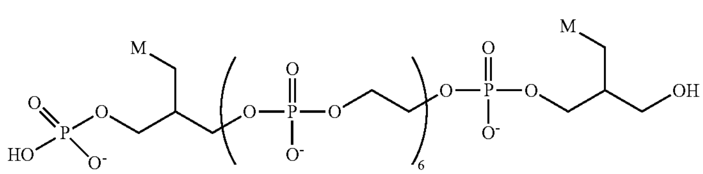 |

TABLE 4-continued

Exemplary Compounds of Structure I

| Cpd. | Structure |
|---|---|
| IV-12 | 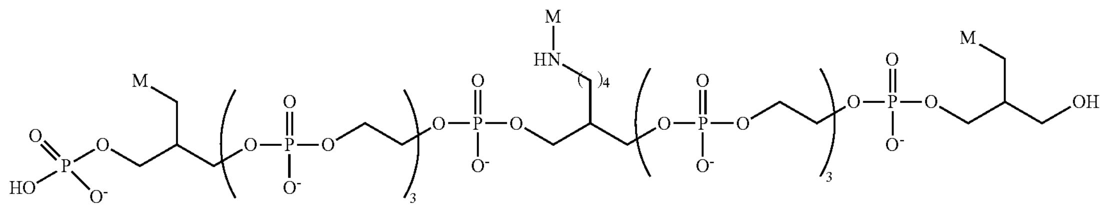 |
| IV-13 | 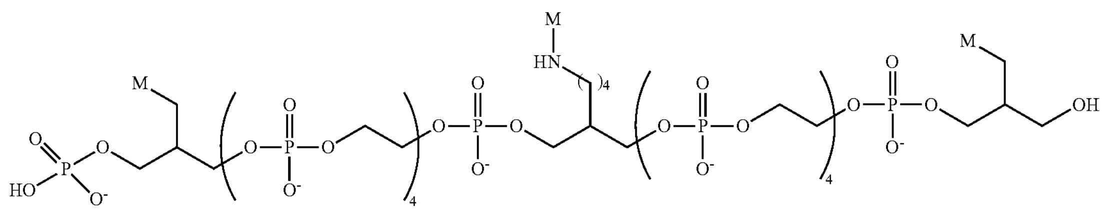 |
| IV-14 | 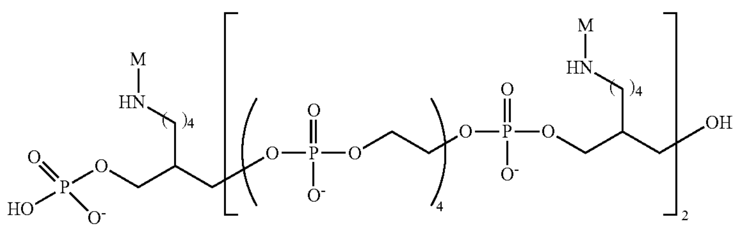 |
| IV-15 | 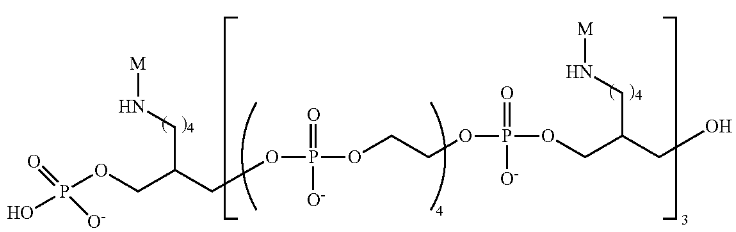 |
| IV-16 | 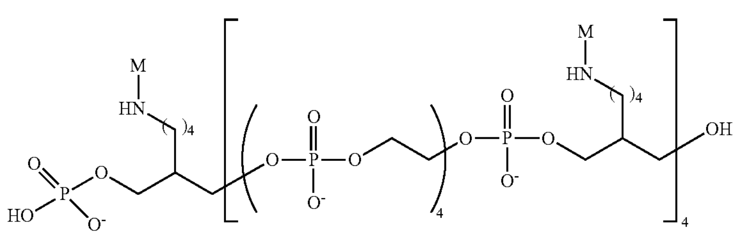 |
| IV-17 | 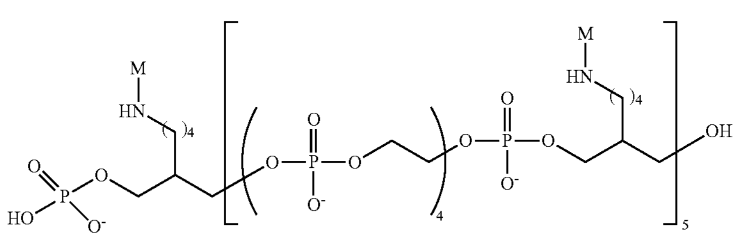 |

TABLE 4-continued

Exemplary Compounds of Structure I

| Cpd. | Structure |
|---|---|
| IV-18 | 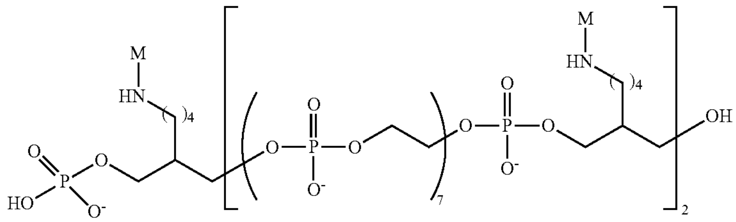 |
| IV-19 | 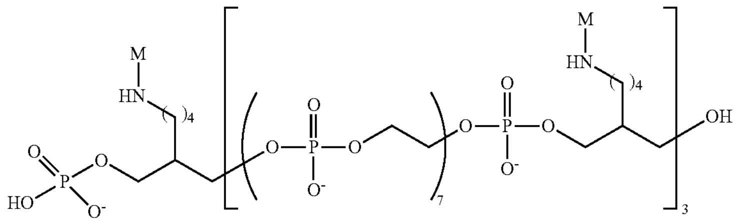 |
| IV-20 | 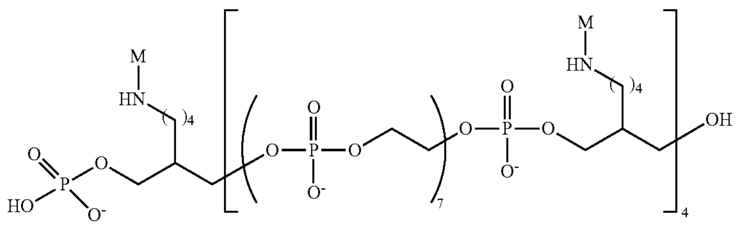 |
| IV-21 | 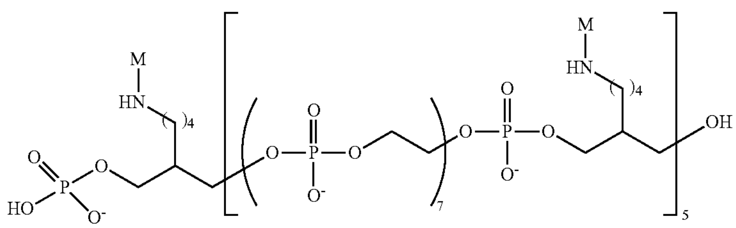 |
| IV-22 | 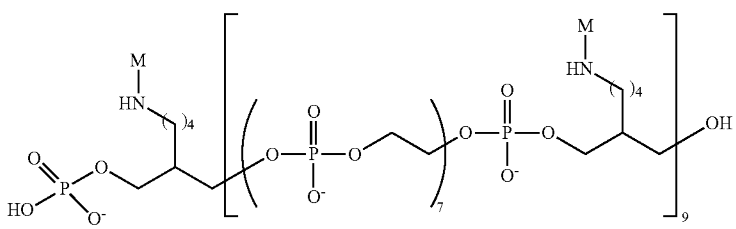 |
| IV-23 | 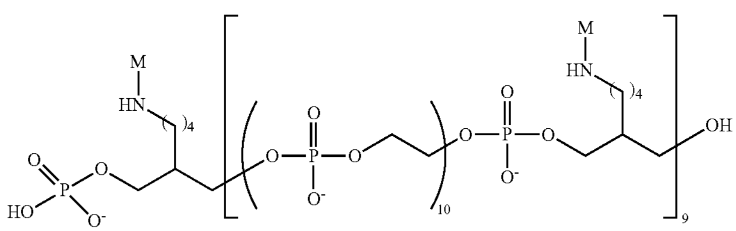 |

TABLE 4-continued
Exemplary Compounds of Structure I
| Cpd. | Structure |
|---|---|
| IV-24 | 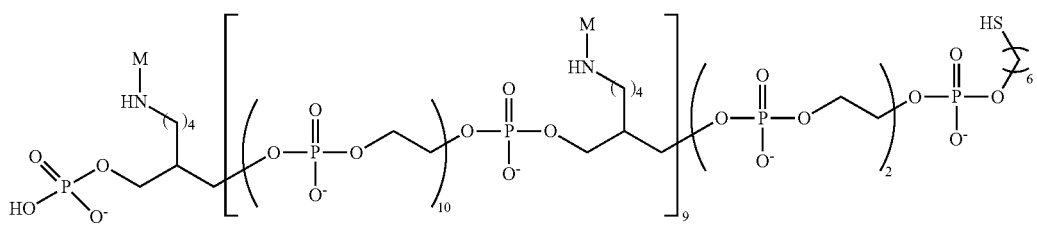 |
| IV-25 | 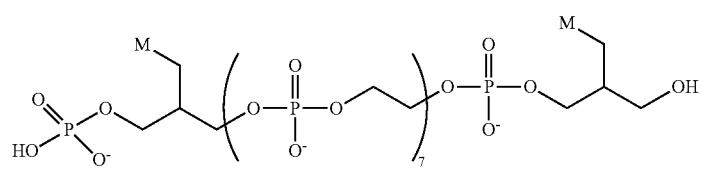 |
| IV-26 | 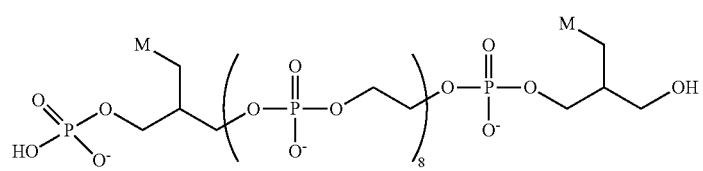 |
| IV-27 | 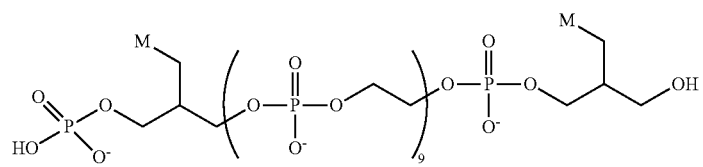 |
| IV-28 | 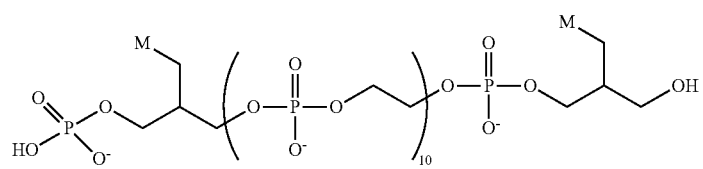 |
| IV-29 | 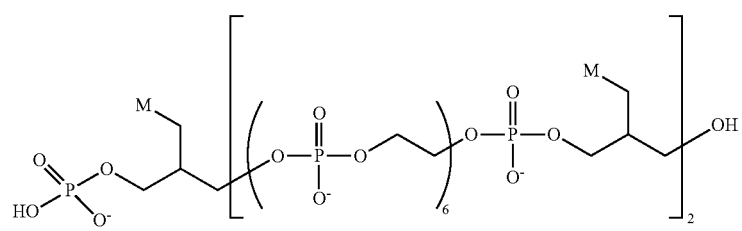 |
| IV-30 | 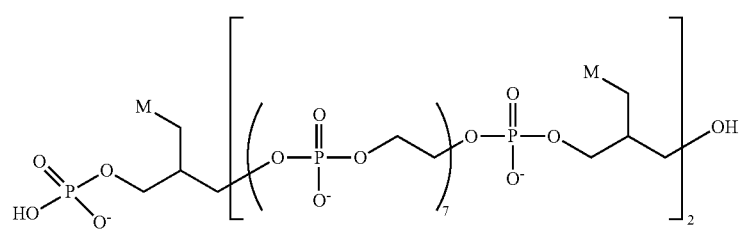 |

TABLE 4-continued
Exemplary Compounds of Structure I
| Cpd. | Structure |
|---|---|
| IV-31 | 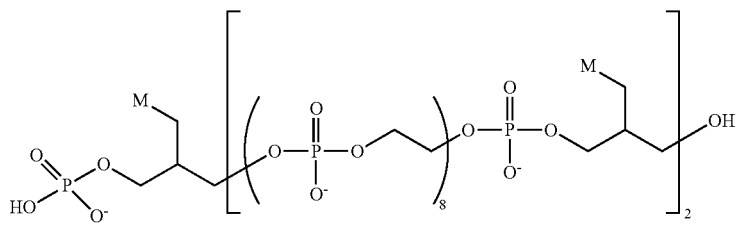 |
| IV-32 | 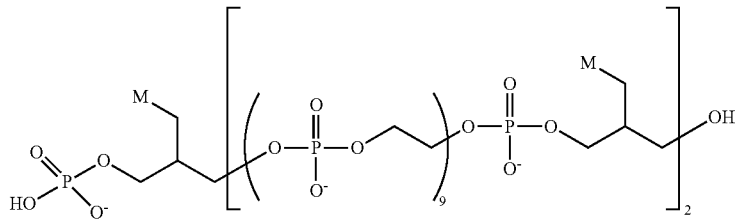 |
| IV-33 | 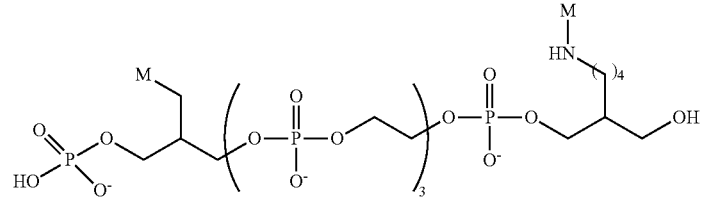 |
| IV-34 | 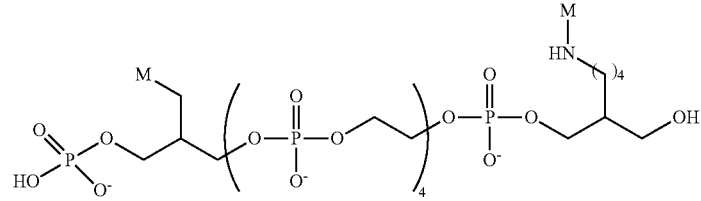 |
| IV-35 | 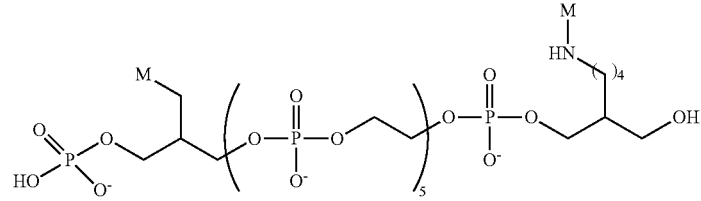 |
| IV-36 | 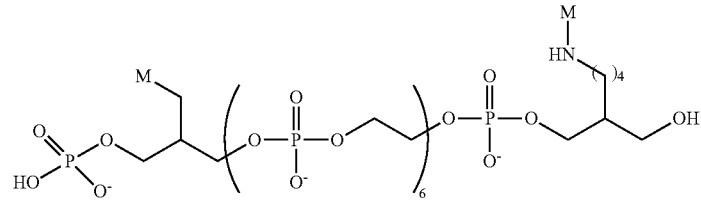 |

As used in Tables 2, 3 and 4 and throughout the application $R^2$, $R^3$, M, m, n and L' have the definitions provided for compounds of structure (I) unless otherwise indicated. In some embodiments, M is F, F', F", N', I', D', or D". F, F' and F" refer to a fluorescein moiety having the following structures, respectively:

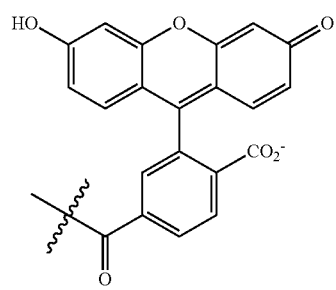 F

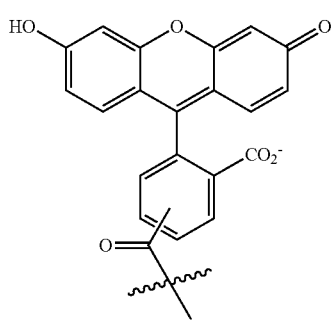 F'

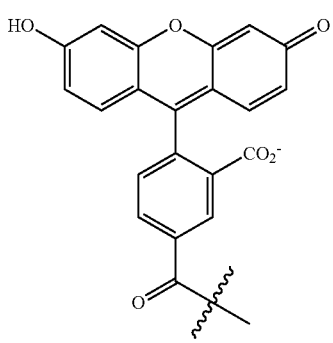 F"

"N'" refers to the following structure:

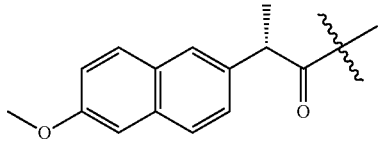 [SMILES: *C(=O)[C@@H](C)c1ccc2cc(OC)ccc2c1]

"I'" refers to the following structure:

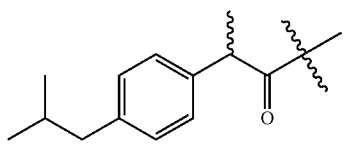 [SMILES: *C(=O)C(C)c1ccc(CC(C)C)cc1]

"D'" refers to the following structure:

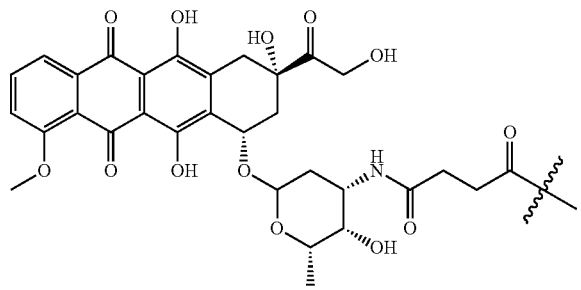 [SMILES: *C(=O)CCC(=O)N[C@H]1CC(O[C@H]2C[C@](O)(C(=O)CO)Cc3c(O)c4c(c(O)c32)C(=O)c2c(OC)cccc2C4=O)O[C@@H](C)[C@H]1O]

"D'" refers to the following structure:

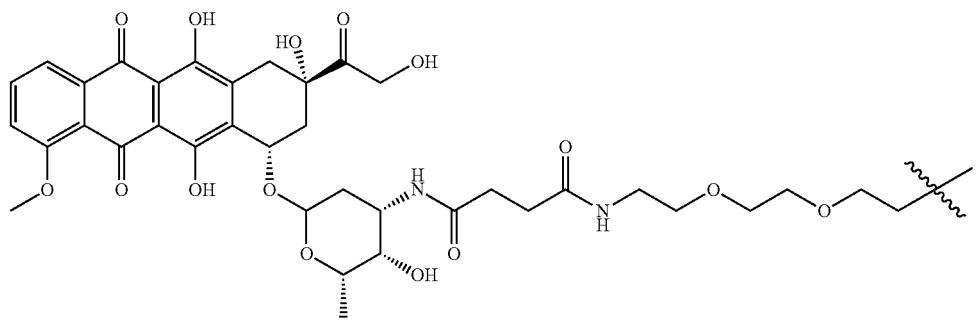 [SMILES: *CCOCCOCCNC(=O)CCC(=O)N[C@H]1CC(O[C@H]2C[C@](O)(C(=O)CO)Cc3c(O)c4c(c(O)c32)C(=O)c2c(OC)cccc2C4=O)O[C@@H](C)[C@H]1O]

"dT" refers to the following structure:
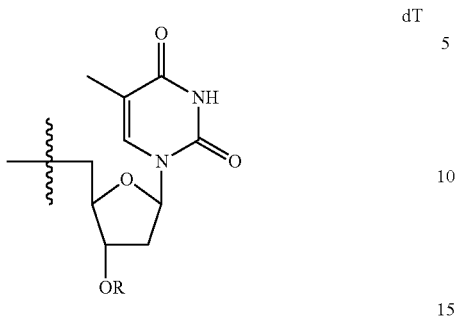
wherein:
R is H or a direct bond.
"AF" refers to the following structure:
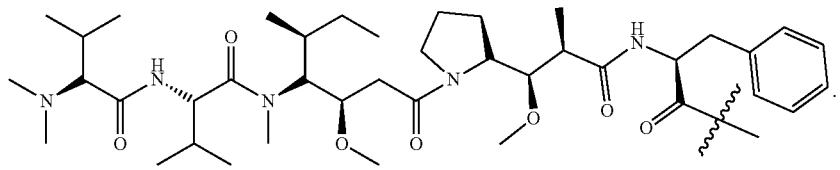
Accordingly, in some embodiments, at least one occurrence of M has one of the following structures:
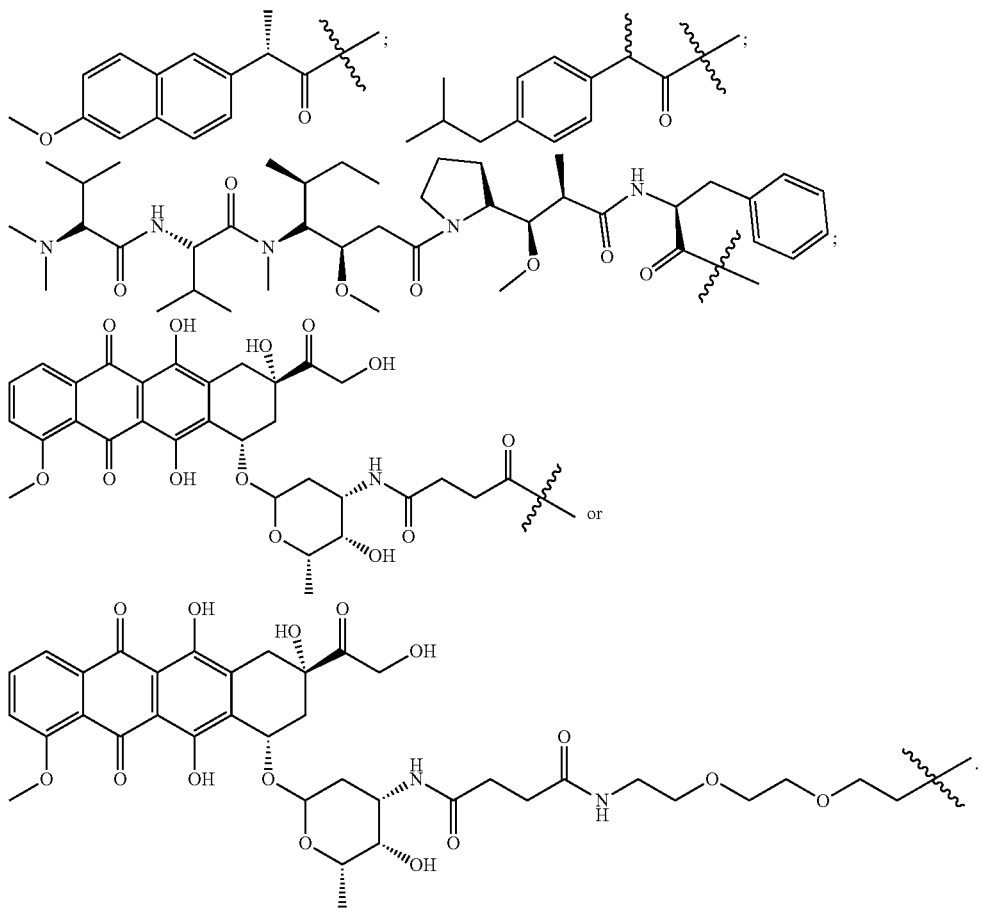

In some more specific embodiments, each occurrence of M has the following structure: moiety to form a covalent bond between M and the reactive polymer via any number of synthetic methodologies (e.g.,

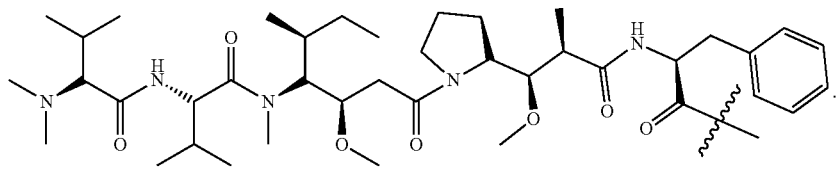

In certain embodiments, treating includes reducing or alleviating pain or inflammation. In certain embodiments, treating includes pain control or pain management. In some specific embodiments, at least one occurrence of M has one of the following structures:

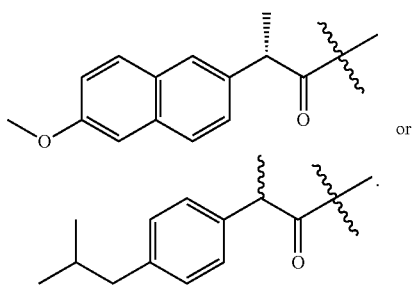

or

In some more specific embodiments, each occurrence of M has one of the following structure:

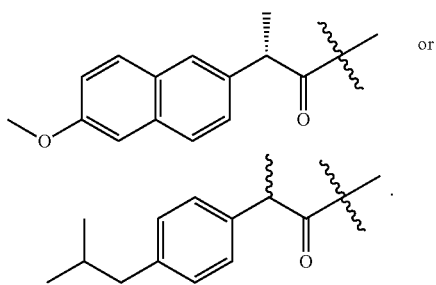

or

Some embodiments include any of the foregoing compounds, including the specific compounds provided in Table 2, conjugated to a targeting moiety, such as an antibody. In some embodiments, one compound of structure (I) is conjugated to an antibody. In some embodiments, 1-2 compounds of structure (I) are conjugated to an antibody. In some embodiments, 2 compounds of structure (I) are conjugated to an antibody. In some embodiments, 3 compounds of structure (I) are conjugated to an antibody. In some embodiments, 4 compounds of structure (I) are conjugated to an antibody. In some embodiments, 5 compounds of structure (I) are conjugated to an antibody. In some embodiments, no more than 5 compounds of structure (I) are conjugated to an antibody.

In various embodiments, reactive polymers can be used to prepare compounds of structure (I). In certain embodiments, these reactive polymers are synthetic intermediates that comprise a moiety useful for reacting with a complementary the "click" reactions described above), thereby forming a compound of structure (I). Accordingly, in various embodiments a compound of structure (I) is formed using a reactive polymer having the following structure (V):

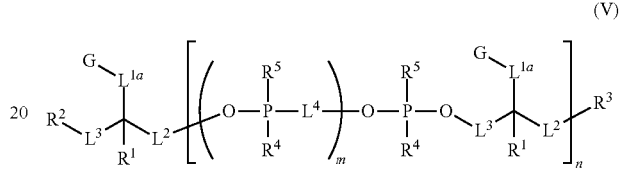

or a stereoisomer, salt or tautomer thereof, wherein:

G is, at each occurrence, independently a moiety comprising a reactive group, or protected analogue thereof, capable of forming a covalent bond with a complementary reactive group;

$L^{1a}$, $L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently a heteroalkylene, heteroalkenylene or heteroalkynylene linker of greater than three atoms in length, wherein the heteroatoms in the heteroalkylene, heteroalkenylene and heteroalkynylene linker are selected from O, N and S;

$R^1$ is, at each occurrence, independently H, alkyl or alkoxy;

$R^2$ and $R^3$ are each independently H, OH, SH, alkyl, alkoxy, alkylether, heteroalkyl, $-OP(=R_a)(R_b)R_c$, Q or L';

$R^4$ is, at each occurrence, independently OH, SH, O$^-$, S$^-$, $OR_d$ or $SR_d$;

$R^5$ is, at each occurrence, independently oxo, thioxo or absent;

$R_a$ is O or S;

$R_b$ is OH, SH, O$^-$, S$^-$, $OR_d$ or $SR_d$;

$R_c$ is OH, SH, O$^-$, S$^-$, $OR_d$, OL', $SR_d$, alkyl, alkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected analogue thereof, capable of forming a covalent bond with an analyte molecule, targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (V);

m is, at each occurrence, independently an integer of zero or greater, provided that at least one occurrence of m is an integer of one or greater; and n is an integer of one or greater.

In some embodiments, the reactive polymer is selected from Table 5, below.

TABLE 5

Exemplary Reactive Polymers

| No. | Structure |
|---|---|
| V-1 | 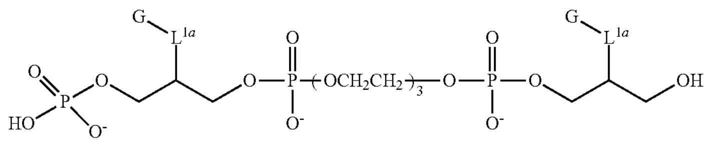 |
| V-2 | 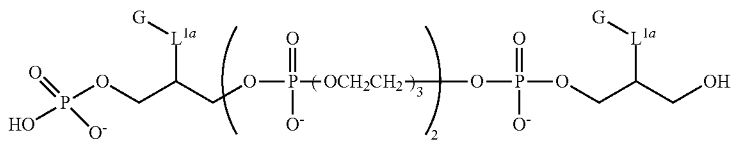 |
| V-3 | 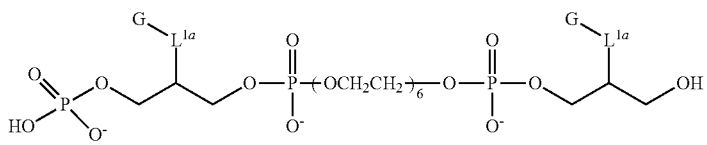 |
| V-4 | 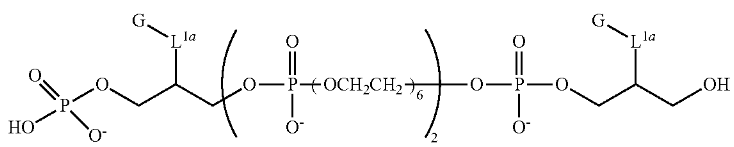 |
| V-5 | 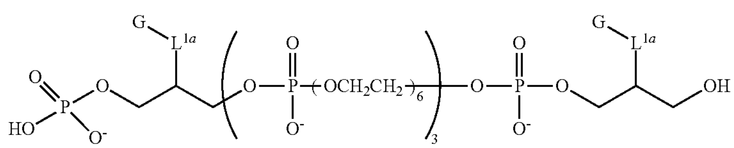 |
| V-6 | 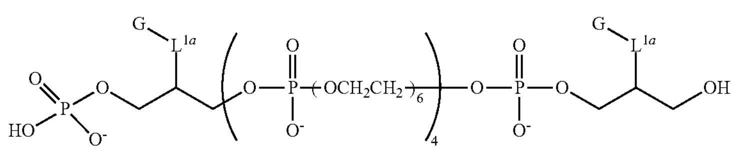 |
| V-7 | 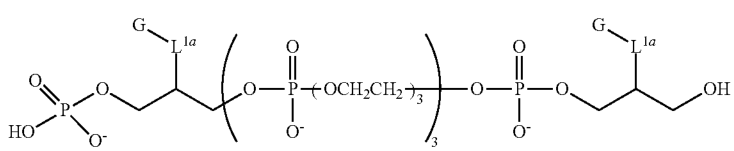 |
| V-8 | 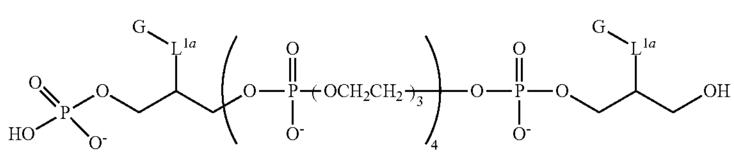 |
| V-9 | 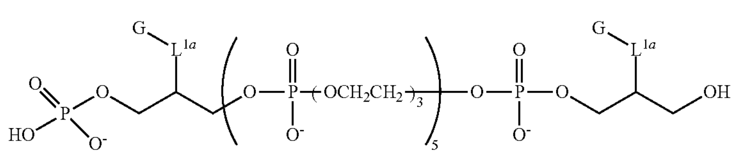 |

TABLE 5-continued

Exemplary Reactive Polymers

| No. | Structure |
|---|---|
| V-10 | 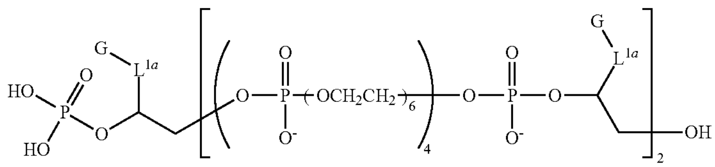 |
| V-11 | 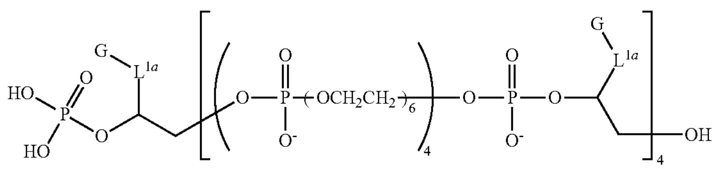 |
| V-12 | z = 3, 4, 5 or 6<br>m = 2, 3, 4 or 5<br>n = 1-10 |
| V-13 | 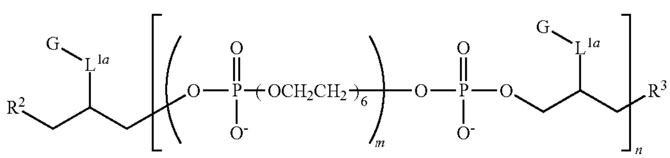 |
| V-14 | 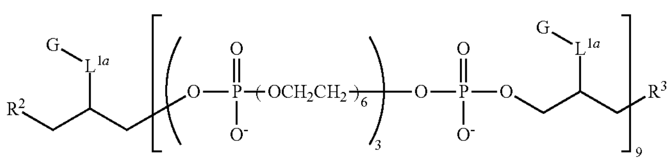 |
| V-15 | 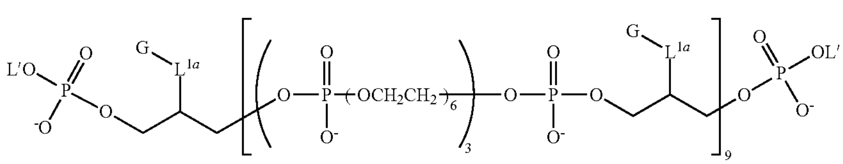 |
| V-16 | 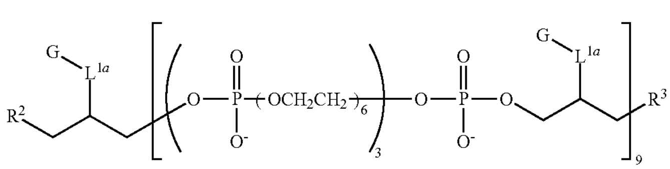 |

TABLE 5-continued

Exemplary Reactive Polymers

| No. | Structure |
|---|---|
| V-17 | (chemical structure) |
| V-18 | (chemical structure) |
| V-19 | (chemical structure); A = antibody |

TABLE 5-continued

Exemplary Reactive Polymers

| No. | Structure |
|---|---|
| V-20 | |
| V-21 | |
| V-22 | | m" = 4 or 10 m" = 4 or 10
A = antibody

TABLE 5-continued

Exemplary Reactive Polymers

| No. | Structure |
|---|---|

V-23

V-24

V-25

TABLE 5-continued

Exemplary Reactive Polymers

| No. | Structure |
|---|---|

V-26

V-27

V-28

A = antibody

TABLE 5-continued

Exemplary Reactive Polymers

| No. | Structure |
|---|---|
| V-29 | (structure) |
| V-30 | (structure) |

In various embodiments, G in the compounds of Table 5 is alkynyl, such as ethynyl. In other embodiments, G in the compounds of Table 5 is an azide. In other embodiments, G in the compounds of Table 5 is amino ($N_2$). In other embodiments, G in the compounds of Table 5 is an isothiocyanate. In other embodiments, G in the compounds of Table 5 is an activated ester, such as an ester of N-hydroxysuccinimide.

Certain embodiments are directed to a therapeutically effective fluorescent compound provided at least one occurrence of M is not a fluorescent dye and at least one occurrence of M is a fluorescent dye. Therapeutically effective fluorescent compounds include compounds comprising at least one biologically active moiety or fragment thereof or a prodrug of a biologically active moiety, or fragment thereof, which emit a fluorescent signal upon excitation with light, such as ultraviolet light.

In still more embodiments, the compound of structure (I) comprises at least one ethylene oxide moiety.

Compositions comprising the compound of any one of claims and a targeting moiety are also provided.

Embodiments of the presently disclosed compounds are "tunable," meaning that by proper selection of the variables in any of the foregoing compounds, one of skill in the art can arrive at a compound having a desired and/or predetermined molar fluorescence (molar brightness). The "tunability" of certain embodiments of the compounds allows the user to easily arrive at compounds having the desired fluorescence and/or color for use in a particular assay. Although all variables may have an effect on the molar fluorescence of certain embodiments of the compounds disclosed herein, proper selection of M, $L^4$, m and n is believed to play an important role in the molar fluorescence of embodiments of the disclosed compounds. Accordingly, in one embodiment is provided a method for obtaining a compound having a desired molar fluorescence, the method comprising selecting an M moiety having a known fluorescence, preparing a compound of structure (I) comprising the M moiety, and selecting the appropriate variables for $L^4$, m and n to arrive at the desired molar fluorescence.

For ease of illustration, various compounds comprising phosphorous moieties (e.g., phosphate and the like) are depicted in the anionic state (e.g., —OPO(OH)O⁻, —OPO$_3^{2-}$). One of skill in the art will readily understand that the charge is dependent on pH and the uncharged (e.g., protonated or salt, such as sodium or other cation) forms are also included in the scope of embodiments of the invention.

Compositions comprising any of the foregoing compounds and one or more targeting moiety (e.g., antibody or cell surface receptor antagonist) are provided in various other embodiments. In some embodiments, use of such compositions in methods for treating a disease the method comprising administering to a subject in need thereof a therapeutically effective amount of a compound of structure (I) or a composition comprising a compound of structure (I) wherein each M is independently a biologically active moiety effective for treating the disease are also provided.

Pharmaceutical Compositions

One embodiment provides a composition comprising the compound according any one of the embodiments disclosed herein and a pharmaceutically acceptable carrier.

Another embodiment provides a composition comprising a plurality of conjugates, the conjugates comprising an antibody covalently bound to two or more biologically active moieties via a single linkage, wherein the plurality of conjugates has at least 90% structural homogeneity. In more specific embodiments, the plurality of conjugates has at least 95% structural homogeneity. In related embodiments, the plurality of conjugates has greater than 99% structural homogeneity. In certain embodiments, the single linkage is a linkage to a polymer backbone, the polymer backbone comprising the two or more biologically active moieties covalently bound thereto.

In certain embodiments, each conjugate independently is a compound according to an embodiment disclosed herein, wherein one of R² and R³ is —OP(=R$_a$)(R$_b$) OL' or L', and L' is the antibody or a linker comprising a covalent bond to the antibody.

Other embodiments are directed to pharmaceutical compositions. The pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the invention is administered in a single dose. Typically, such administration will be by injection, e.g., intravenous injection, in order to introduce the agent quickly. However, other routes are used as appropriate. A single dose of a compound of the invention may also be used for treatment of an acute condition.

In some embodiments, a compound of the invention is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

In some embodiments, the compounds of the invention are administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkinsl 999).

Provided herein are pharmaceutical compositions comprising a compound of structure (I) and a pharmaceutically acceptable diluent(s), excipient(s), or carrier(s). In certain embodiments, the compounds described are administered as pharmaceutical compositions in which compounds of structure (I) are mixed with other active ingredients, as in combination therapy. Encompassed herein are all combinations of actives set forth in the combination therapies section below and throughout this disclosure. In specific embodiments, the pharmaceutical compositions include one or more compounds of structure (I).

A pharmaceutical composition, as used herein, refers to a mixture of a compound of structure (I) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of structure (I) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of structure (I) is formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound of structure (I) is/are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds (e.g., compounds of structure (I)) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of structure (I) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of structure (I) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of structure (I) is accomplished by means of iontophoretic patches and the like. In certain embodiments, transdermal patches provide controlled delivery of the compounds of structure (I). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of structure (I) are formulated for administration by inhalation. Various forms suitable for administration by inhalation include, but are not limited to, aerosols, mists or powders. Pharmaceutical compositions of any of compound of structure (I) are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator is formulated containing a powder mix of the compound and a suitable powder base such as lactose or starch.

In still other embodiments, the compounds of structure (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of structure (I) are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of structure (I), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of structure (I) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of structure (I). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds provided in the pharmaceutical compositions is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds ranges from 0.0001 to 10 g, 0.0005 to 9 g, 0.001 to 8 g, 0.005 to 7 g, 0.01 to 6 g, 0.05 to 5 g, 0.1 to 4 g, 0.5 to 4 g, or 1 to 3 g.

Methods of Treatment

In still other embodiments, the compounds are useful in various methods of treating a disease or condition. Accordingly, one embodiment provides a method of treating a disease, the method comprising administering to a subject in need thereof a therapeutically effective amount of a compound according to any one of the embodiments disclosed herein or a composition according to any one of the embodiments disclosed herein, wherein each M is independently a biologically active moiety effective for treating the disease. In some embodiments, the disease is cancer, and each M is independently an anti-cancer drug. In some embodiments, at least one occurrence of M has the following structure:

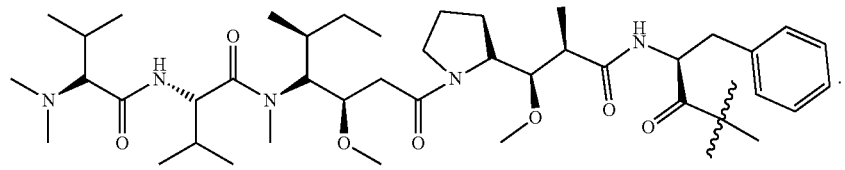

In some embodiments, each occurrence of M has the following structure:

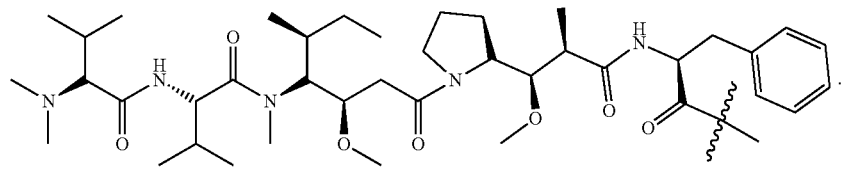

For example, in certain embodiments the disclosure provides a method of treating solid tumors, multiple myeloma, gliomas, clear cell renal cell carcinoma, prostate cancer, ovarian cancer, non-small cell lung cancer, GI malignancies, acute lymphoblastic leukemia, acute myelogenous leukemia, renal cell carcinoma, colorectal carcinoma, epithelial cancers, pancreatic and gastric cancers, renal cell carcinoma, non-Hodgkin's lymphoma, metastatic renal cell carcinoma, malignant mesothelioma, pancreatic, ovarian, and/or lung adenocarcinoma, B-cell malignancies, breast cancer, melanoma, recurrent multiple myeloma, small cell lung cancer, CD22-positive B cell malignancies, Hodgkin's lymphoma/anaplastic large cell lymphoma, or HER2-positive breast cancer.

Certain embodiments also relate to a method of treating a hyperproliferative disorder in a mammal (e.g., a human) that comprises administering to said mammal a therapeutically effective amount of a compound, or a pharmaceutically acceptable salt, ester, prodrug, solvate, hydrate or derivative thereof. In some embodiments, said method relates to the treatment of cancer such as acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, Ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin's lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-Hodgkin's lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

Certain particular embodiments provide methods for treatment of lung cancers, the methods comprise administering an effective amount of any of the above described compounds (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Accordingly, in some embodiments of the foregoing methods, $R^2$ is a linker comprising a covalent linkage to a targeting moiety, such as an antibody or a cell surface receptor antagonist. For example, epidermal growth factor receptor (EGFR) inhibitor, a hepatocyte growth factor receptor (HGFR) inhibitor, an insulin-like growth factor receptor (IGFR) inhibitor, a folate, or a MET inhibitor.

In even more embodiments, the method further comprises inducing apoptosis.

In some embodiments, the method for treating a disease further comprises:

(a) providing a compound of structure (I), for example, wherein one of $R^2$ or $R^3$ is a linker comprising a covalent bond to an analyte molecule, and the other of $R^2$ or $R^3$ is H, OH, alkyl, alkoxy, alkylether or $-OP(=R_a)(R_b)R_c$; and (b) detecting the compound by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In certain embodiments, the providing further comprises admixing a compound of structure (I) with an analyte molecule.

Embodiments of the present compounds thus find utility in any number of methods, including, but not limited: drug delivery; quantifying apoptosis; qualifying therapeutic drug delivery; quantifying apoptosis; and diagnosing and treating diseases, such as blood cancers.

In addition to the above methods, embodiments of the compounds of structure (I) find utility in various disciplines and methods, including but not limited to: cancer treatment and imaging, for example by including a targeting moiety, such as an antibody or sugar or other moiety that preferentially binds cancer cells, in a compound of structure (I) to; and/or drug delivery.

In some embodiments, the method of treatment comprises treating a tumor having tumor cells with tumor cell receptors. In some embodiments, the tumor cells have receptors ranging from 1,000 to 100,000, from 1,000 to 50,000, from 1,000 to 25,000 receptors, 1,000 to 10,000 receptors per cell. For example, in some embodiments the tumor cells have about 1,000, about 10,000, or less than 100,000 receptors per cell.

Embodiments of the present disclosure are not limited to treatment of cancer. In fact, the disclosures are not particularly limited with respect to the types of diseases, symptoms, conditions, indications, and treatments for which compounds and methods the present disclosure can be adapted. That is, the present disclosure provides compounds, compositions, and methods for treating or preventing a wide variety of diseases. For example, the compounds and compositions disclosed herein can be modified by selecting an appropriate biological moiety or combination of biological moieties to treat a particular disease as desired. Based on the present disclosure, it will be readily apparent to one of ordinary skill in the art how to modify the compounds and compositions presently disclosed in order to treat, prevent or target a disease, symptom or clinical indication.

Accordingly, methods of the present disclosure include methods of administering a compound of the present disclosure for treating diseases, conditions, or symptoms of a disease or condition, preventing diseases or symptoms of a disease or condition, prophylactically treating diseases, conditions or symptoms of a disease or condition, identifying a subject at risk and treating diseases, conditions, or symptoms of a disease or condition, slowing or stopping progression of diseases, conditions, or symptoms of a disease or condition, increasing the survival rate of a subject having diseases, conditions, or symptoms of a disease or condition, ameliorating the symptoms of diseases, conditions, or symptoms of a disease or condition, and the like.

Additionally, the diseases, conditions, symptoms, afflictions, side effects, maladies, syndromes, biological occurrences, biological abnormalities, medical conditions, illnesses, pathosis, pathology, and the like are meant to be included within the present disclosure and are also not particularly limited; examples include, but are not limited to, cancer, inflammation, pain, pain control, inflammatory diseases, infectious diseases, viral infections, genetic disorders, bacterial infections, fungal infections, cutaneous conditions, endocrine conditions, ocular disorders, intestinal disease, neurological disorders, liver disorders, lung infections, heart conditions and disorders, mental illness (e.g., eating disorders, mood disorders, personality disorders), norovirus infections, blood-borne pathogens, protozoan infections, viral hepatitis, HIV/AIDS, diabetes, sclerosis, Crohn's and colitis, lupus, arthritis, allergies and asthma, celiac disease, polychondritis, scleroderma, liver disease, heart disease, acquired diseases, acute diseases, chronic conditions or diseases, congenital diseases or disorders, hereditary diseases or disorders, iatrogenic disease, idiopathic disease, primary disease, secondary disease, terminal disease, or similar. The foregoing may be acute, chronic, clinical, a flare-up, progressive, refractory, subclinical, localized, disseminated, systemic, or the like. Any of the foregoing examples may include being caused as a result of an airborne, foodborne, infections, or lifestyle event.

Methods of Preparation

It is understood that any embodiment of the compounds of structure (I), as set forth above, and any specific choice set forth herein for a $R^1$, $R^2$, $R^3$, L, $L^1$, $L^2$, $L^3$, M, and/or n variable in the compounds of structure (I), as set forth above, may be independently combined with other embodiments and/or variables of the compounds of structure (I) to form embodiments of the invention not specifically set forth above. In addition, in the event that a list of choices is listed for any particular $R^1$, $R^2$, $R^3$, L, $L^1$, $L^2$, $L^3$, M, and/or n variable in a particular embodiment and/or claim, it is understood that each individual choice may be deleted from the particular embodiment and/or claim and that the remaining list of choices will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention which exist in free base or acid form can be converted to their salts by treatment with the appropriate inorganic or organic base or acid by methods known to one skilled in the art. Salts of the compounds of the invention can be converted to their free base or acid form by standard techniques.

The following Reaction Schemes illustrate exemplary methods of making compounds of this invention. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Reaction Scheme I

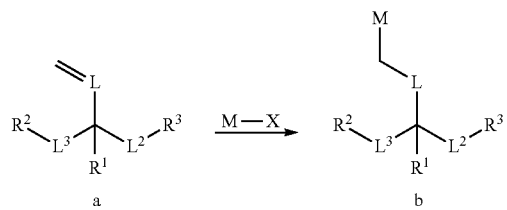

Reaction Scheme I illustrates an exemplary method for preparing an intermediate useful for preparation of compounds of structure (I), where $R^1$, $L^2$, $L^3$ and M are as defined above, $R^2$ and $R^3$ are as defined above or are protected variants thereof and L is an optional linker. Referring to Reaction Scheme 1, compounds of structure a can be purchased or prepared by methods well-known to those of ordinary skill in the art. Reaction of a with M-X, where x is a halogen such as bromo, under Suzuki coupling conditions known in the art results in compounds of structure b. Compounds of structure b can be used for preparation of compounds of structure (I) as described below.

Reaction Scheme II

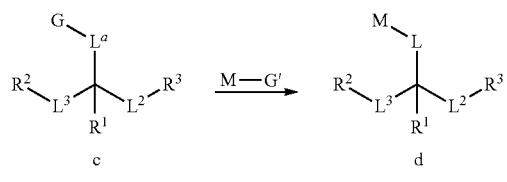

Reaction Scheme II illustrates an alternative method for preparation of intermediates useful for preparation of compounds of structure (I). Referring to reaction Scheme II, where $R^1$, L, $L^2$, $L^3$ and M are as defined above, and $R^2$ and $R^3$ are as defined above, or are protected variants thereof, a compound of structure c, which can be purchased or prepared by well-known techniques, is reacted with M-G' to yield compounds of structure d. Here, G and G' represent functional groups having complementary reactivity (i.e., functional groups which react to form a covalent bond). G' may be pendant to M or a part of the structural backbone of M. La is an intermediate selected such that the reaction depicted above converts $L_a$ to L. G and G' may be any number of functional groups described herein, such as alkyne and azide, respectively, amine and activated ester, respectively or amine and isothiocyanate, respectively, and the like.

The compound of structure (I) may be prepared from one of structures b or d by reaction under well-known automated DNA synthesis conditions with a phosphoramidite compound having the following structure (e):

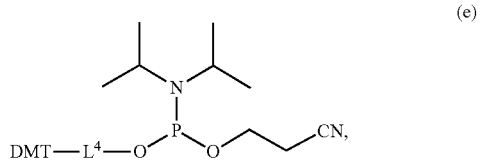

wherein A is as defined herein and each L is independently an optional linker.

DNA synthesis methods are well-known in the art. Briefly, two alcohol groups, for example $R^2$ and $R^3$ in intermediates b or d above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $R^3$) can be protected as a DMT group by reaction with DMT-Cl. A secondary alcohol (e.g., $R^2$) is then functionalized as a phosphoramidite by reaction with an appropriate reagent such as 2-cyanoethyl N,N-dissopropylchlorophosphoramidite. Methods for preparation of phosphoramidites and their oligomerization are well-known in the art.

Compounds of structure (I) are prepared by oligomerization of intermediates b or d and e according to the well-known phophoramidite chemistry described above. The desired number of n repeating units is incorporated into the molecule by repeating the phosphoramidite coupling the desired number of times.

In exemplary embodiments, the G moiety can be selected from any of the Q moieties described herein, including those specific examples provided in Table 1. In some embodiments, G comprises, at each occurrence, independently a moiety suitable for reactions including: the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom.

In some embodiments, G is, at each occurrence, independently a moiety comprising an aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin or thiirane functional group.

In other embodiments, G comprises, at each occurrence, independently an alkyne or an azide group. In other embodiments, G comprises, at each occurrence, independently an amino, isothiocyanate or activated ester group. In different embodiments, G comprises, at each occurrence, independently a reactive group capable of forming a functional group comprising an alkene, ester, amide, thioester, disulfide, carbocyclic, heterocyclic or heteroaryl group, upon reaction with the complementary reactive group. For example, in some embodiment the heteroaryl is triazolyl.

Methods for preparing the compounds of structure (II) as well as methods for using automated DNA synthetic techniques for compound preparation are described in U.S. patent application Ser. No. 15/481,378, PCT Pub. No. WO 2015/027176, WO 2016/138461, and WO 2016/183185 all of which are incorporated herein in their entireties by reference.

The following examples are provided for purposes of illustration, not limitation.

EXAMPLES

General Methods

Mass spectral analysis was performed on a Waters/Micromass Quattro micro MS/MS system (in MS only mode) using MassLynx 4.1 acquisition software. Mobile phase used for LC/MS on dyes was 100 mM 1,1,1,3,3,3-hexafluoro-2-propanol (HIP), 8.6 mM triethylamine (TEA), pH 8. Phosphoramidites and precursor molecules were also analyzed using a Waters Acquity UHPLC system with a 2.1 mm×50 mm Acquity BEH-C18 column held at 45° C., employing an acetonitrile/water mobile phase gradient. Molecular weights for monomer intermediates were obtained using tropylium cation infusion enhanced ionization on a Waters/Micromass Quattro micro MS/MS system (in MS only mode). Excitation and emission profiles experiments were recorded on a Cary Eclipse spectra photometer.

All reactions were carried out in oven dried glassware under a nitrogen atmosphere unless otherwise stated. Commercially available DNA synthesis reagents were purchased from Glen Research (Sterling, Va.). Anhydrous pyridine, toluene, dichloromethane, diisopropylethyl amine, triethylamine, acetic acid, pyridine, and THE were purchased from Aldrich. All other chemicals were purchase from Aldrich or TCI and were used as is with no additional purification.

Example 1

Synthesis of Ibuprofen-NHS and Naproxen-NHS

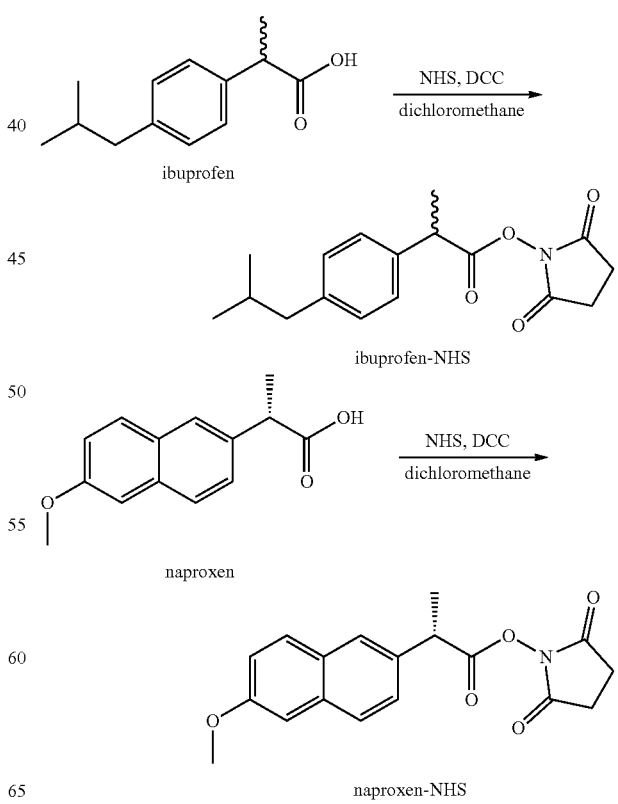

Ibuprofen-NHS and naproxen-NHS were synthesized using standard coupling conditions. That is, ibuprofen and naproxen were separately dissolved in dichloromethane and to the mixture was added N,N'-dicyclohexylcarbodiimide (DCC) and N-hydroxysuccinimide (NHS). Products were then purified as necessary and used in the next synthetic step. Ibuprofen-NHS is easily synthesized in one step on a multi-gram scale.

Example 2

Synthesis of Ibuprofen-Phosphoramidite

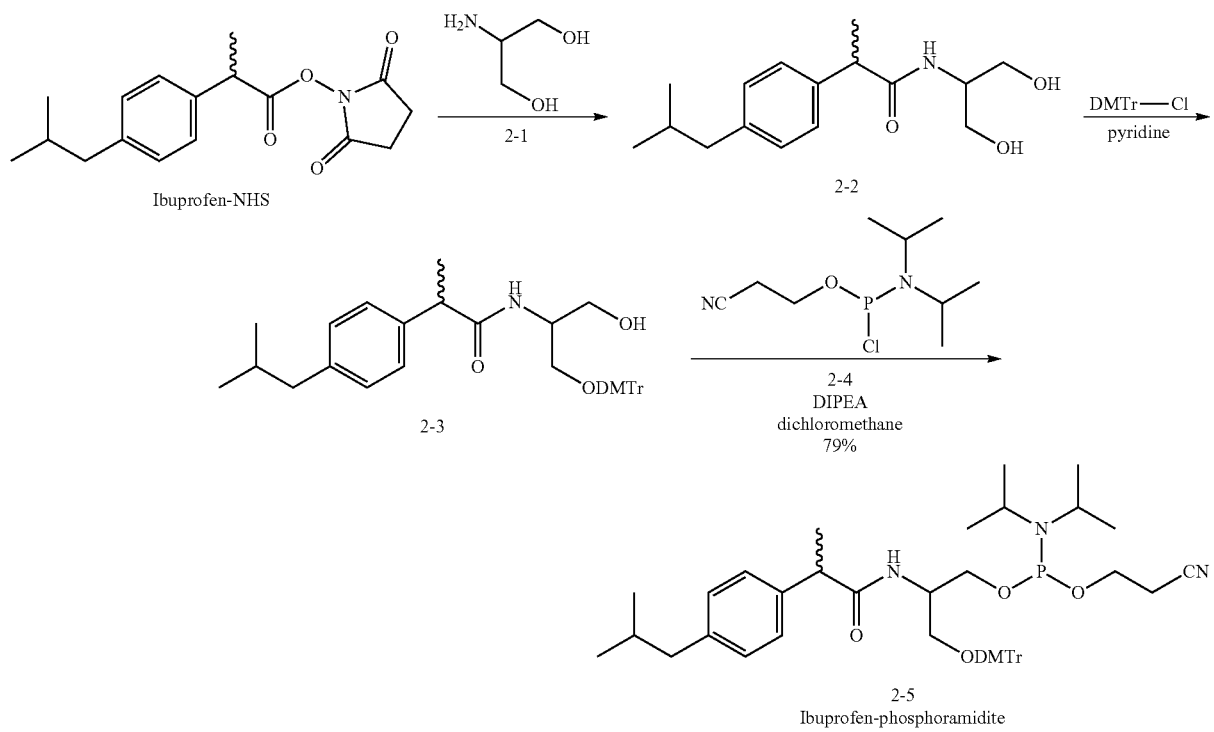

An extendable derivative of ibuprofen was synthesized according to the reactions shown above as a representative derivative to be incorporated into embodiments of the compounds described herein. Ibuprofen-NHS was reacted with 2-1 (2-amino-1,3-propane diol) followed by the addition of a trityl protecting group to afford intermediate 2-3. The protected product 2-3 was then reacted with 2-4 to afford the final product, 2-5 ibuprofen-phosphoramidite (79%). The ibuprofen-phosphoramidite was then used for automated DNA synthesis to incorporate ibuprofen as a representative biologically active moiety into embodiments of the compounds described herein.

Alternatively, ibuprofen-NHS was reacted with 4-(aminomethoxy)butane-1,2,-diol and subsequently derivatized according to the reaction sequence shown above. The resultant final product of that reaction sequence afforded an alternative ibuprofen phosphoramidite with an extended linker relative to ibuprofen-phosphoramidite shown above.

Example 3

Synthesis of Naproxen-Phosphoramidite

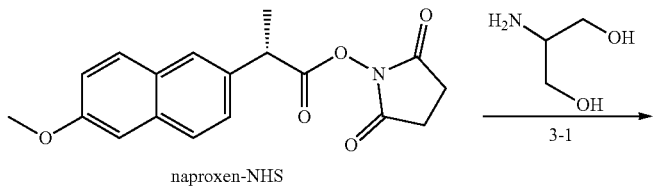

naproxen-NHS

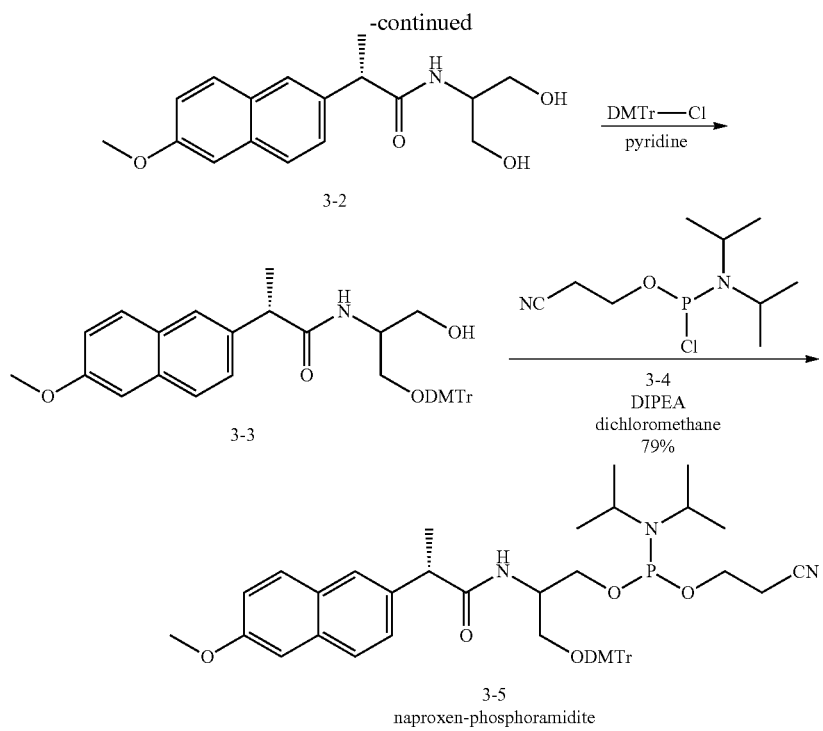

3-5
naproxen-phosphoramidite

Naproxen-phosphoramidite (3-5) was synthesized using analogous reaction conditions and reagents as described for the synthesis of ibuprofen-phosphoramidite shown in Example 2. The desired product was afforded in good yield (79%) and incorporated as a representative biologically active moiety into embodiments of the compounds of the present disclosure.

Alternatively, naproxen-NHS was reacted with 4-(aminomethoxy)butane-1,2,-diol and subsequently derivatized according to the reaction sequence shown above. The resultant final product of that reaction sequence afforded an alternative naproxen phosphoramidite with an extended linker relative to the naproxen phosphoramidite shown above.

Example 4

Exemplary Compounds Prepared Using Automated DNA Synthesis Method

Representative sequences were prepared with the ibuprofen-phosphoramidite and/or the naproxen-phosphoramidite described in Examples 2 and 3, respectively. Sequences were successfully prepared using automated DNA synthesis techniques, which are known in the art. Of the 10 representative constructs prepared, some were homogeneous (i.e., including only one biologically active moiety) while others were heterogeneous (i.e., included a combination of the two).

Other advantageous structural features were included in the representative embodiments synthesized according to this method. For example, Fluorescein was also easily and conveniently included in some of the constructs. Four of the compounds synthesized included a protected thiol moiety (C6SS) which was then used for attachment to a targeting moiety (e.g., an antibody) as described in Example 5. The representative compounds are summarized in Table 6, below.

TABLE 6

Exemplary polymer constructs prepared with ibuprofen-phosphoramidite and/or naproxen-phosphoramidite†

| Cpd. | Structure | MW Found Calc. |
|---|---|---|
| 1 | 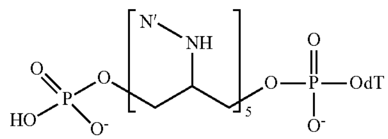 | 2068.9 / 2068.4 |
| 2 | 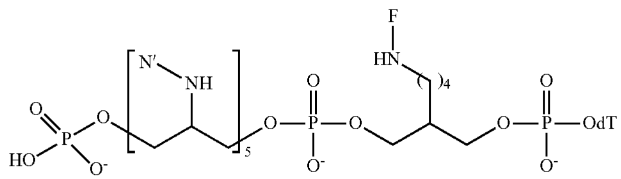 | 2636.4 / 2636.3 |
| 3 | | 2564.5 / 2588.7 |

TABLE 6-continued

Exemplary polymer constructs prepared with ibuprofen-phosphoramidite and/or naproxen-phosphoramidite[†]

| Cpd. | Structure | MW Found Calc. |
|---|---|---|
| 4 | | 4286.0 4286.3 |
| 5 | 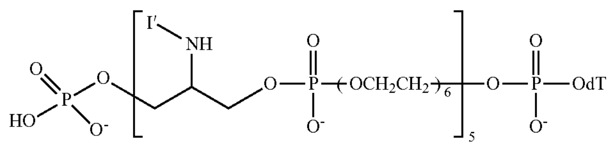 | 3670.5 3670.4 |
| 6 | 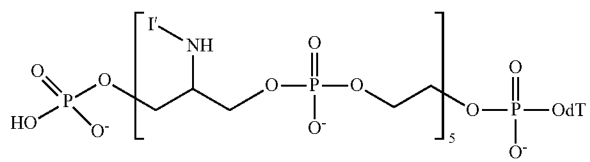 | 2569.3 2569.1 |
| 7 | 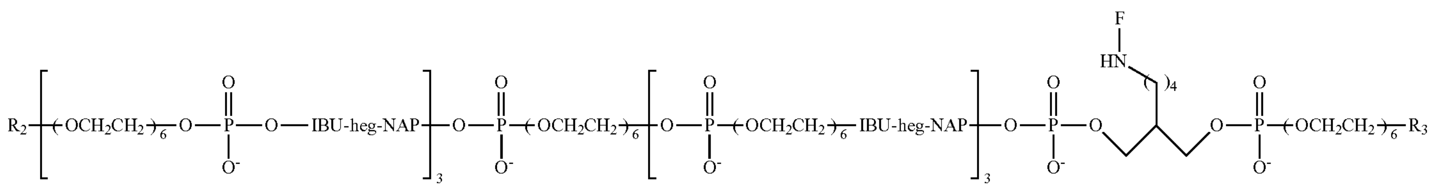 | 8803.2 8801.3 |

TABLE 6-continued

Exemplary polymer constructs prepared with ibuprofen-phosphoramidite and/or naproxen-phosphoramidite[†]

| Cpd. | Structure | MW Found Calc. |
|---|---|---|
| 8 | 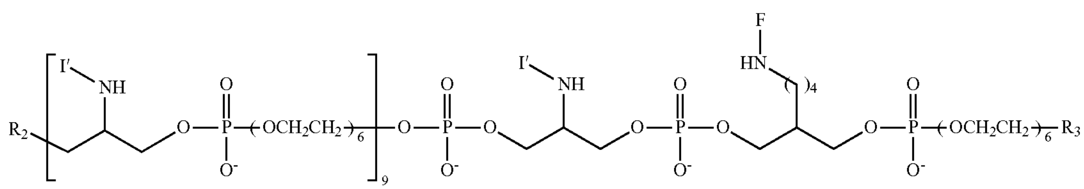 | 8339.0 8340.9 |
| 9 | 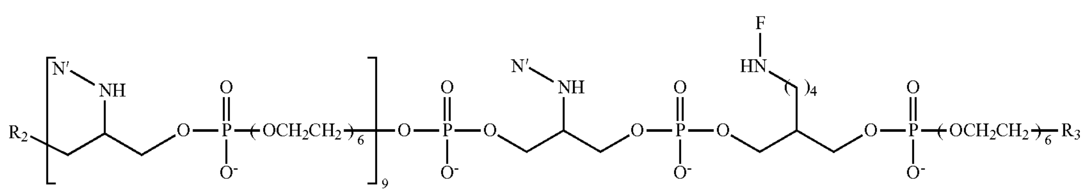 | 8578.8 8580.3 |

TABLE 6-continued
Exemplary polymer constructs prepared with ibuprofen-phosphoramidite and/or naproxen-phosphoramidite[†]
| Cpd. | Structure | MW Found Calc. |
|---|---|---|
| 10 | | 4982.6 4980.0 |
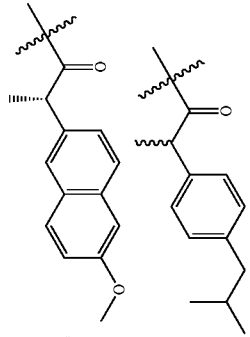

Example 5

Activation and Antibody Conjugation of Compound 7

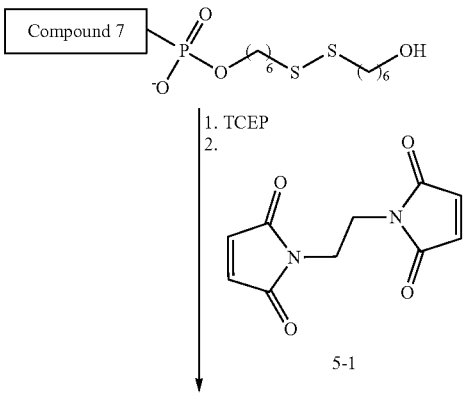

5-1

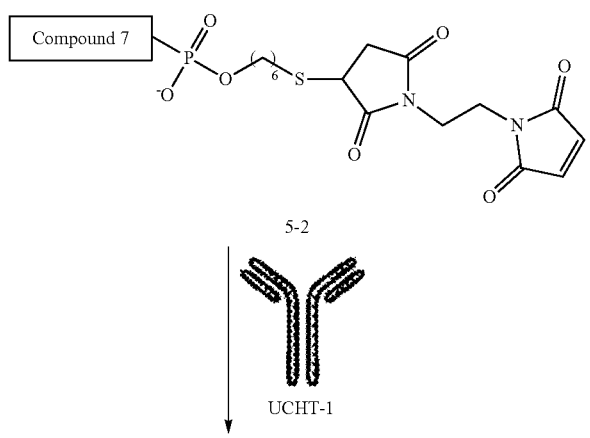

5-2

UCHT-1

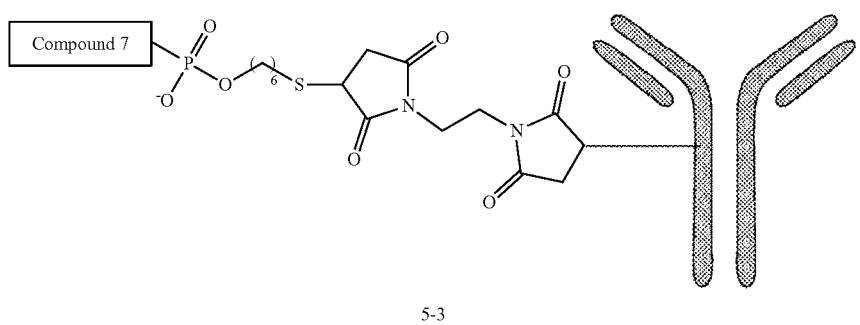

5-3

The thiol protecting group of Compound 7 was removed using standard reducing conditions (i.e., TCEP) and the deprotected thiol was functionalized with 5-1 (bis-maleimidoethane; "BMOE") to afford 5-2. In parallel, an UCHT-1 antibody was treated with BMOE to reduce disulfide bonds. The reduced antibody was reacted with 5-2 (1.5 g) in a 5:1 molar ratio of polymer to antibody. The reaction resulted in a final product, 5-3, having a polymer to antibody ratio of 1:1 as detected by size exclusion chromatography (FIG. 1).

Example 6

Synthesis of Compound 11

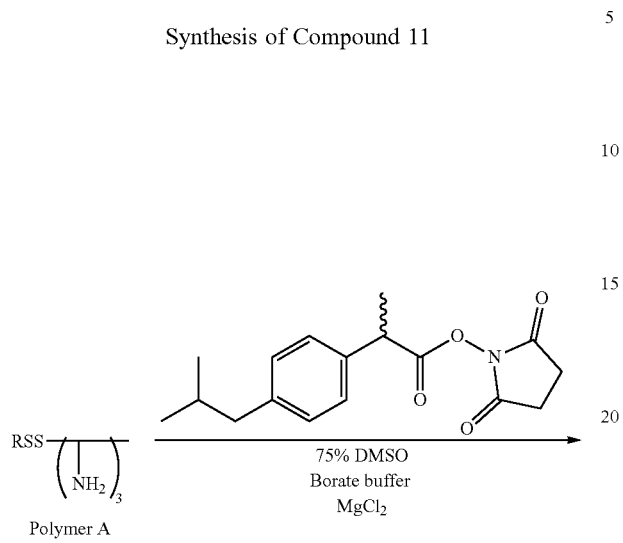

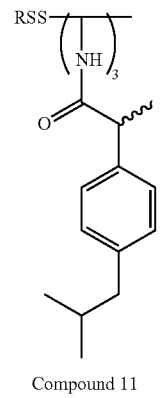

Compound 11

Polymer A, having 3 pendant amine functional groups, was coupled with ibuprofen-NHS as shown in the reaction sequence above (note—for clarity, not all structural features of Polymer A are drawn). The reaction was carried out using a borate buffered $H_2O$/DMSO mixture (1:3) with magnesium chloride. The reaction successfully added an ibuprofen moiety to each of the 3 amine functional groups to afford Compound 11 as identified by LC-MS (observed MW=4523.6). Two additional representative polymers were reacted under analogous reaction conditions to yield Compounds 12 and 13, respectively. The structures of Polymers A, B and C are shown in Table 7, below:

TABLE 7

Structures of reactive polymers used to couple with ibuprofen-NHS and resultant molecular weight of the final product as detected by LC-MS.

| Polymer | Structure |
|---|---|
| A | (structure shown) |
| B | (structure shown) |

TABLE 7-continued

Structures of reactive polymers used to couple with ibuprofen-NHS and resultant molecular weight of the final product as detected by LC-MS.

| Polymer | Structure |
|---|---|
| C | (structure shown) |

Example 8

Synthesis of Compound 14

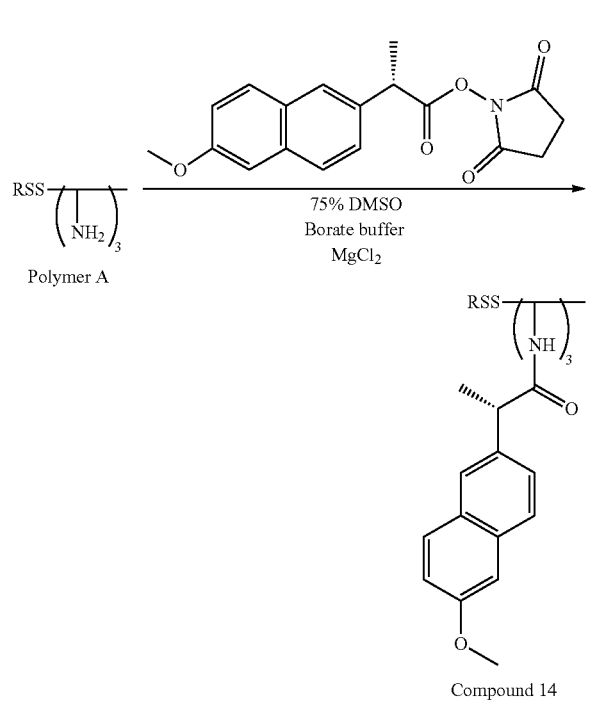

Compound 14

Polymer A was coupled to naproxen-NHS in the same manner as ibuprofen-NHS as described in Example 7. Naproxen-NHS was less reactive than ibuprofen-NHS, possible due to the differences in solubility; however the fully reacted polymer was successfully identified by LC-MS.

Reactions with naproxen-NHS and Reactive Polymers B and C also showed the desired products.

Example 9

Synthesis of Doxorubicin-NHS

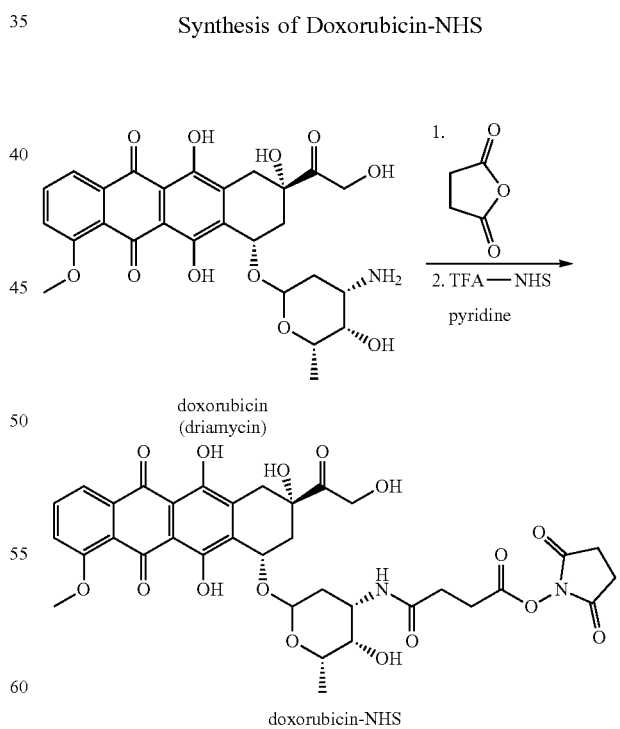

doxorubicin-NHS

Doxorubicin was reacted with dihydrofuran-2,5-dione to afford a carboxylic acid containing intermediate. The intermediate was activated using TFA-NHS and pyridine to afford doxorubicin-NHS.

Example 10

Synthesis of Doxorubicin Polymer (Compound 17)

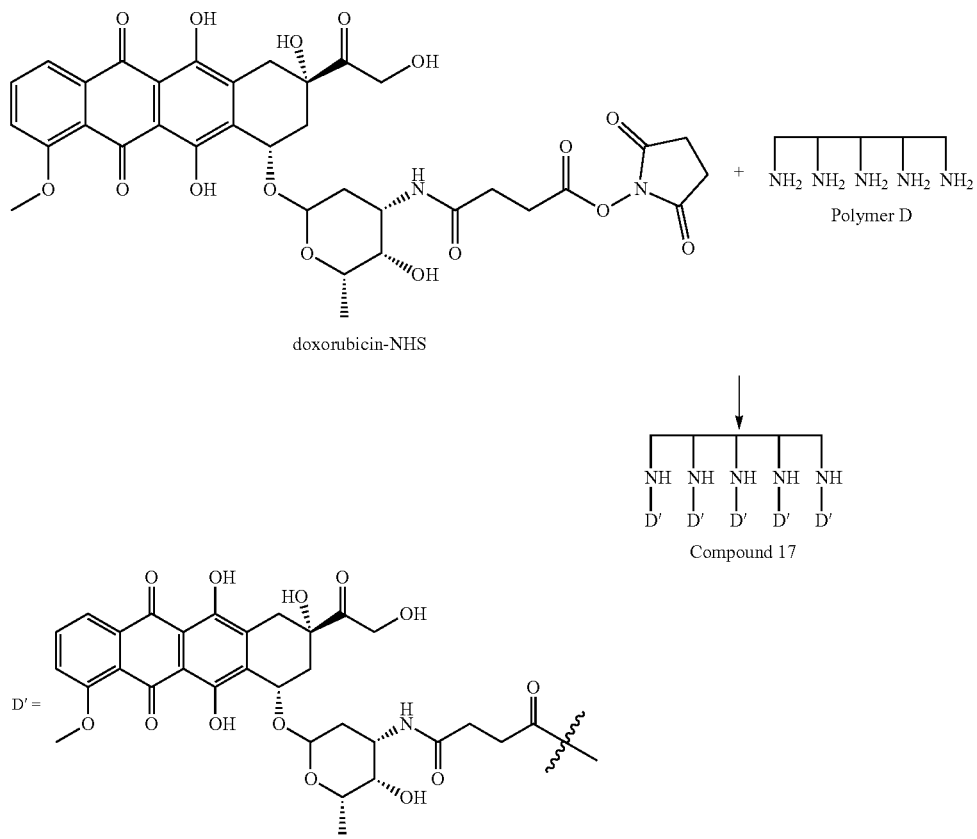

Polymer D having 5 pendant amine functional groups (structure shown below), was coupled to doxorubicin-NHS. Reaction conditions required experimentation because of the limited solubility of doxorubicin derivatives. Different reaction conditions were attempted, including increasing organic solvent content, increasing reaction temperature and adding sodium dodecyl sulfate (SDS) to aid the reaction.

The final reaction conditions were 100 mM borate buffer at pH 10, 500 mM magnesium chloride, 1% SDS, 75% DMSO. The reaction was held at 80° C. overnight. After heating overnight, the reaction was concentrated to dryness and reconstituted in water. The reconstituted mixture was desalted using micro-desalting columns and analyzed by PAGE and LC-MS.

Figure 2:
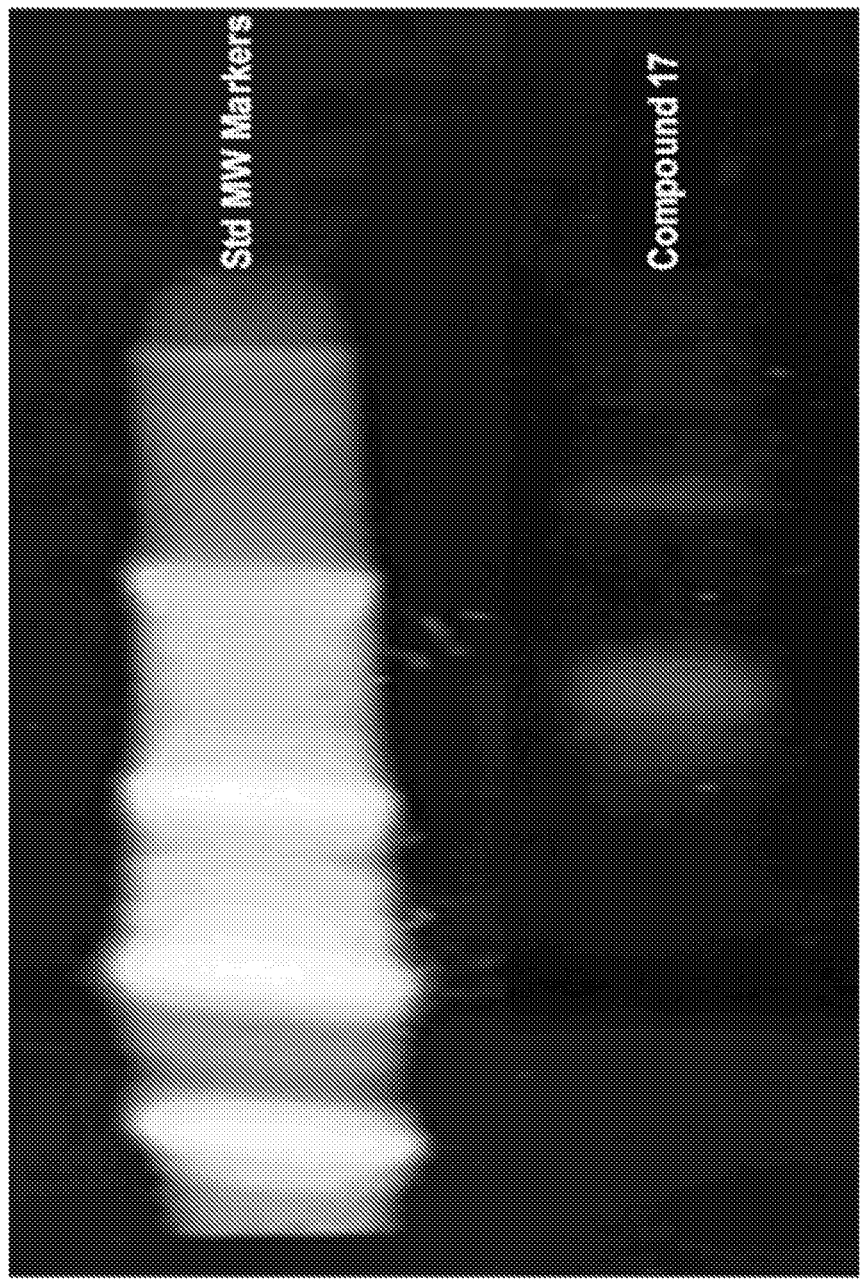
FIG. 2 shows the PAGE results of the synthesis of Compound 17.

PAGE analysis included visualization on a UV lamp at a wavelength of 365 nm (FIG. 2). The desired product was detected above the 5× standard and below the 10× standard, which is expected based on a calculated molecular weight for the desired product. The detected fluorescence is also consistent with the expected product. LC-MS analysis indicates a mixture of products.

| Polymer | Structure |
|---|---|
| D | 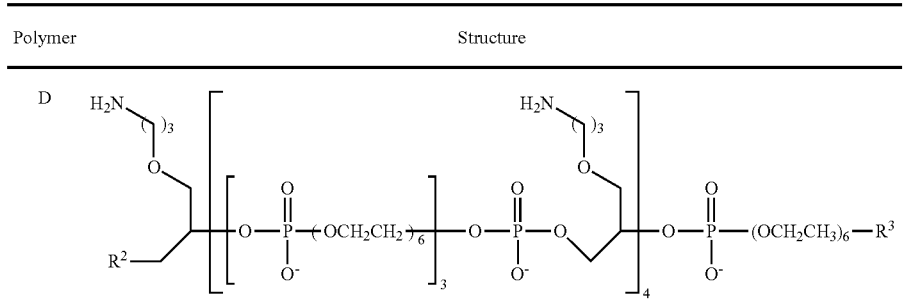 |

| Polymer | Structure |
|---|---|
| $R^2 =$ | 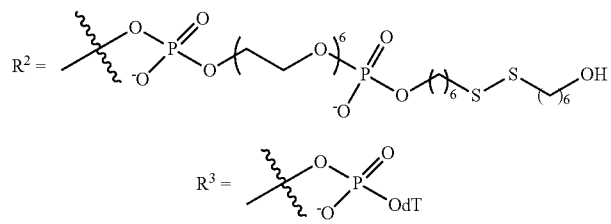 |
| $R^3 =$ | |
Example 11
Synthesis of Doxorubicin-PEG-Azide
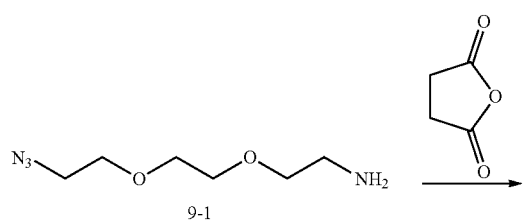
9-1
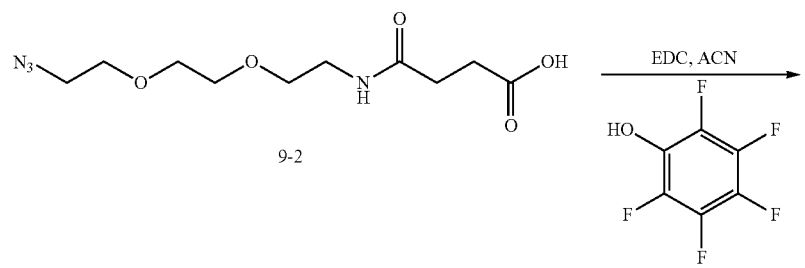
9-2
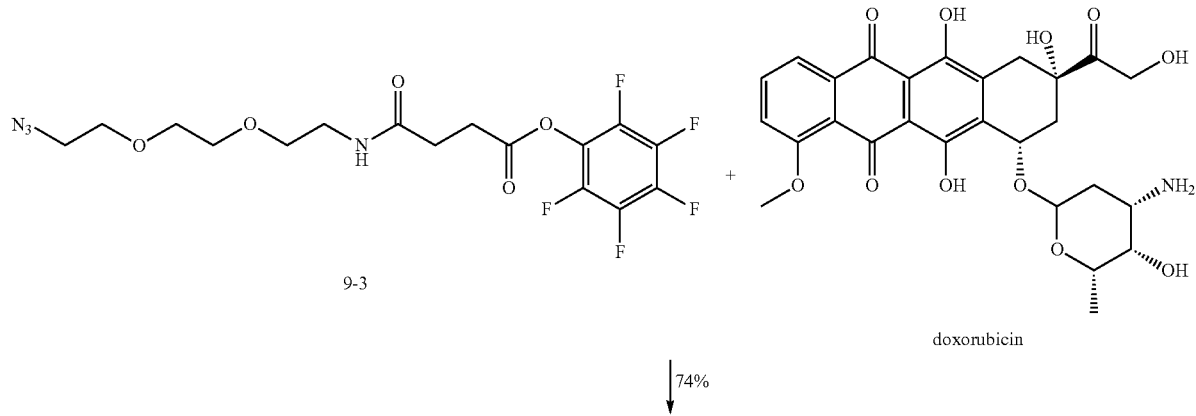
9-3
74%

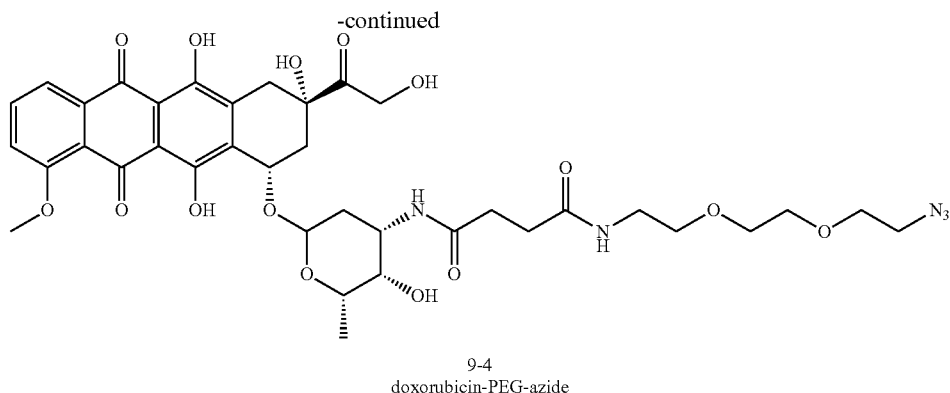

9-4
doxorubicin-PEG-azide

Doxorubicin-PEG-azide was synthesized according to the reaction sequence shown above on a 50 mg scale. Azide 9-1 was reacted with dihydrofuran-2,5-dione to afford intermediate 9-2, which was reacted with perfluorophenol to afford intermediate 9-3. Intermediate 9-3 was coupled to doxorubicin to afford the desired product, doxorubicin-PEG-azide in good yield (74%). The presence of the desired product was confirmed by LC-MS.

Example 12

Synthesis of Doxorubicin Polymer (Compound 18)

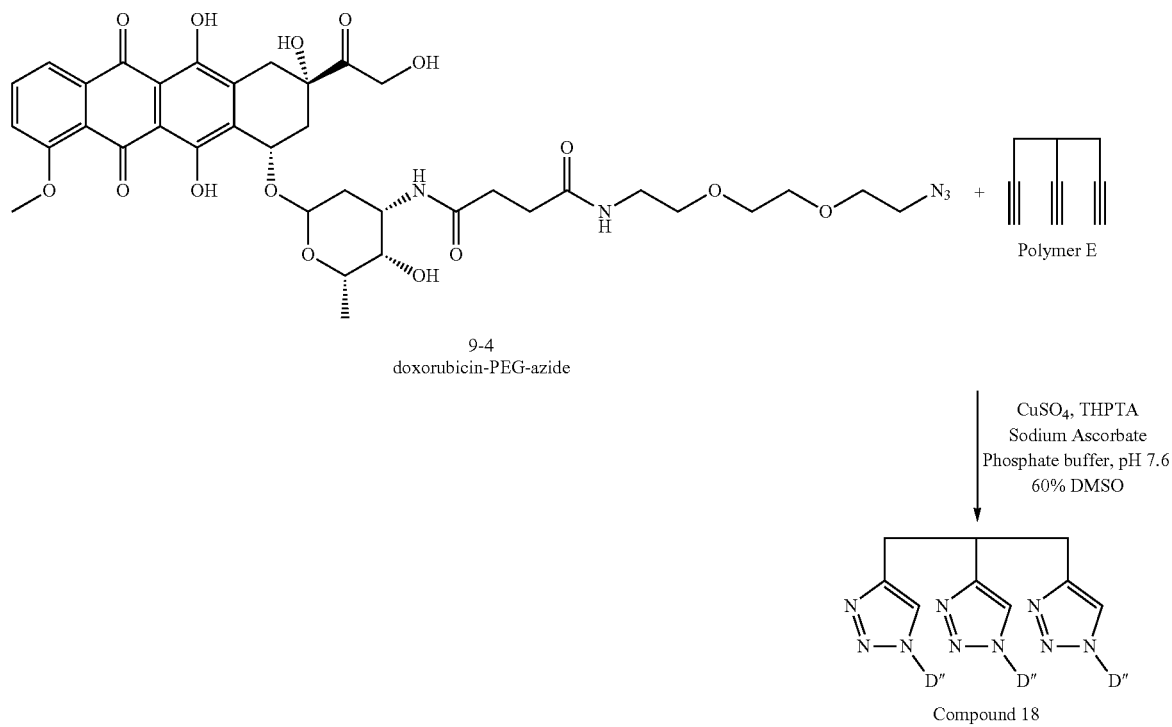

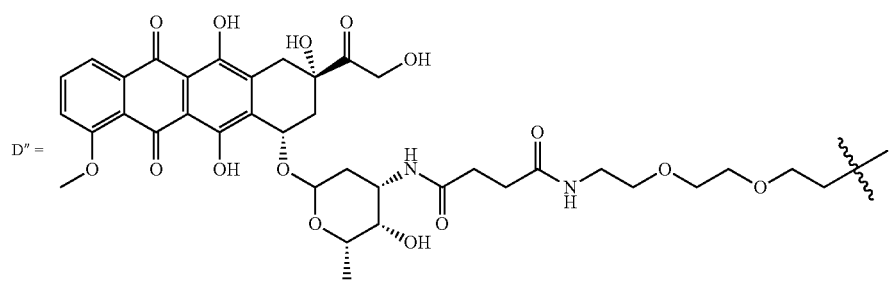

Polymer E having 3 pendant alkynyl functional groups (structure shown below), was coupled to doxorubicin-PEG-azide. Reaction conditions included CuSO$_4$, tris(3-hydroxypropyltriazolylmethyl)amine (THPTA), and sodium ascorbate. The reaction was carried out in phosphate buffered aqueous solvent with 60% DMS at a pH of 7.6. The reaction was run at room temperature and the presence of the desired product was confirmed by LC-MS.

and retention effects. In addition to providing necessary solubility characteristics, the chemical features of embodiments of the present compounds can be adjusted to modulate the compound's ability to permeate diseased cells/tissue and be retained within the same. These features allow effective delivery of biologically active agents by increasing permeation and increasing efficacy by enhancing retention.

| Polymer | Structure |
|---|---|
| E | 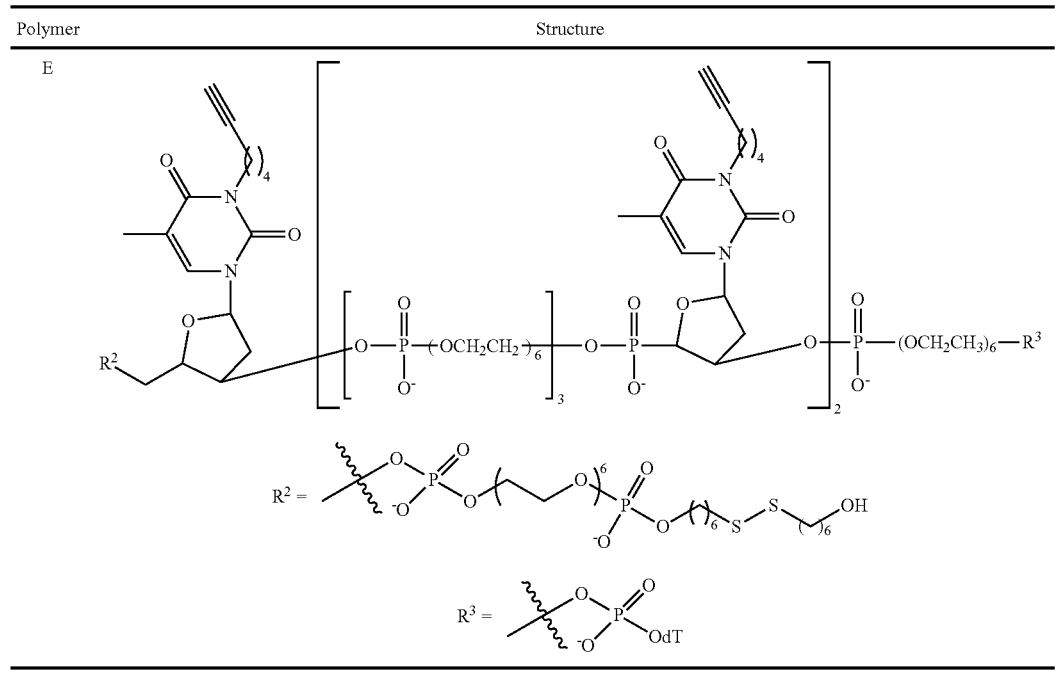 |

Numerous advantages are afforded by embodiments disclosed herein, including the ability to control the number of biologically active moieties or fluorescent dye moieties that are coupled to the polymer and any subsequent targeting moiety. The composition of the polymer backbone can also be selected to afford desirable solubility properties, for example, by controlling the incorporation of charged moieties (e.g., number, frequency, spacing, etc.). In addition to the properties provided by the composition of the backbone, the side chains can be selected to provide a source for tuning the solubility of the compounds disclosed herein.

The embodiments disclosed herein also provide compounds that can advantageously include multiple therapeutic agents, for example, for complimentary or synergistic therapeutic strategies. In addition, embodiments of the present disclosure provide combinations of therapeutic agents, targeting moieties, and dye moieties (e.g., fluorophores) that can be used for simultaneous targeting, treatment and detection. The ease of coupling polymer-drug constructs to targeting agents such as antibodies, antibody fragments, proteins or other clinically interesting agents provides utility to a wide variety of interesting applications (e.g., surface chemistries, assay development, etc.)

The compounds of certain embodiments also provide other desirable properties, including enhanced permeability Example 13

Potency Assay of Adc Made with Compound 19 and Herceptin

A series of antibody-polymer drug conjugates (ADCs) were tested for potency in a series of high expressing Her2 positive cell lines and compared to the potency and selectivity of the component parts of the antibody-polymer drug conjugate.

Cytotoxicity

Tumor cell cytotoxicity assays were conducted with tumor cell lines including PC3 (CRL-1435), SKBR3 (HTB-30), SKOV3 (HTB-77), and HCC1954 (CRL-2338), all obtained from ATCC. Tumor cell lines were plated in 96-well plates at 1,000 cells per well in RPMI medium (Life Technologies, Carlsbad Calif.) supplemented with 10% heat inactivated FCS, pyruvate, nonessential amino acids, and gentamicin.

Compound 19 was used for the polymer drug component and Herceptin was used as the antibody component. Auristatin F was used as the drug component and Compound A (i.e., Compound III-32 wherein M is F") was also used in the assay.

Figure 3:
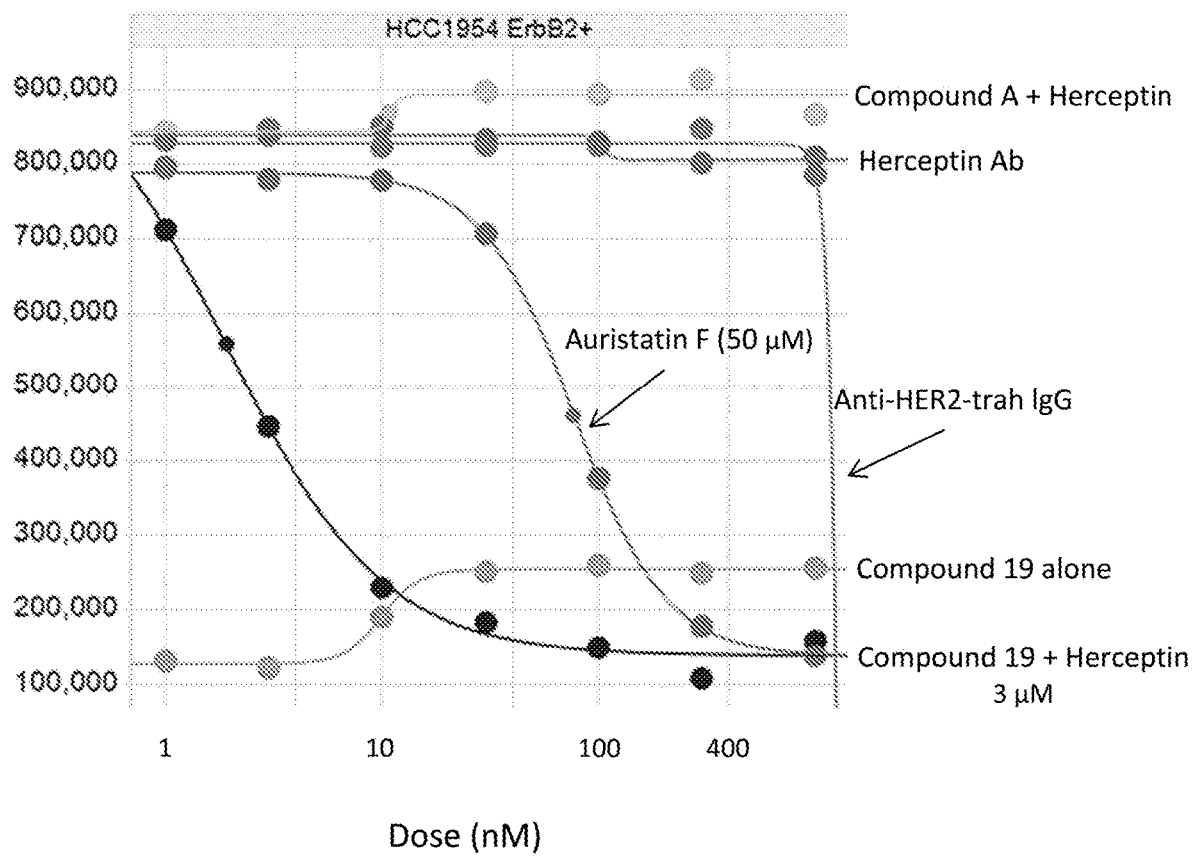
FIG. 3 shows results from the potency assay for HCC1954 cells as described in Example 13.
Figure 4:
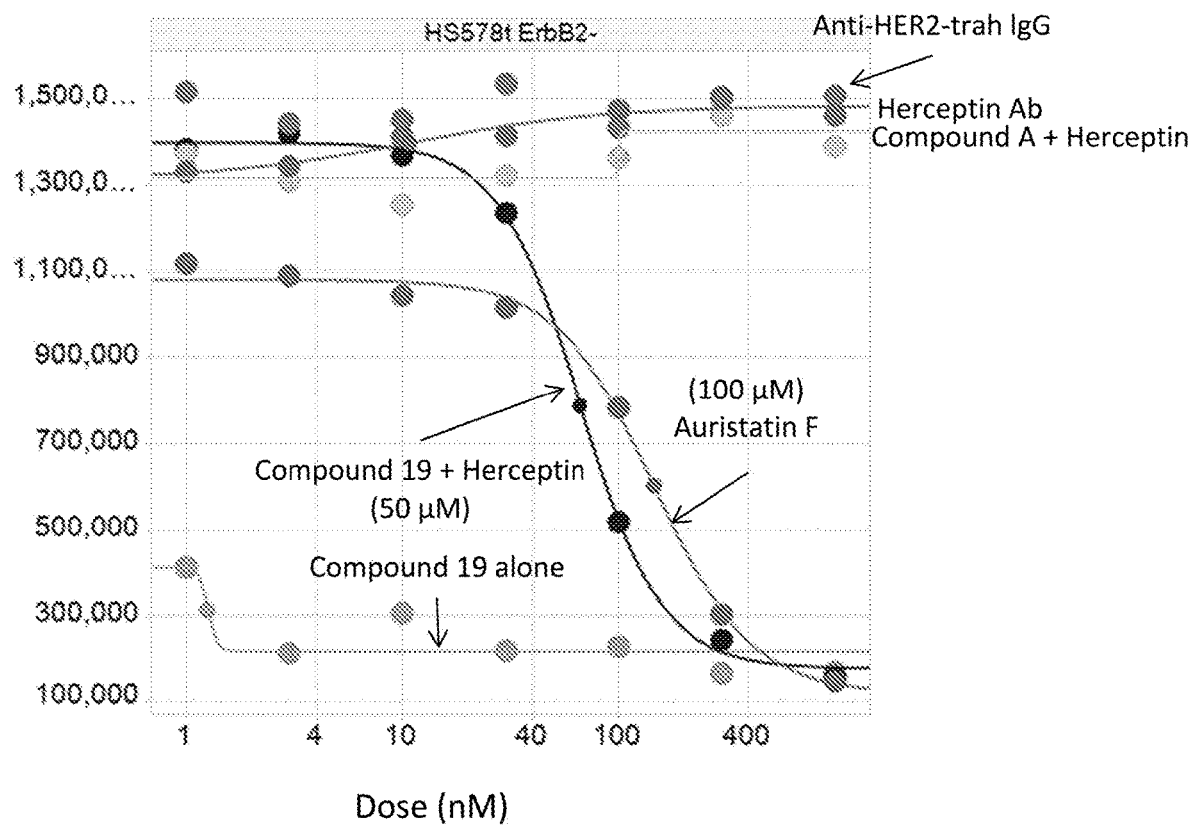
FIG. 4 shows results from the potency assay for HS578 cells as described in Example 13.
Figure 5:
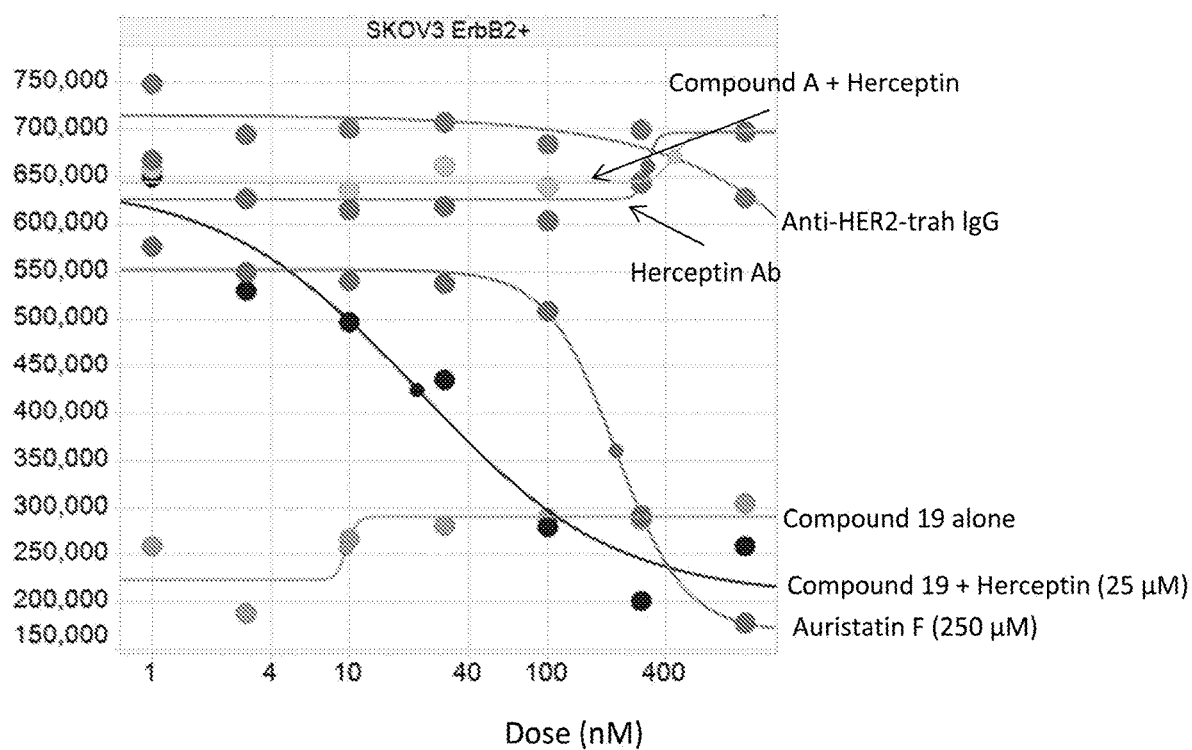
FIG. 5 shows results from the potency assay for SKO3 cells as described in Example 13.

For each assay growth inhibition was assessed in duplicate samples by incubating ADCs with the tumor cell lines for 72 hours followed by treatment with Alamar blue (Life Technologies) for 1-4 hours. The fluorescence emission at 590 nm (excitation between 530-560 nm) of reduced resazurin was quantified using a molecular diagnostics plate reader. Each assay was conducted in duplicate, the data log transformed, and average values plotted on a semi-logarithmic scale graph. The half-maximal effective concentration ($EC_{50}$) for each treatment was calculated using a non-linear least squares fit to a four parameter logistic equation using Prism version 6 software (GraphPad Software Inc, San Diego Calif.). The average and standard deviation of $EC_{50}$ were generated and averages are shown in FIGS. 3-5. The results for HCC1954, and SKOV3 are shown in FIGS. 3 and 5, respectively. Results for HS578t ErbB2- are shown in FIG. 4.

The results show that the ADC is more potent than the drug alone, which seems to be partially dependent on the cell type. Additionally, the polymer-drug component is more potent than the drug alone or the ADC. This may be due to a concentration effect (e.g., 1 nM of polymer drug=5 nM drug) but is not solely explained by concentration. Without wishing to be bound by theory, it is thought that the auristatin F is loaded at the C-terminal position of the drug, which eliminates the carboxylate charge and increases potency. Additionally, it does appear that the polymer alone is permeating the cell.

All of the U.S. patents, U.S. patent application publications, U.S. patent applications, foreign patents, foreign patent applications and non-patent publications referred to in this specification, including U.S. Provisional Patent Application No. 62/568,706, filed on Oct. 5, 2017, are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure (IA):

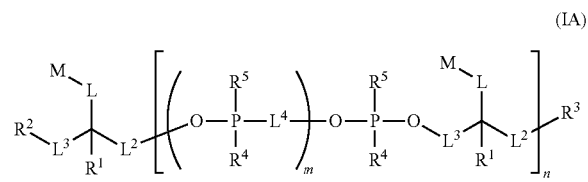

(IA)

or a stereoisomer, pharmaceutically acceptable salt or tautomer thereof, wherein:

M is, at each occurrence, independently a biologically active moiety selected from an NSAID, a kinase inhibitor, an anthracycline, an EGFR inhibitor, an alkylating agent, and anti-cancer drug; or a fluorescent dye, provided at least one occurrence of M is not a fluorescent dye;

L is a physiologically cleavable linker;

$L^2$ and $L^3$ are, at each occurrence, independently absent or an alkylene, alkenylene, alkynylene, heteroalkylene, heteroalkenylene, heteroalkynylene or heteroatomic linker;

$L^4$ is, at each occurrence, independently an alkylene, alkenylene, alkynylene, heteroalkylene, heteroalkenylene or heteroalkynylene linker;

$R^1$ is, at each occurrence, independently H, alkyl or alkoxy;

$R^2$ and $R^3$ are each independently OH, SH, alkyl, alkoxy, alkylether, heteroalkyl, —OP(=$R_a$)($R_b$)$R_c$, Q, or a protected form thereof, or L';

$R^4$ is, at each occurrence, independently OH, SH, O$^-$, S$^-$, $OR_d$ or $SR_d$;

$R^5$ is, at each occurrence, independently oxo, thioxo or absent;

$R_a$ is O or S;

$R_b$ is OH, SH, O$^-$, S$^-$, $OR_d$ or $SR_d$;

$R_c$ is OH, SH, O$^-$, S$^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with a complementary reactive group Q' on a targeting moiety;

L' is, at each occurrence, independently a linker comprising a covalent bond to Q, a targeting moiety, a linker comprising a covalent bond to a targeting moiety, a linker comprising a covalent bond to a solid support, a linker comprising a covalent bond to a solid support residue, a linker comprising a covalent bond to a nucleoside or a linker comprising a covalent bond to a further compound of structure (IA);

m is, at each occurrence, independently an integer of zero or greater; and n is an integer of one or greater.

2. The compound of claim 1, wherein $L^4$ is ethylene oxide or polyethylene oxide, and the compound has the following structure (IB):

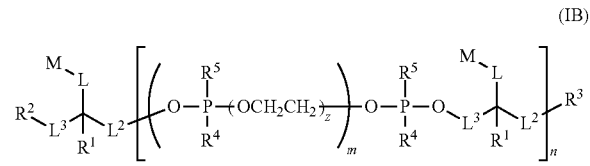

(IB)

wherein z is an integer from 1 to 100.

3. The compound of claim 1, wherein the compound has the following structure (IC):

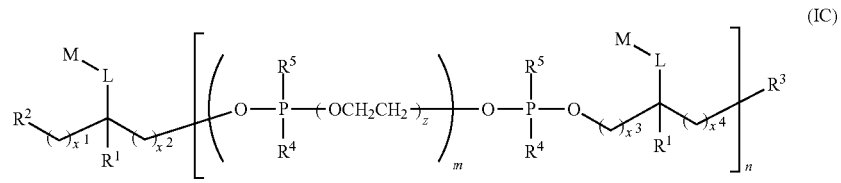

(IC)

wherein:

$x^1$, $x^2$, $x^3$ and $x^4$ are, at each occurrence, independently an integer from 0 to 6; and z is an integer from 1 to 100.

4. The compound of claim 1, wherein the compound has the following structure (ID):

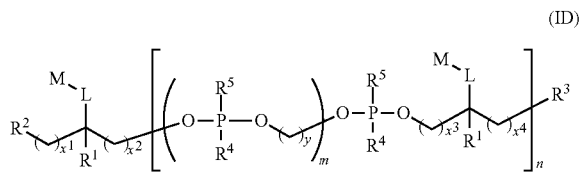

(ID)

wherein:

$x^1$, $x^2$, $x^3$ and $x^4$ are, at each occurrence, independently an integer from 0 to 6; and y is an integer from 1 to 6.

5. The compound of claim 4, wherein y is 2, and $x^1$, $x^2$, $x^3$ and $x^4$ are each 1 at each occurrence.

6. The compound of claim 1, wherein $R^4$ is, at each occurrence, independently OH, O⁻ or $OR_d$, $R^5$ is, at each occurrence, oxo, and $R^1$ is, at each occurrence, H.

7. The compound of claim 1, wherein $R^2$ and $R^3$ are each independently OH or —OP(=$R_a$)($R_b$)$R_c$.

8. The compound of claim 1, wherein one of $R^2$ and $R^3$ is OH or —OP(=$R_a$)($R_b$)$R_c$, and the other of $R^2$ and $R^3$ is Q or a linker comprising a covalent bond to Q.

9. The compound of claim 1, wherein one of $R^2$ and $R^3$ is —OP(=$R_a$)($R_b$)$R_c$ or L'.

10. The compound of claim 9, wherein $R_c$ is OL', wherein L' is a targeting moiety or a linker to a targeting moiety, the linker comprising an alkylene oxide or phosphodiester moiety, or combinations thereof.

11. The compound of claim 10, wherein L' has the following structure:

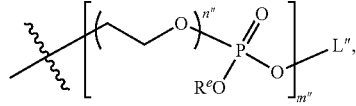

wherein:

m" and n" are independently an integer from 1 to 10;
$R^c$ is H, an electron pair or a counter ion; and
L" is the targeting moiety or a linkage to the targeting moiety.

12. The compound of claim 1, wherein the targeting moiety is an antibody or cell surface receptor antagonist, wherein the antibody or cell surface receptor antagonist is an epidermal growth factor receptor (EGFR) inhibitor, a hepatocyte growth factor receptor (HGFR) inhibitor, an insulin-like growth factor receptor (IGFR) inhibitor, a folate, or a MET inhibitor.

13. The compound of claim 1, wherein $R^2$ or $R^3$ has one of the following structures:

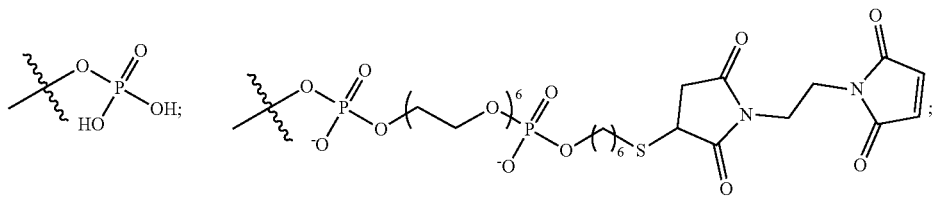

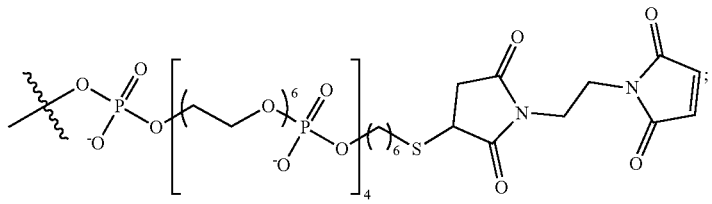

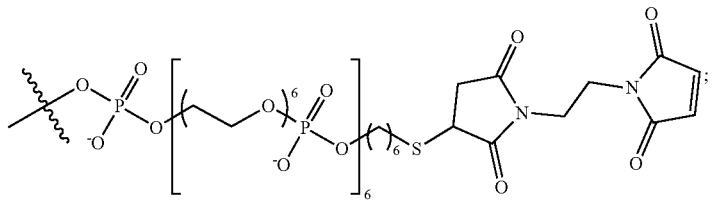

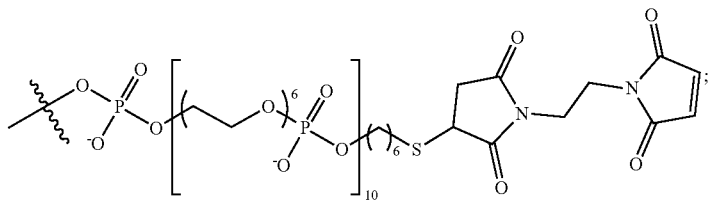

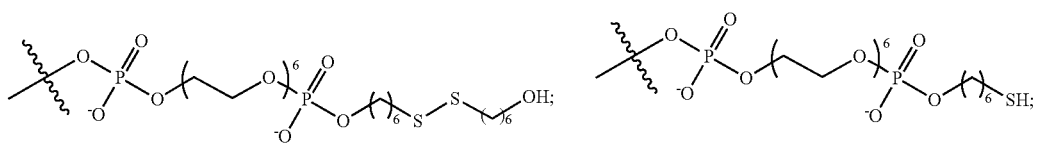

-continued

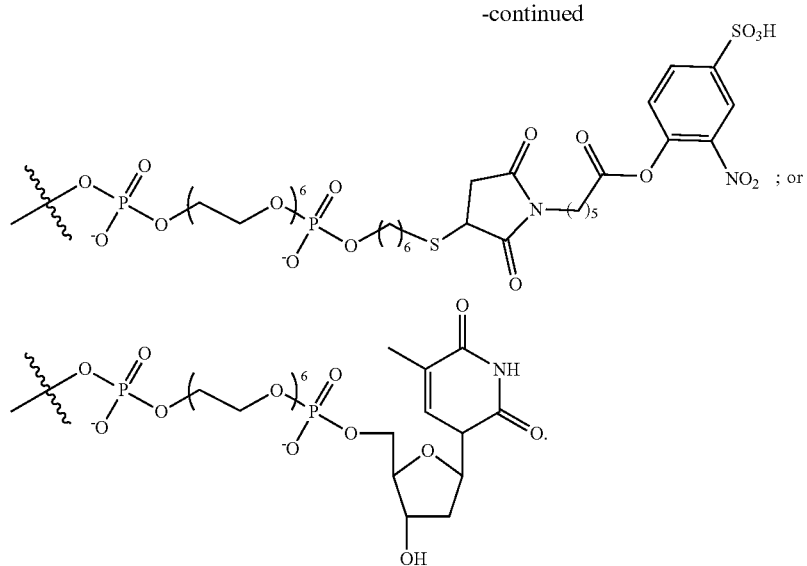

14. The compound of claim 1, wherein L is, at each occurrence, independently a linker comprising an amide bond, an ester bond, a disulfide bond, a double bond, a triple bond, an ether bond, a ketone, a diol, a cyano, a nitro or combinations thereof.

15. The compound of claim 1, wherein M is, at each occurrence, independently an anti-cancer drug, and the targeting moiety is an antibody specific for a tumor cell antigen, wherein the tumor cell antigen is an EGFR, a HER 2, a folate receptor, CD20 or CD 33.

16. The compound of claim 1, wherein at least one occurrence of M has one of the following structures:

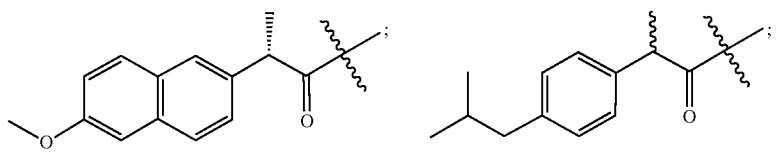

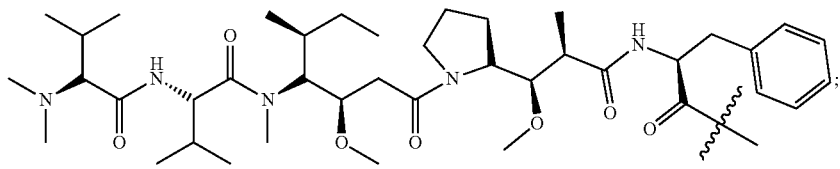

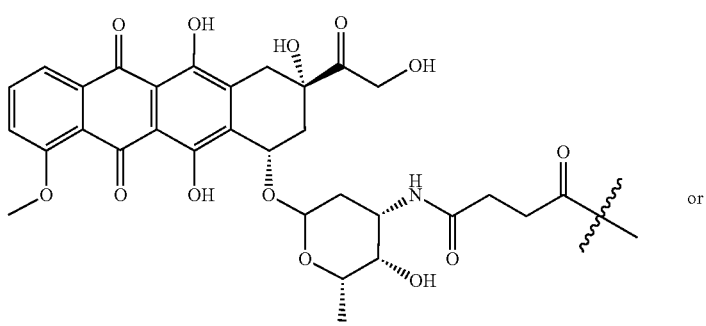

-continued
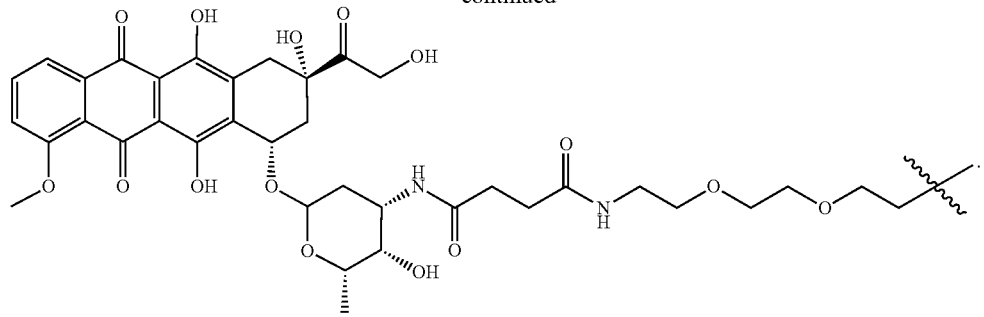
15
17. The compound of claim 1, wherein the compound has one of the following structures:
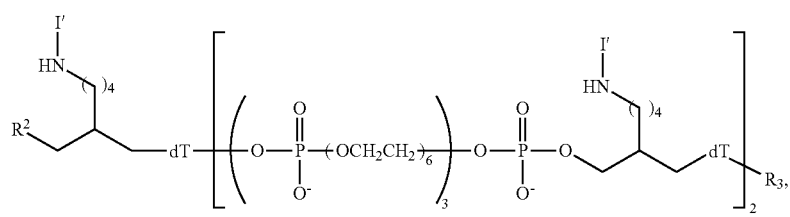
wherein:
R² has the following structure:
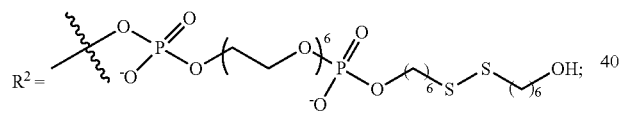
and
R³ has the following structure:
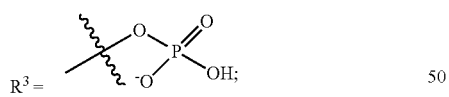
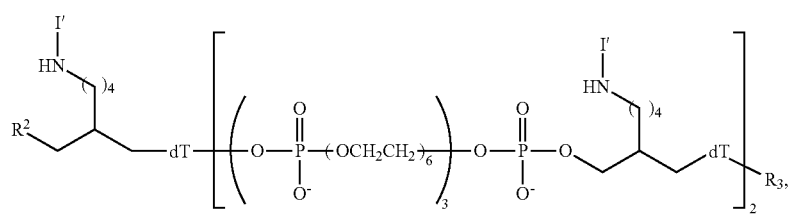

wherein:
$R^2$ has the following structure:
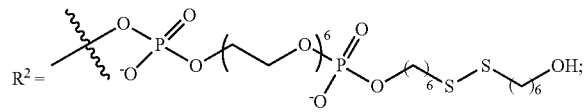
and
$R^3$ has the following structure:
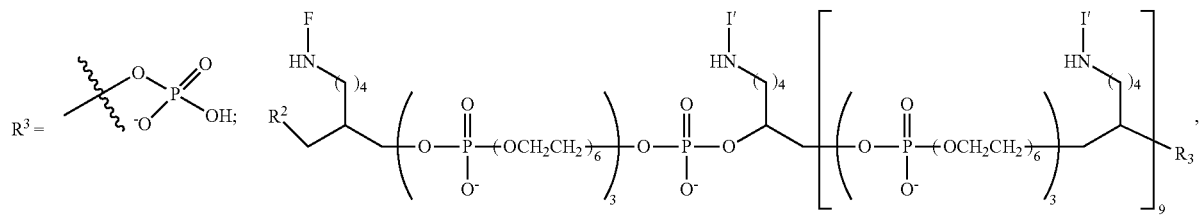
wherein:
$R^2$ has the following structure:
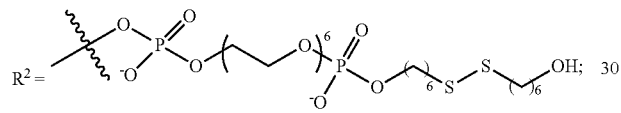
and
$R^3$ has the following structure:
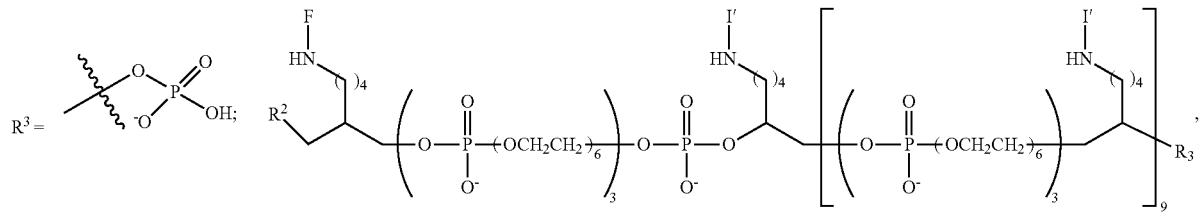
wherein:
$R^2$ has the following structure:
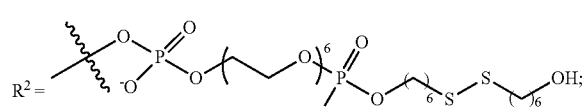
and
$R^3$ has the following structure:
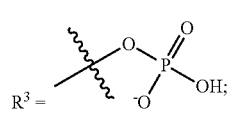
-continued
wherein $R^2$ has the following structure:

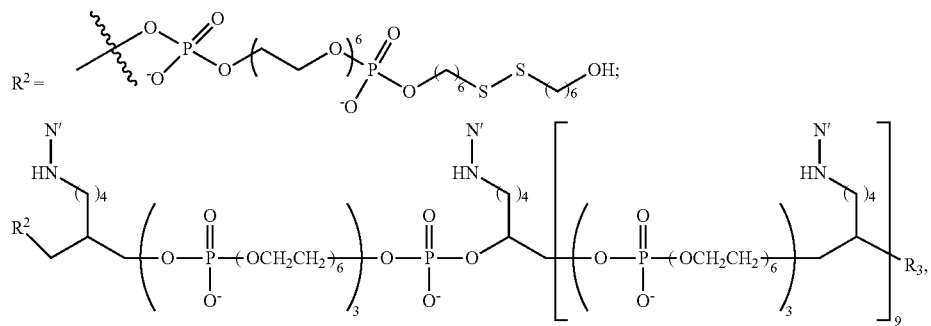
wherein:
R² has the following structure:
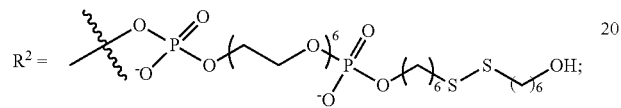
and
R³ has the following structure
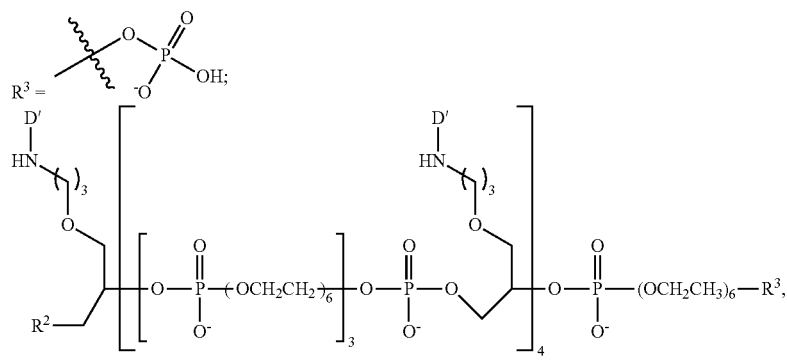
wherein:
R² has the following structure:
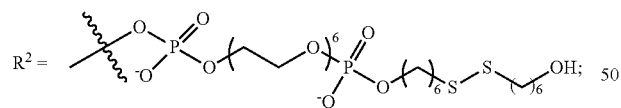
and
R³ has the following structure:
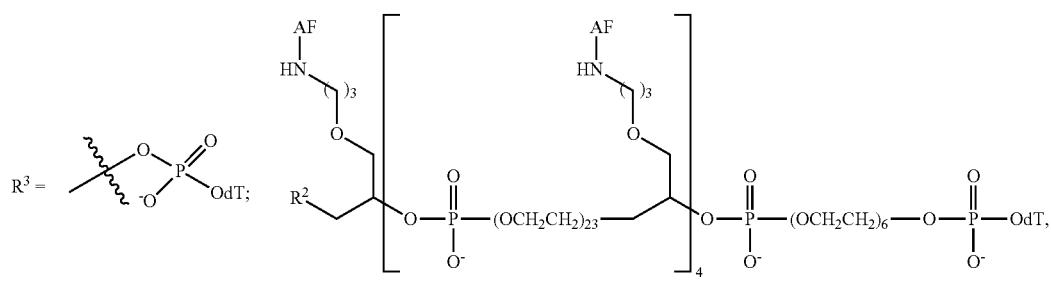

wherein R² has the following structure:
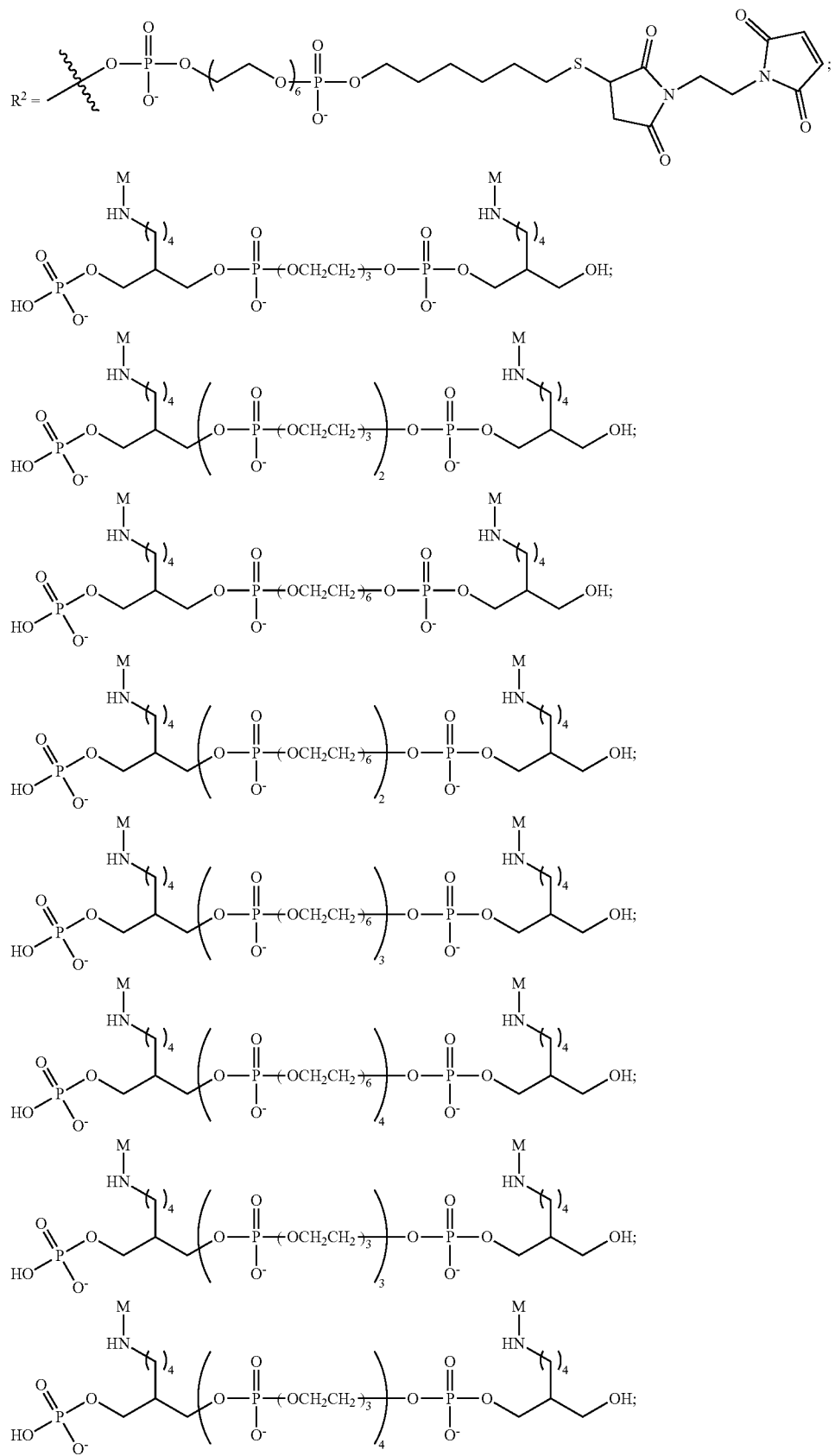

-continued
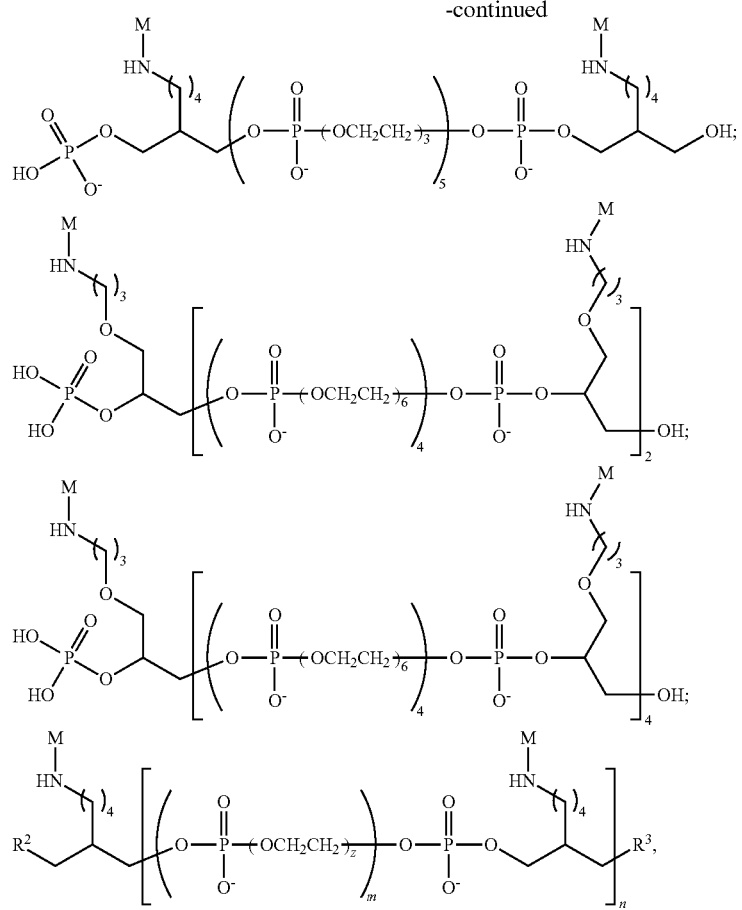
wherein:
z is 3, 4, 5, or 6;
m is 2, 3, 4, or 5; and
n is 1-10;
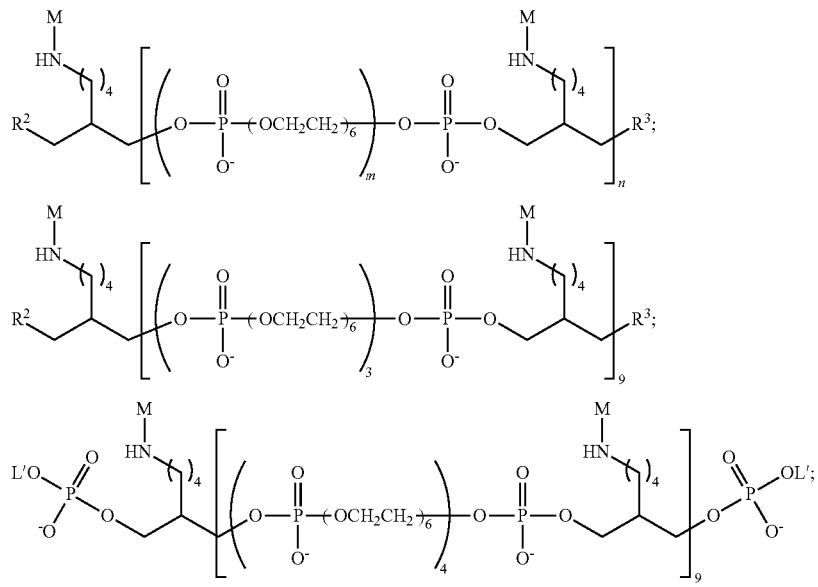

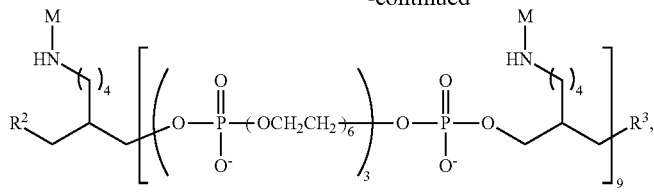
wherein:
R² has the following structure:
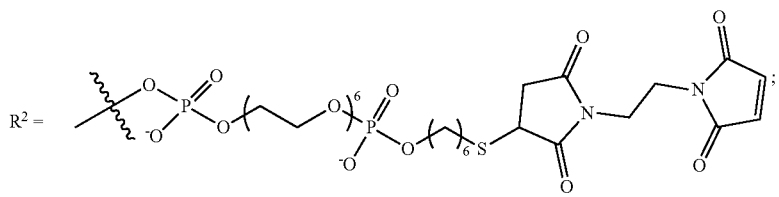
and
R³ has the following structure:
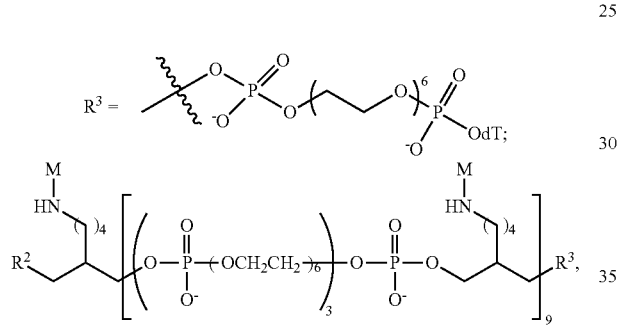
wherein:
R² has the following structure:
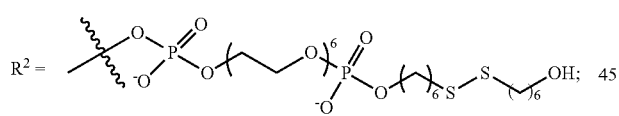
and
R³ has the following structure:
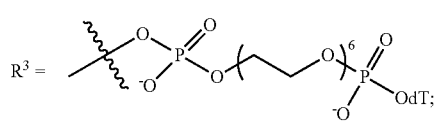
-continued
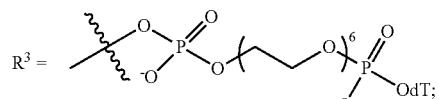
wherein:
R² has the following structure:
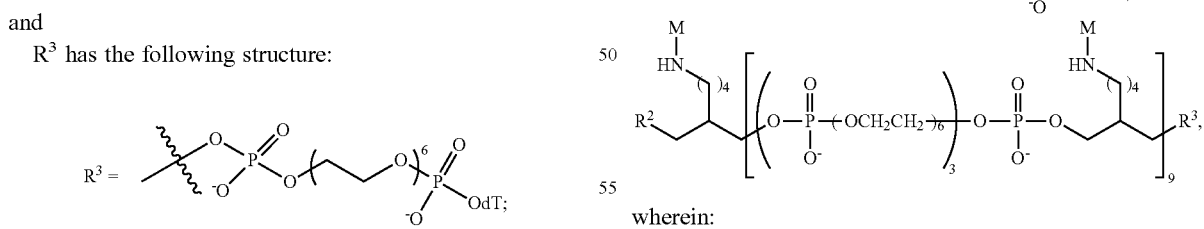
and
R³ has the following structure:
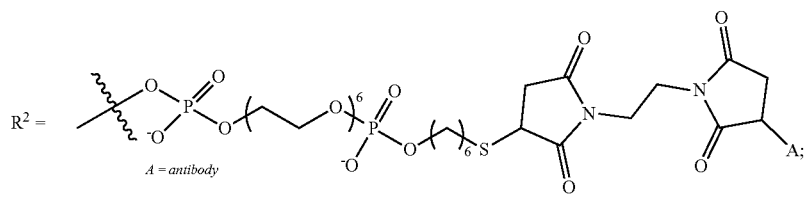
wherein:
R² has the following structure:
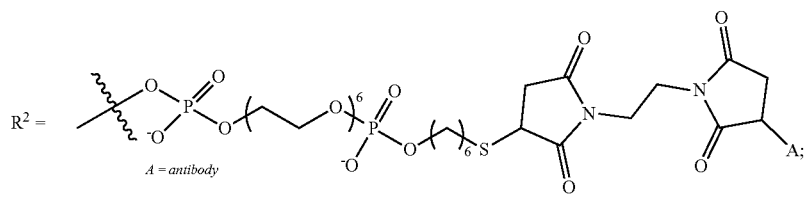
A = antibody and
R³ has the following structure:
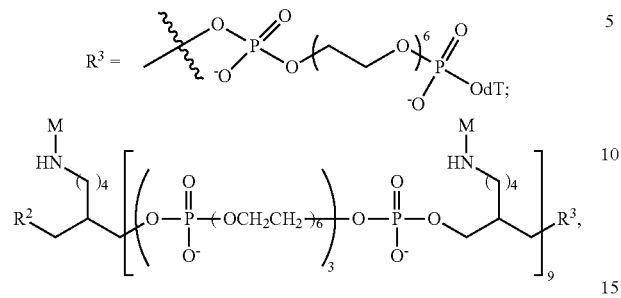
wherein:
R² has the following structure:
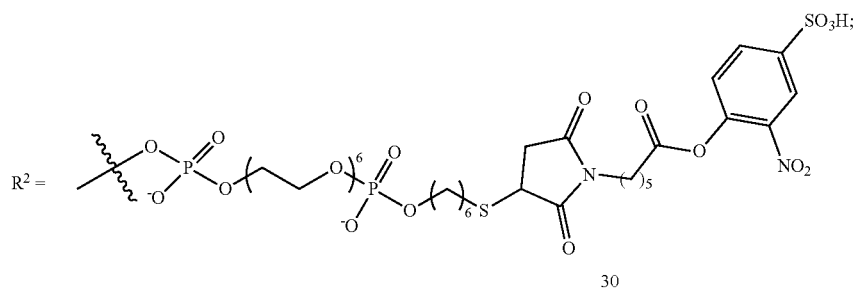
and
R³ has the following structure:
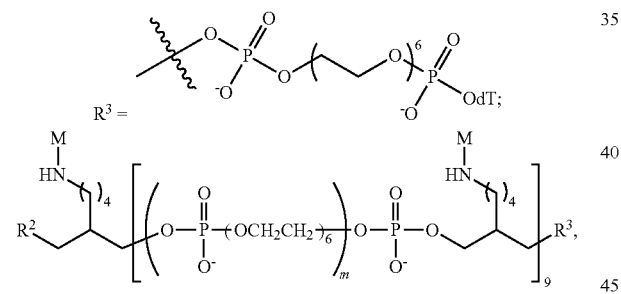
wherein:
R² has the following structure:
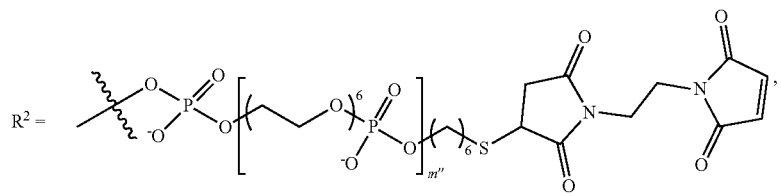
m" is 4 or 10; and
R³ has the following structure:
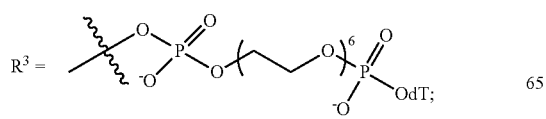

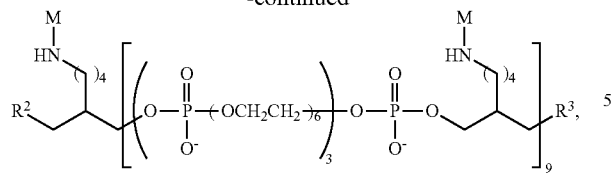 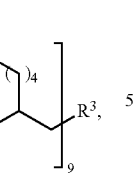
wherein:
R² has the following structure:
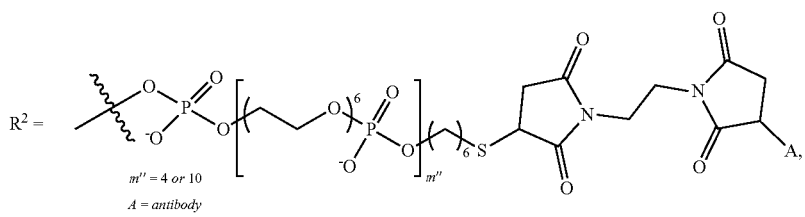
m" is 4 or 10; and
R³ has the following structure:
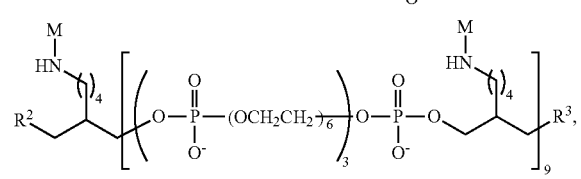
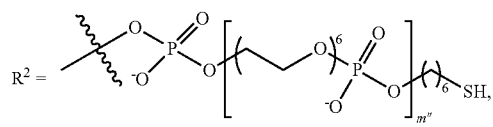
wherein:
R² has the following structure:
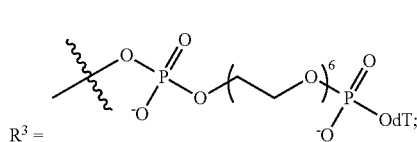
m" is 4 or 10; and
R³ has the following structure:
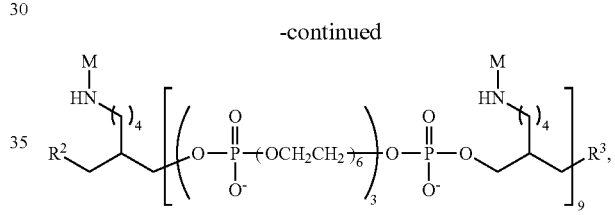
wherein:
R² has the following structure:
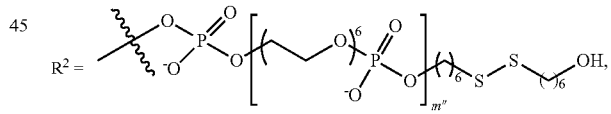
m" is 4 or 10; and
R³ has the following structure:
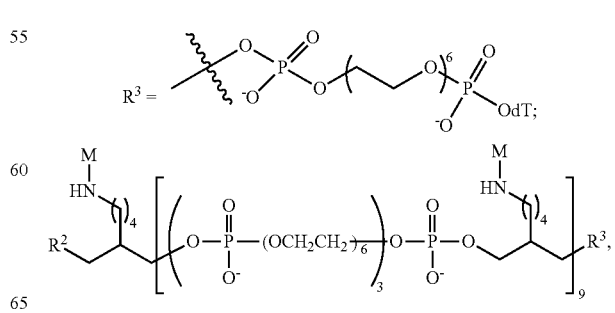

wherein:
R² has the following structure:
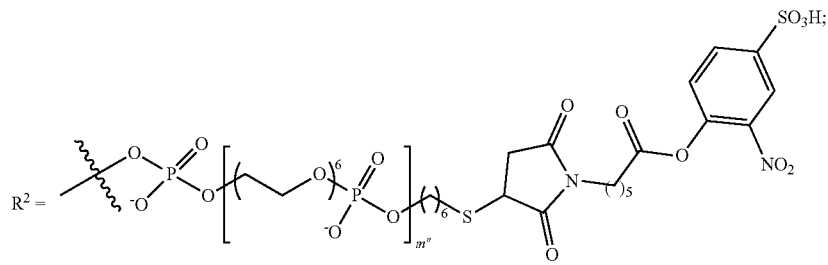
m" is 4 or 10; and
R³ has the following structure:
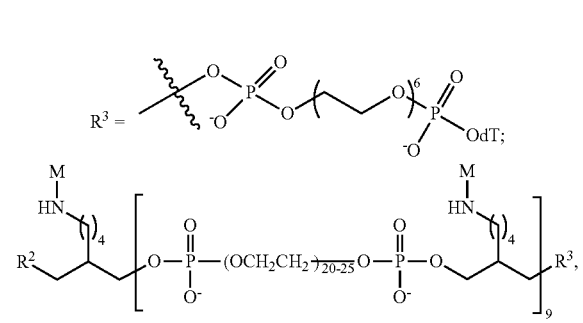
wherein:
R² has the following structure:
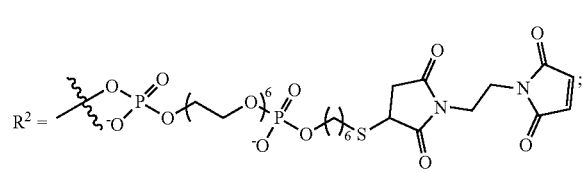
and
R³ has the following structure:
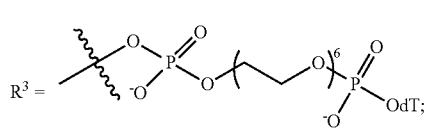
-continued
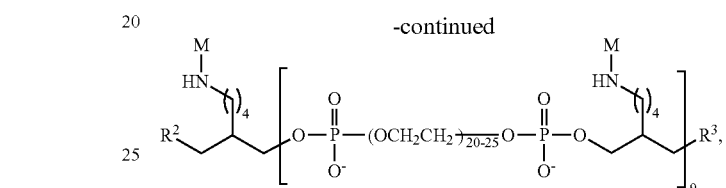
wherein:
R² has the following structure:
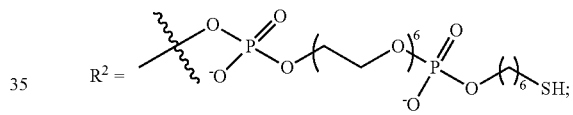
and
R³ has the following structure:
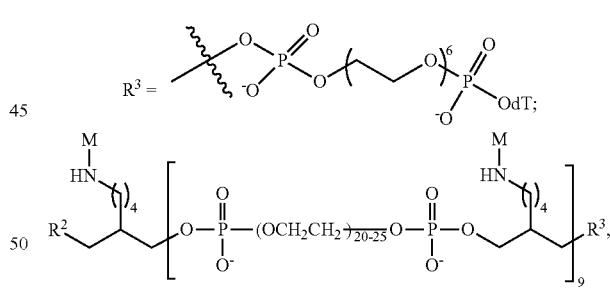
wherein:
R² has the following structure:
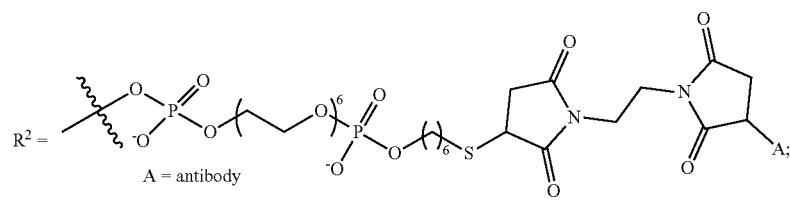
A = antibody and
R³ has the following structure:
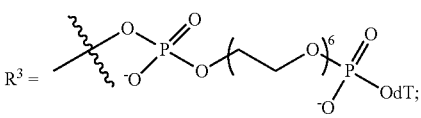
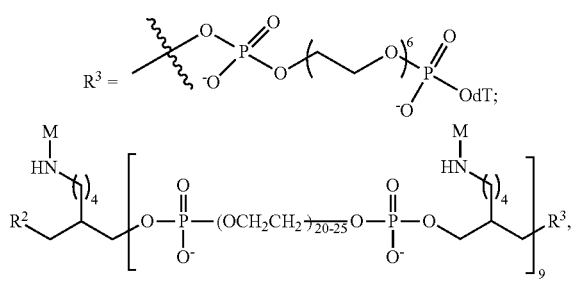
wherein:
R² has the following structure:
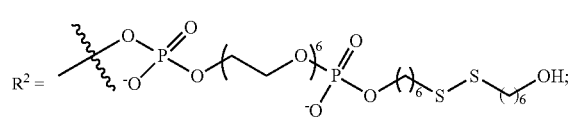
and
R³ has the following structure:
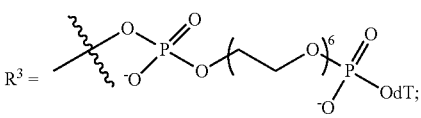
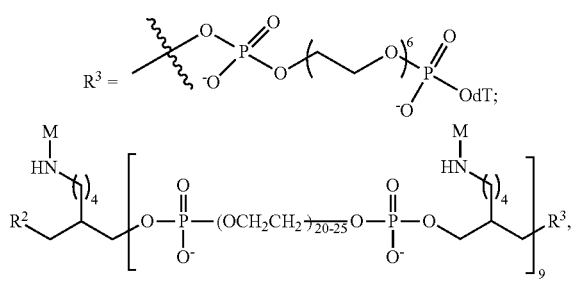
wherein:
R² has the following structure:
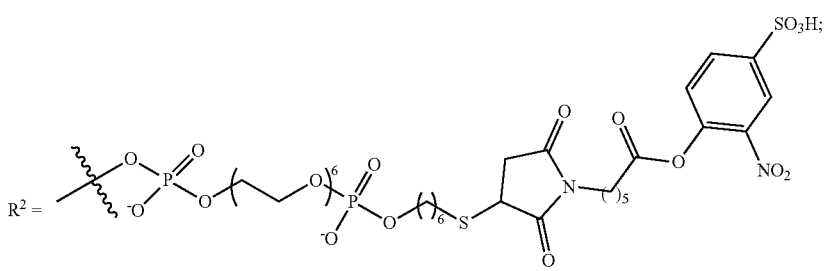
and
R³ has the following structure:
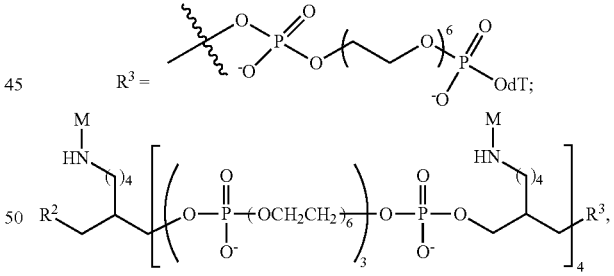
wherein:
R² has the following structure:
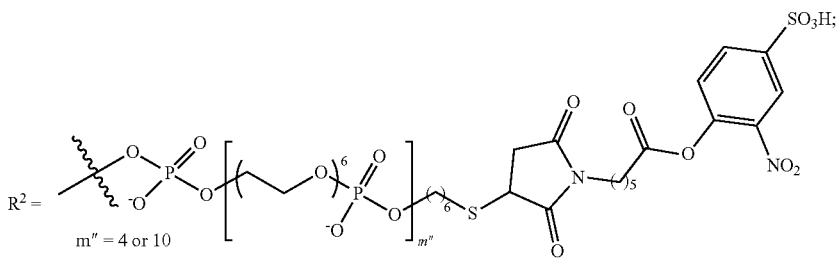

and
R³ has the following structure:
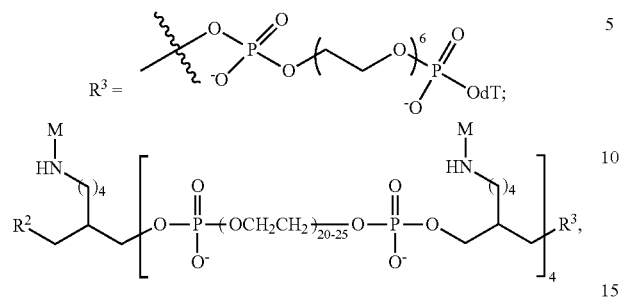
wherein:
R² has the following structure:
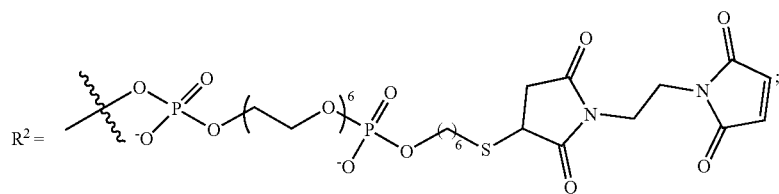
and
R³ has the following structure:
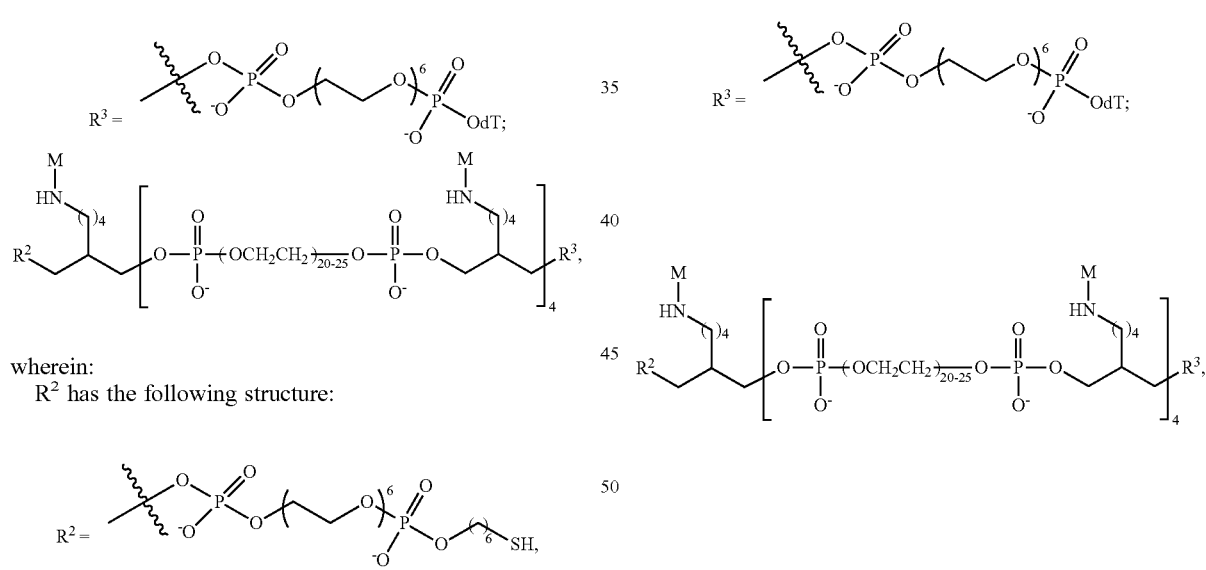
wherein:
R² has the following structure:
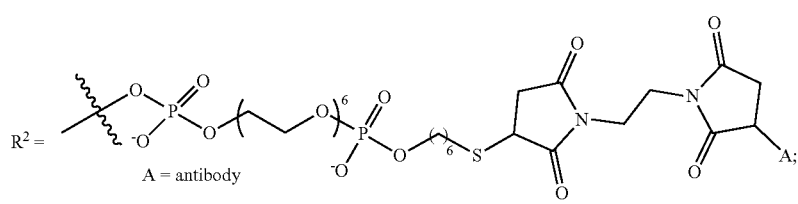
A = antibody and
R³ has the following structure:
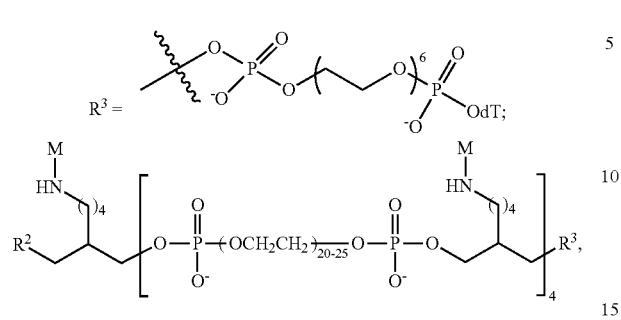
wherein:
R² has the following structure:
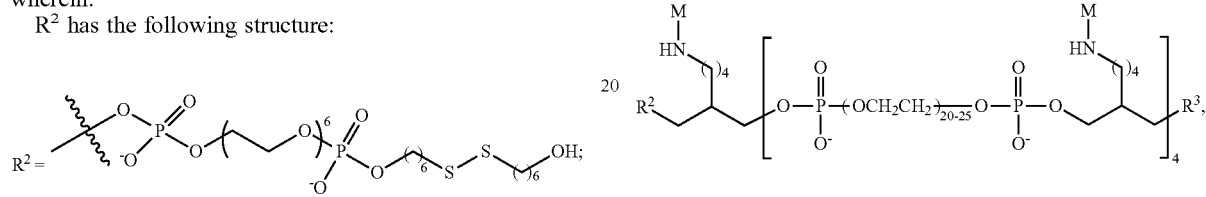
and
R³ has the following structure:
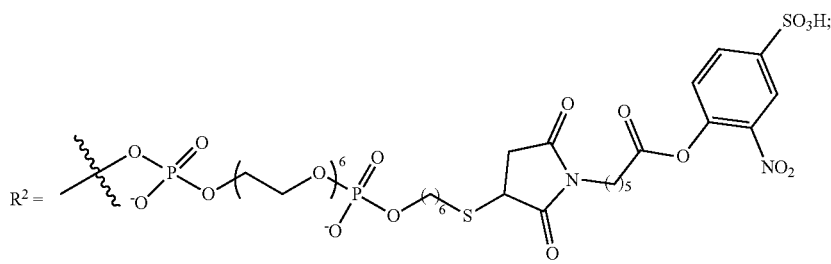
wherein:
R² has the following structure:
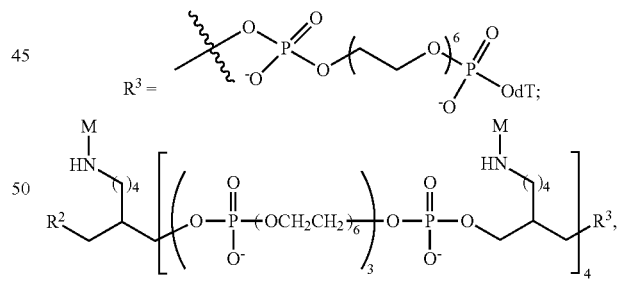
and
R³ has the following structure:
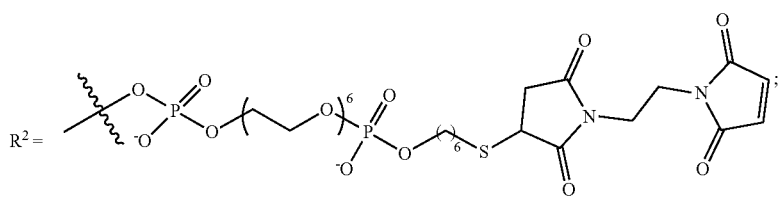
wherein:
R² has the following structure:

and
R³ has the following structure:
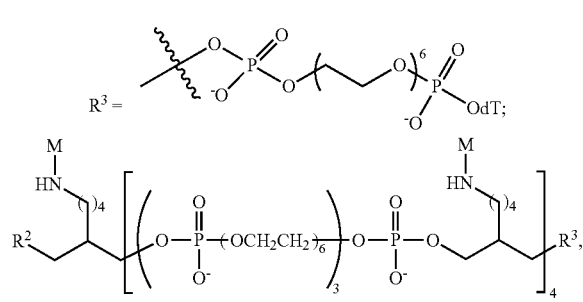
wherein:
R² has the following structure:
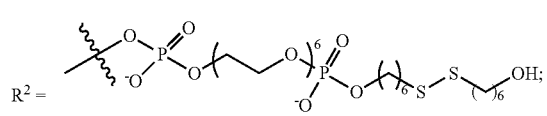
and
R³ has the following structure:
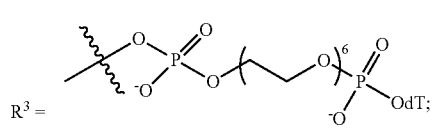
-continued
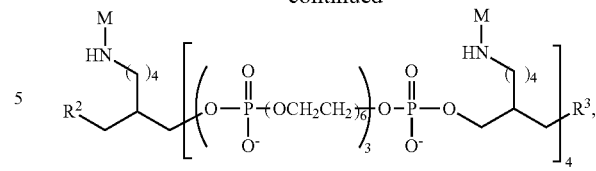
wherein:
R² has the following structure:
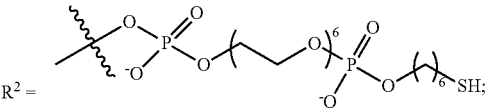
and
R³ has the following structure:
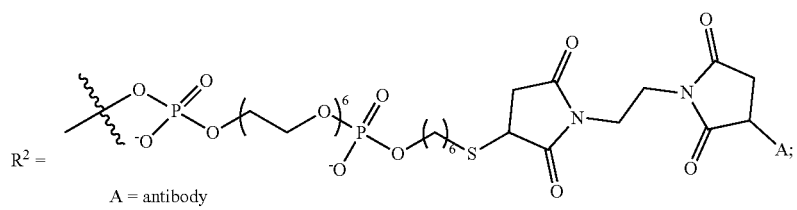
wherein:
R² has the following structure:
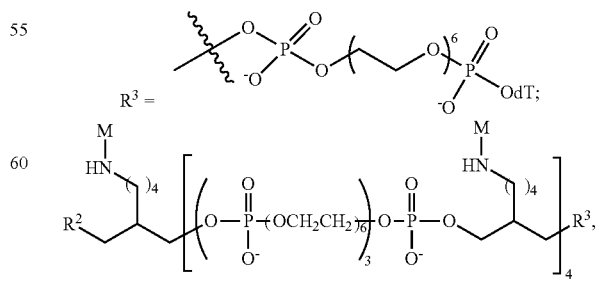
and
R³ has the following structure:

wherein:
R² has the following structure:
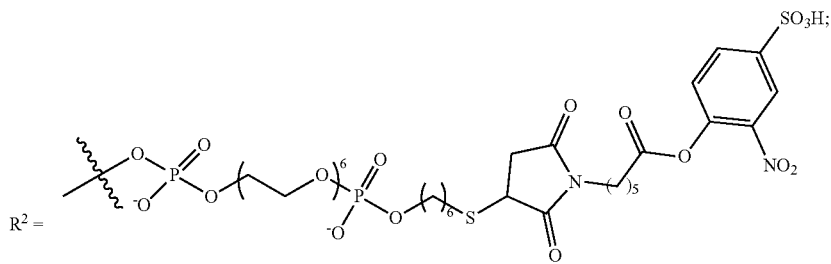
and
R³ has the following structure:
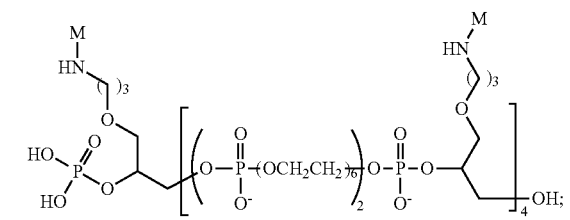
wherein R² or R³ has the following structure:
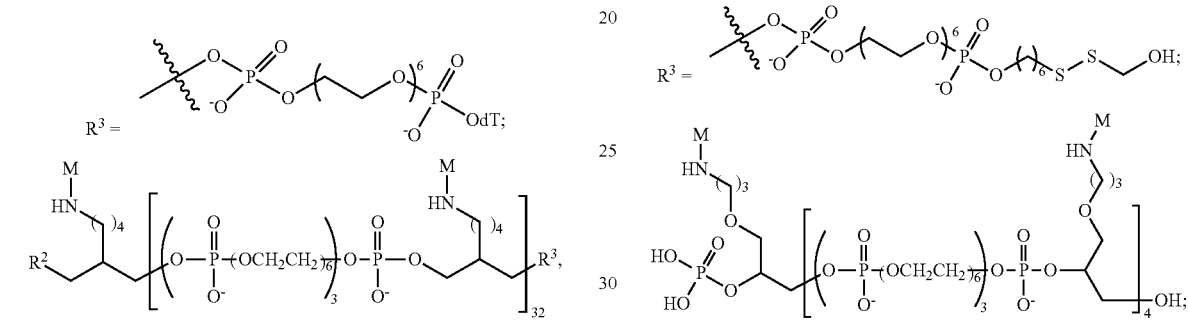
wherein R³ has the following structure:
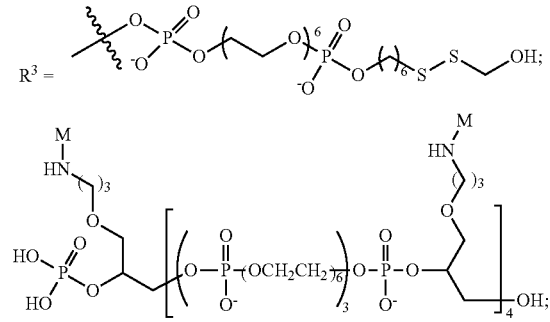
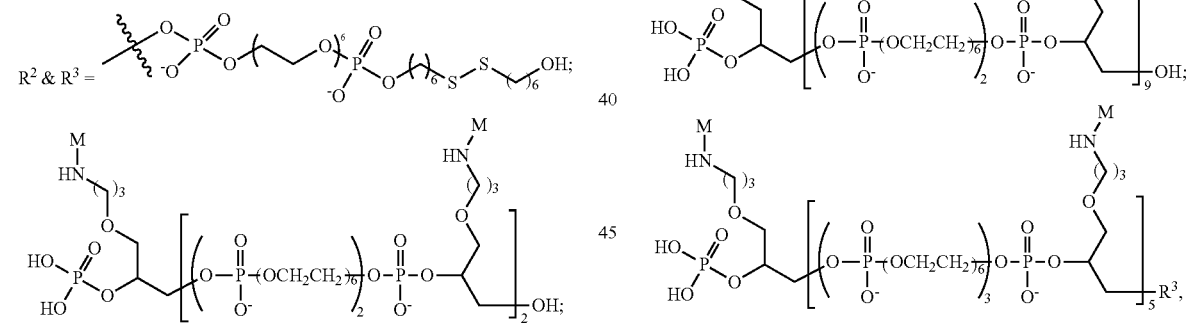
wherein R³ has the following structure:
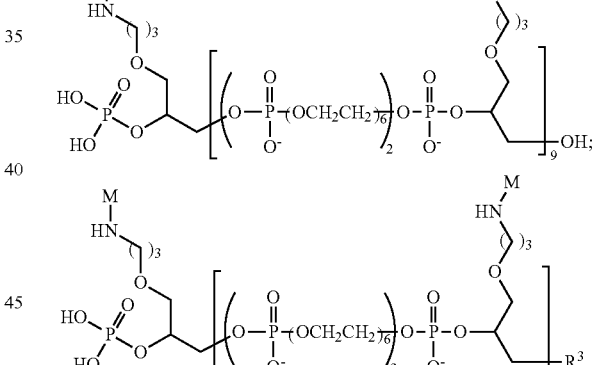

201
wherein:
R² has the following structure:
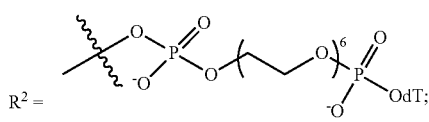
and
R³ has the following structure:
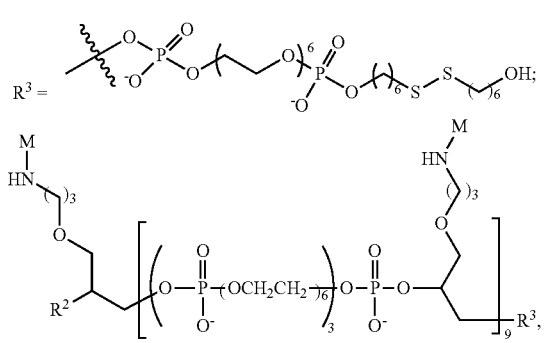
202
wherein:
R² has the following structure:
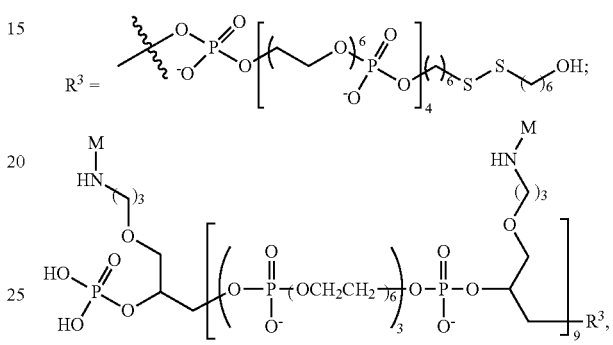
and
R³ has the following structure:
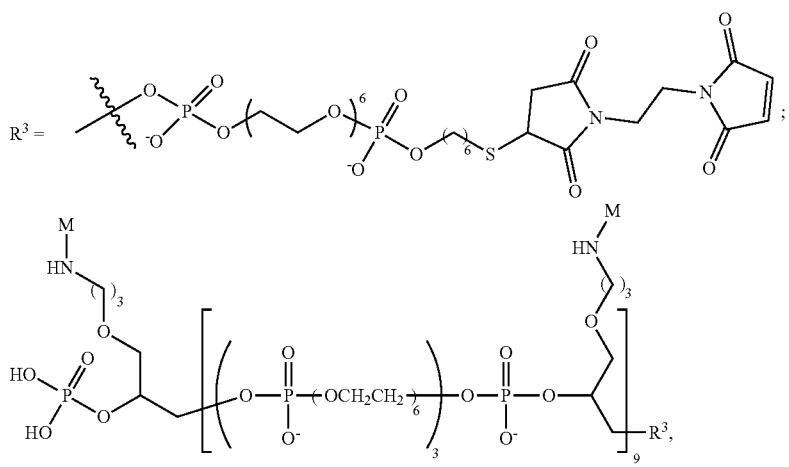
wherein R³ has the following structure:
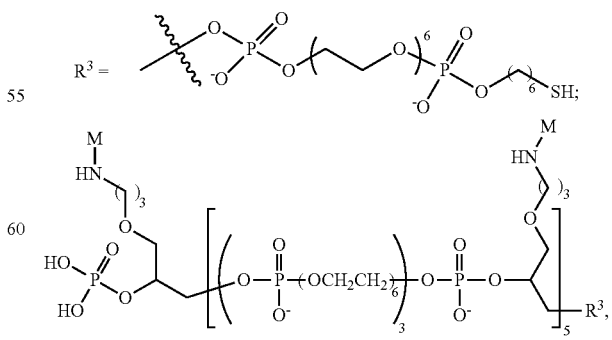

wherein R³ has the following structure:
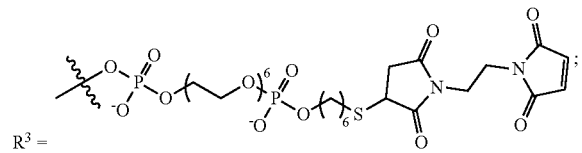
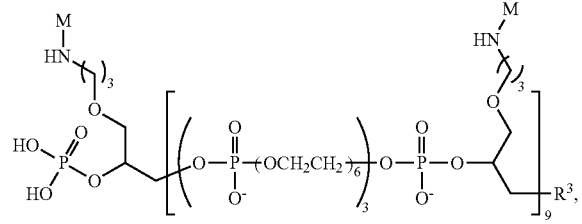
wherein R³ has the following structure:
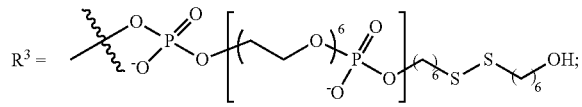
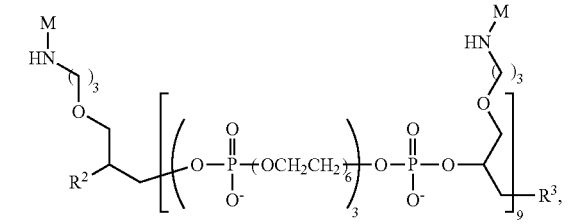
wherein:
R² has the following structure:
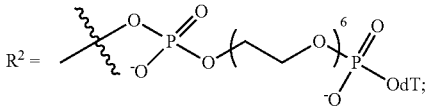
and
R³ has the following structure:
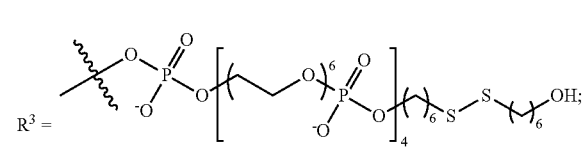
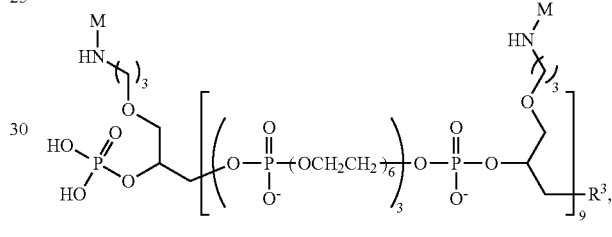
wherein R³ has the following structure:
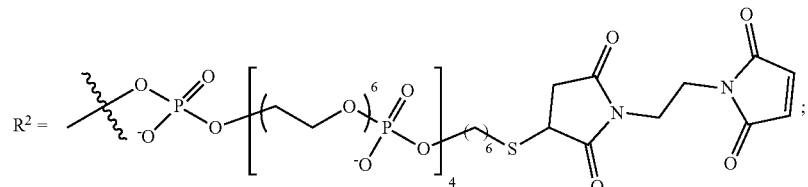
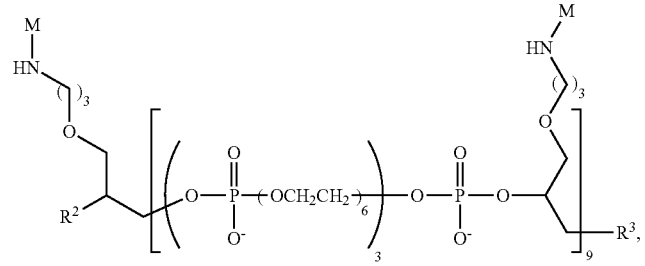
wherein:
R² has the following structure:
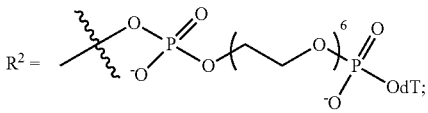

and
R³ has the following structure:
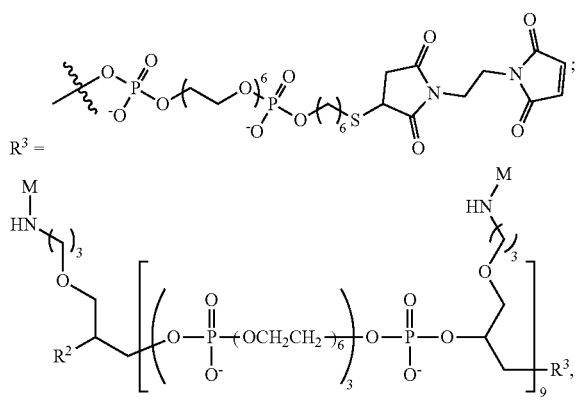
wherein:
R² has the following structure:
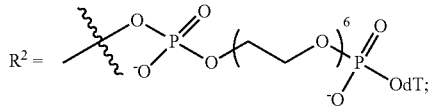
and
R³ has the following structure:
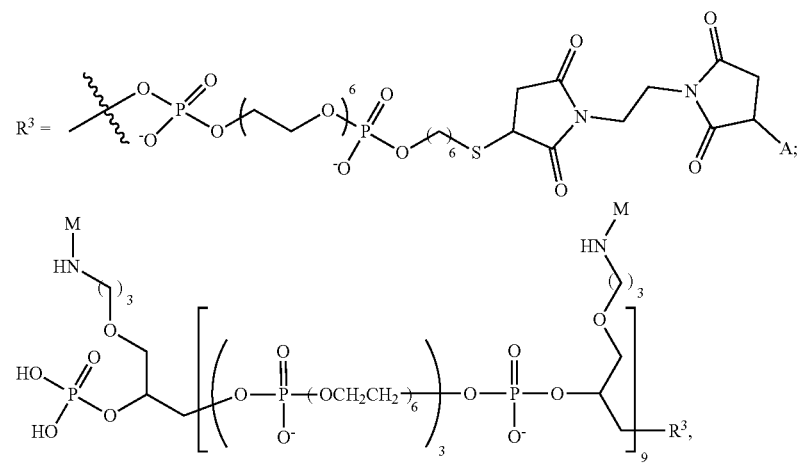
wherein R³ has the following structure:
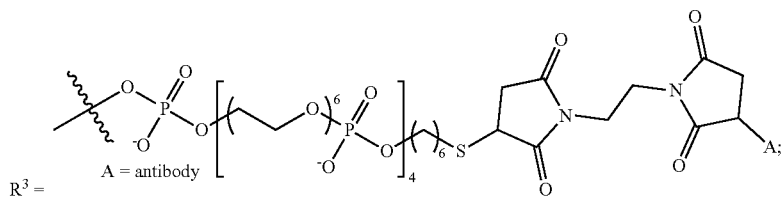
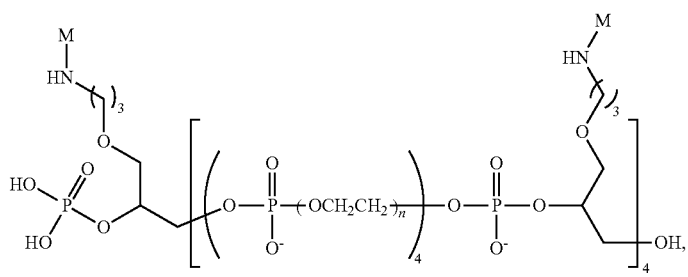

wherein n is 23;
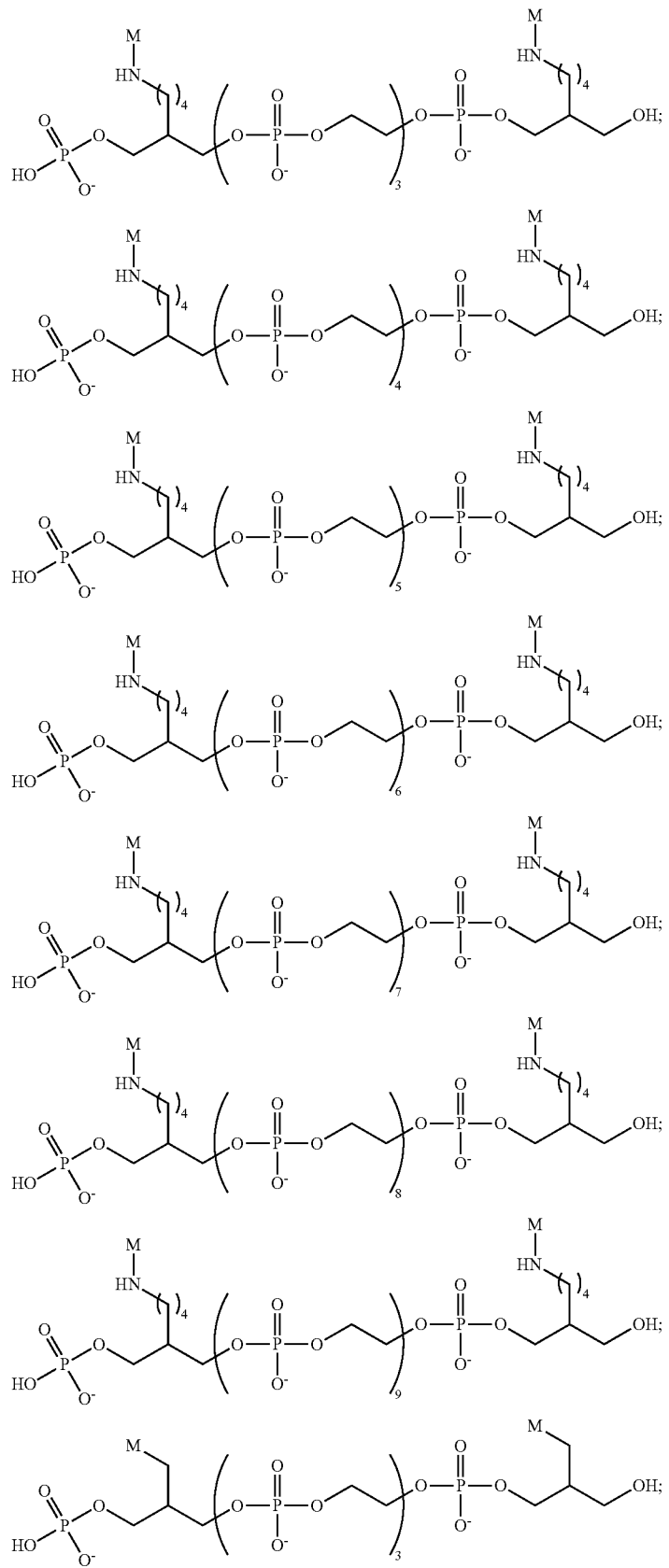

-continued
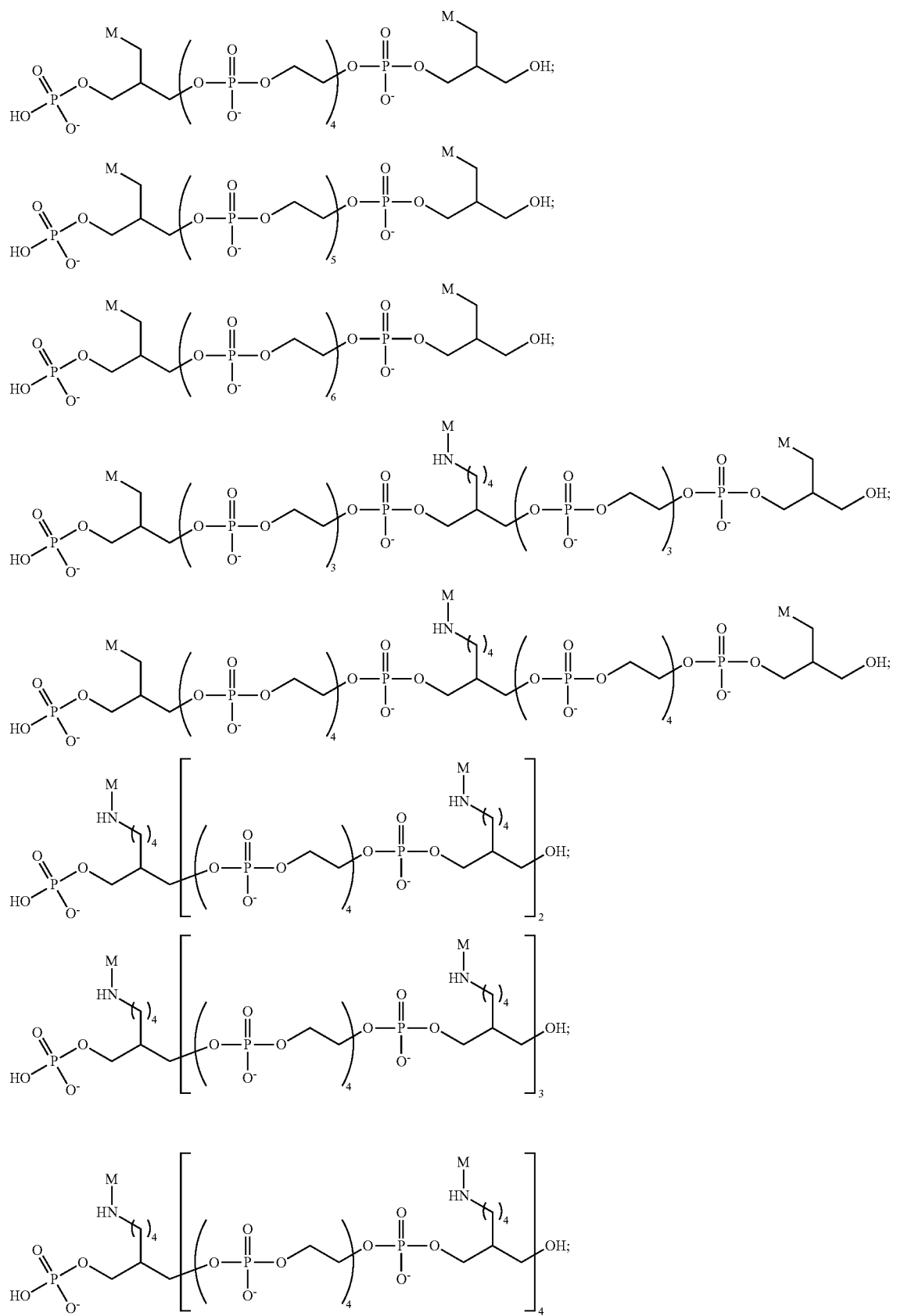

-continued
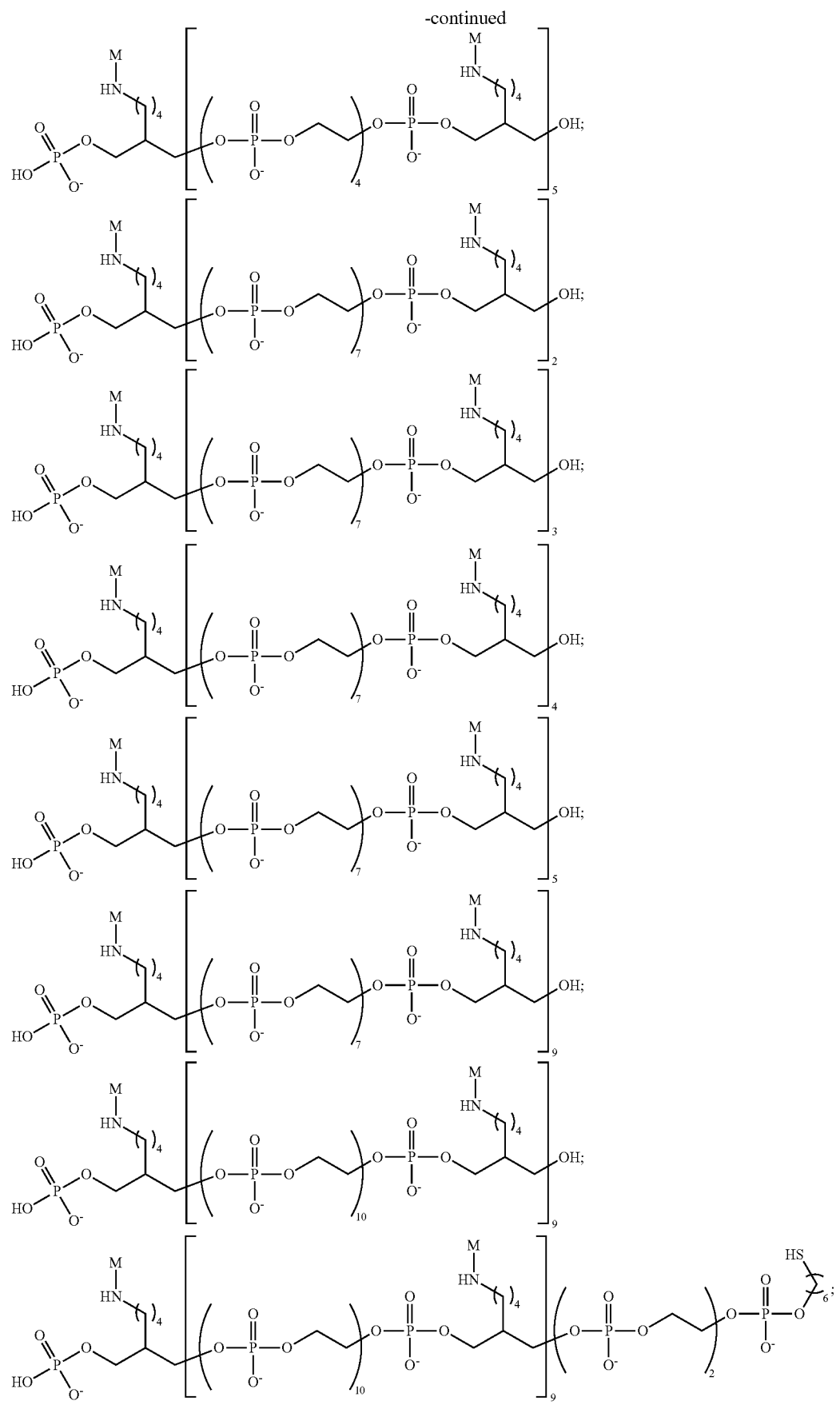

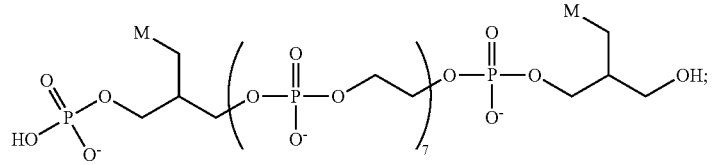
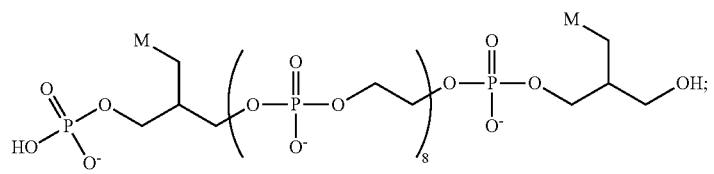
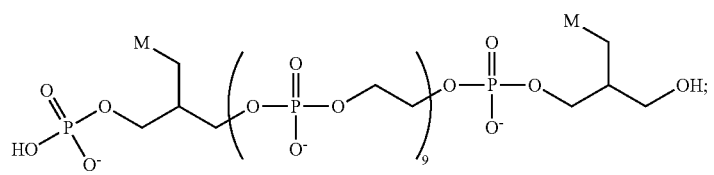
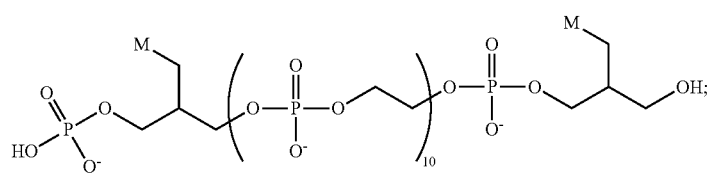
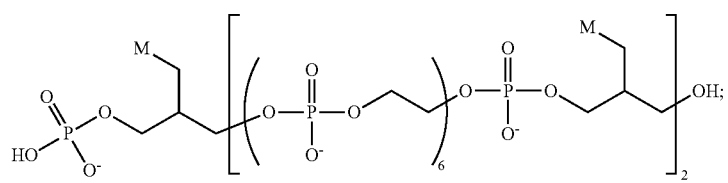
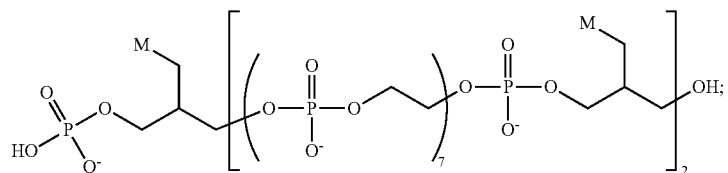
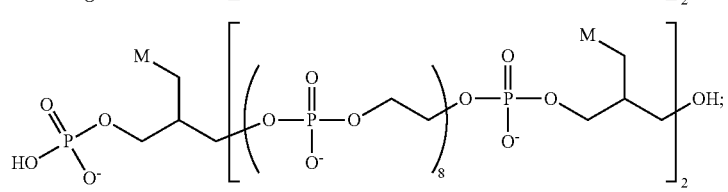
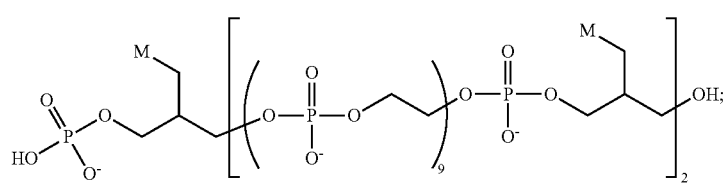
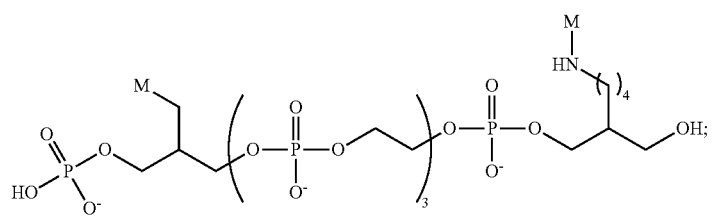

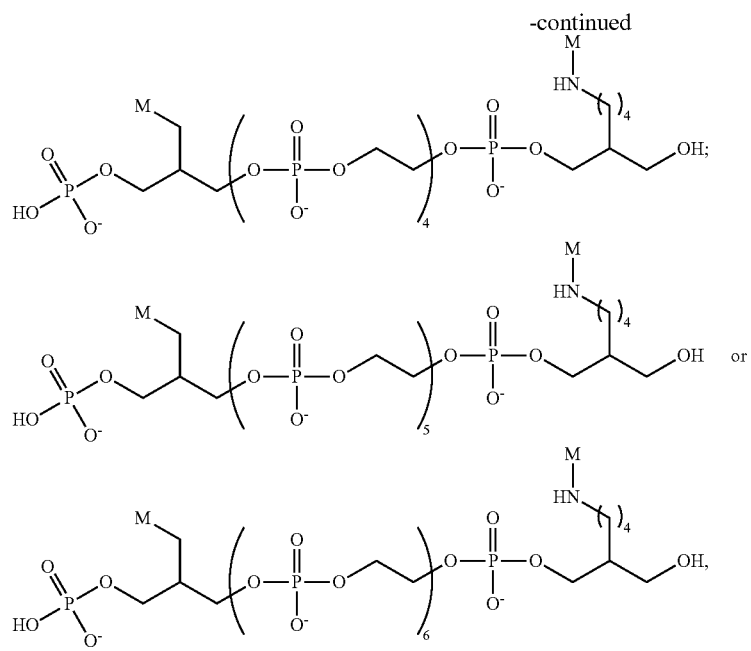
wherein:
A is an antibody;
F, F' and F" have the following structures:
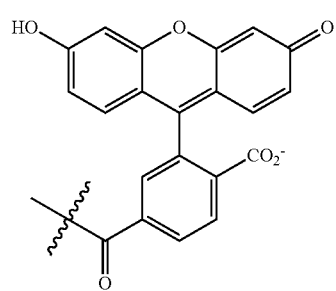
F
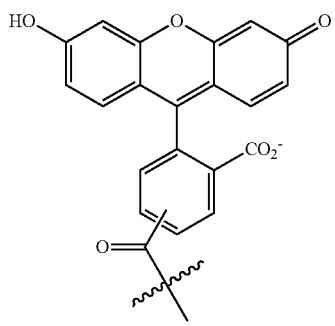
F'
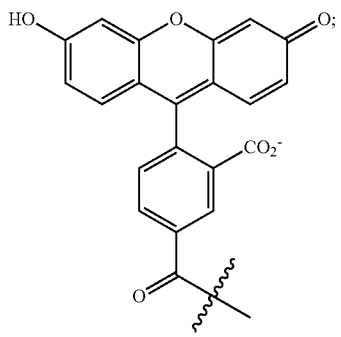
F"
N' has the following structure:
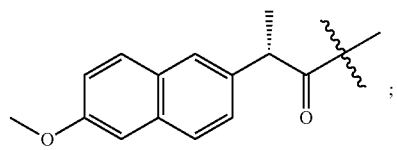
(S)-3-(6-methoxynaphthalen-2-yl)butan-2-one
I' has the following structure:
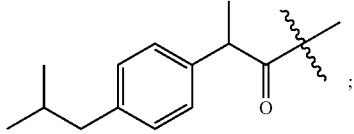 [SMILES: *C(=O)C(C)c1ccc(CC(C)C)cc1]

D' has the following structure:

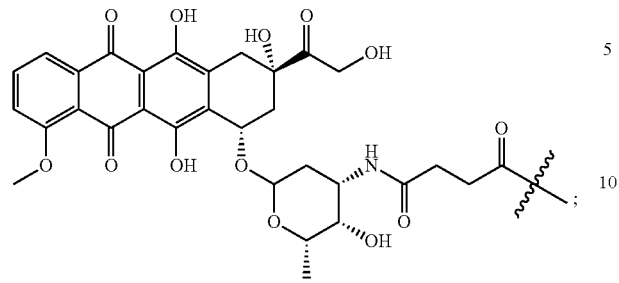

D" has the following structure:

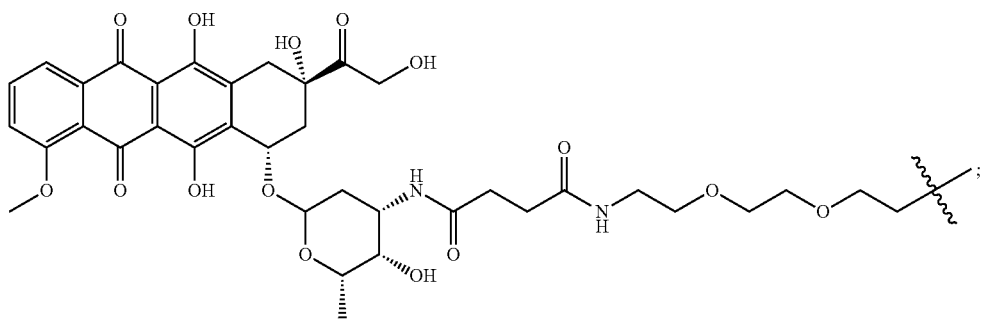 [SMILES: *CCOCCOCCNC(=O)CCC(=O)N[C@H]1CC(O[C@H]2C[C@](O)(C(=O)CO)Cc3c(O)c4c(c(O)c32)C(=O)c2c(OC)cccc2C4=O)O[C@@H](C)[C@H]1O]

AF has the following structure:

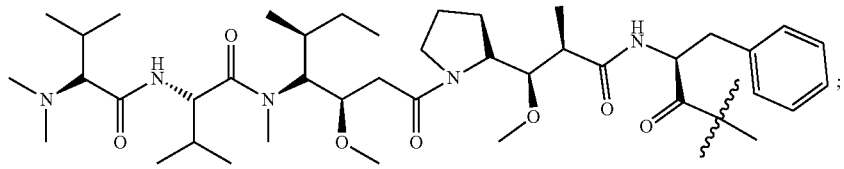

and
dT has the following structure:

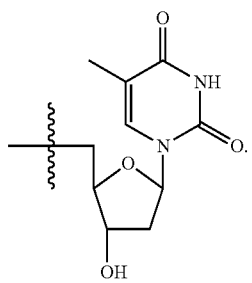

18. A composition comprising the compound of claim 1 and a pharmaceutically acceptable carrier.

19. A composition comprising a plurality of conjugates, each of the plurality of conjugates comprising a compound of claim 1, wherein one of $R^2$ and $R^3$ is —OP(=$R_a$)($R_b$)OL' or L', and L' is an antibody or a linker comprising a covalent bond to the antibody, the antibody covalently bound to two or more biologically active moieties via a single linkage, wherein the single linkage is a linkage to a polymer backbone of the compound of claim 1, the polymer backbone comprising the two or more biologically active moieties covalently bound thereto.

20. A method of treating a cancer, the method comprising administering to a subject in need thereof a therapeutically effective amount of a compound of claim 1, wherein each M is independently an anti-cancer drug effective for treating the cancer.

* * * * *

UNITED STATES PATENT AND TRADEMARK OFFICE
CERTIFICATE OF CORRECTION

PATENT NO. : 12,145,956 B2
APPLICATION NO. : 16/639496
DATED : November 19, 2024
INVENTOR(S) : Tracy Matray et al.

Page 1 of 4

It is certified that error appears in the above-identified patent and that said Letters Patent is hereby corrected as shown below:

In the Claims

Column 170, Claim 11, Line 18:
The wording: "$R^c$ is H, an electron pair or a counter ion; and"
Should read:
--$R^e$ is H, an electron pair or a counter ion; and--.

Column 173, Claim 17, the last structure, below Line 50:

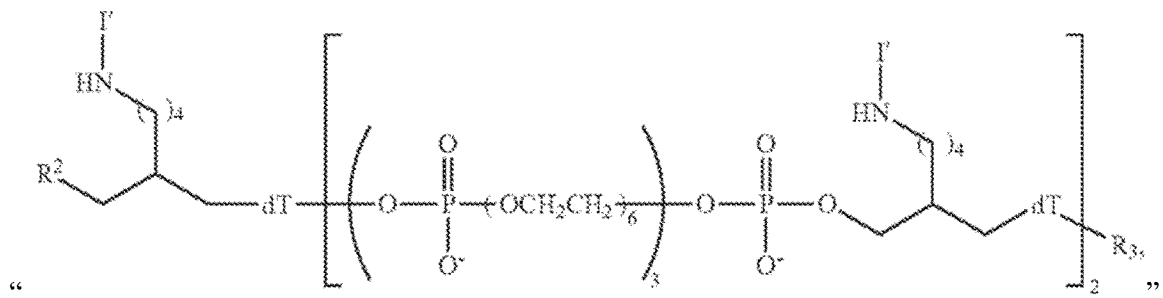
"
Should read:
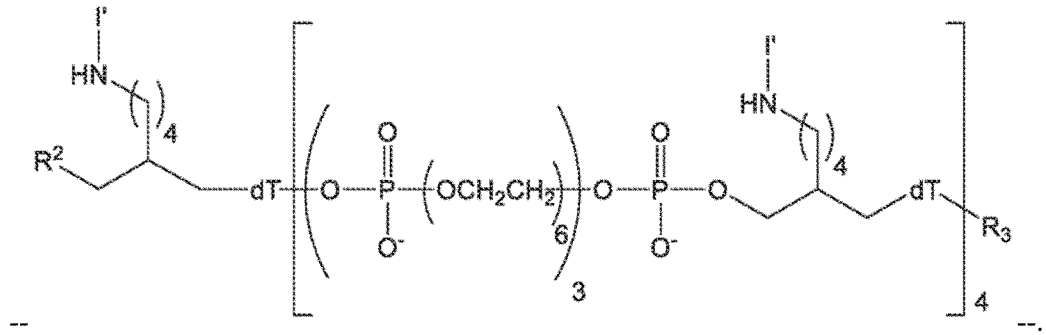
--                                                                 --.

Signed and Sealed this
Twenty-fifth Day of March, 2025

Coke Morgan Stewart
*Acting Director of the United States Patent and Trademark Office*

CERTIFICATE OF CORRECTION (continued)
U.S. Pat. No. 12,145,956 B2

Column 175, Claim 17, the structure between Lines 30 and 50:

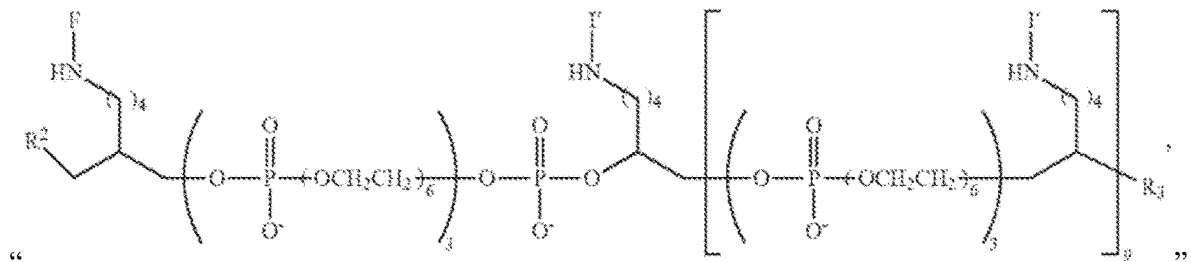

"

Should read:

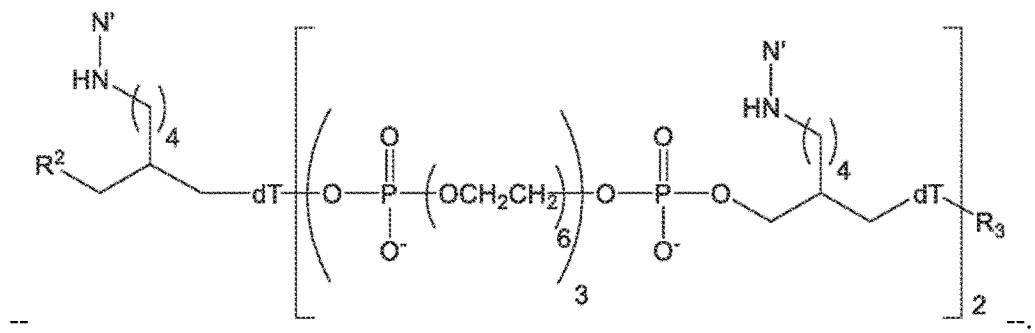

--.

Column 181, Claim 17, the last structure:

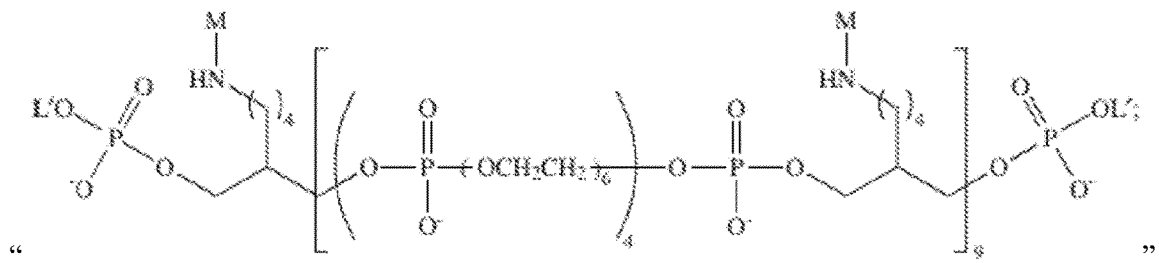

"                                                                 "

Should read:

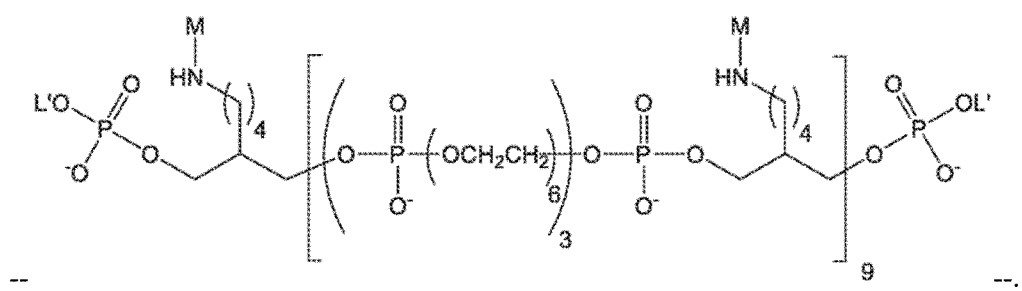

--.

CERTIFICATE OF CORRECTION (continued)
U.S. Pat. No. 12,145,956 B2

Column 185, Claim 17, the structure between Lines 40 and 45:

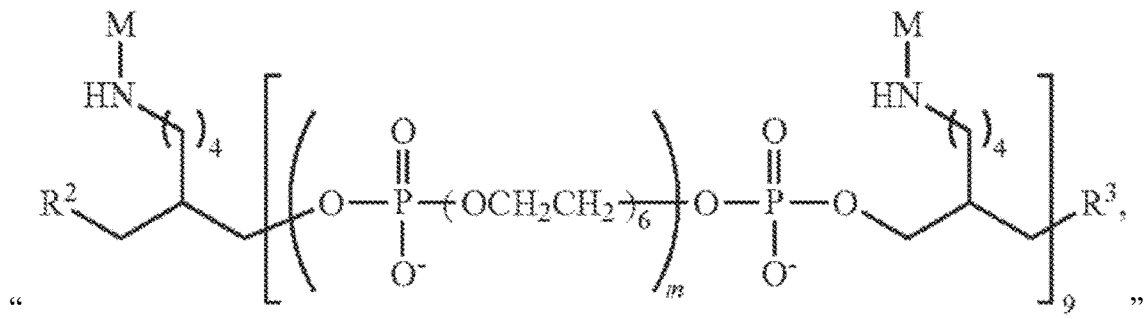
"

Should read:

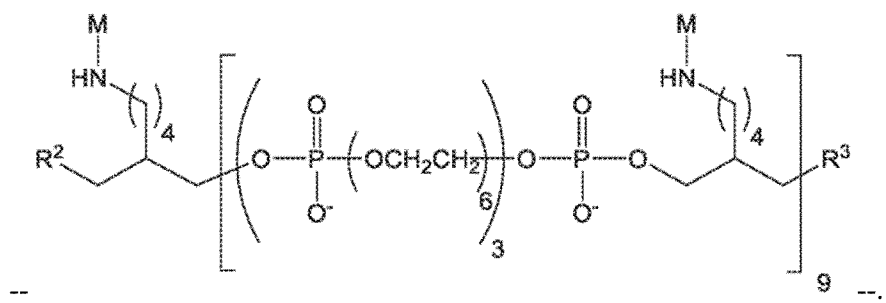
--.

Column 200, Claim 17, the structure at Line 20:

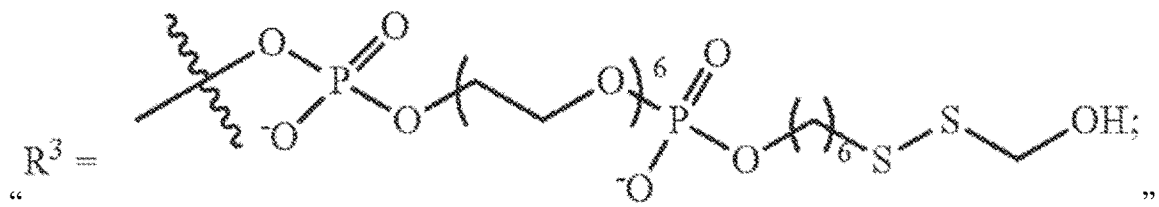
"

Should read:

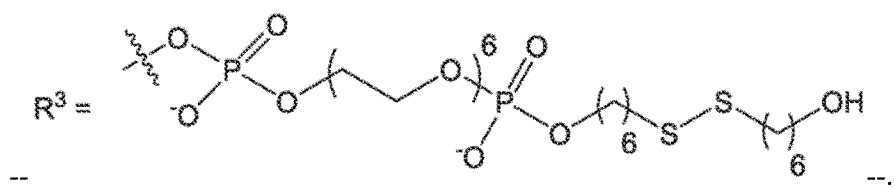
--.

Column 204, Claim 17, after Line 30:
"wherein $R^3$ has the following structure:

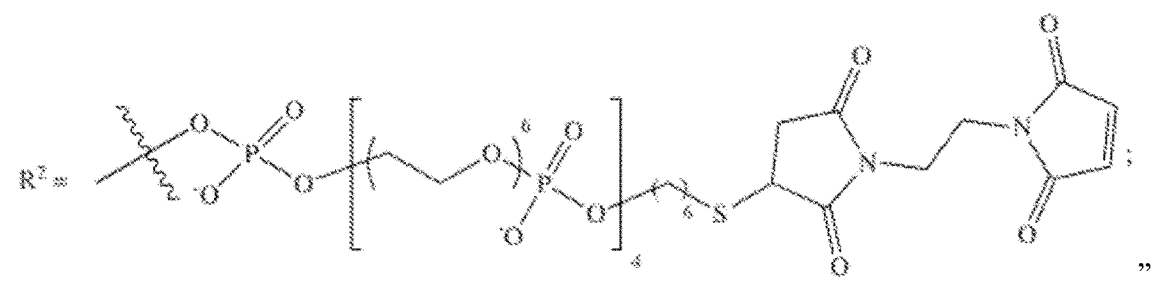
"

Should read:
--wherein R³ has the following structure:
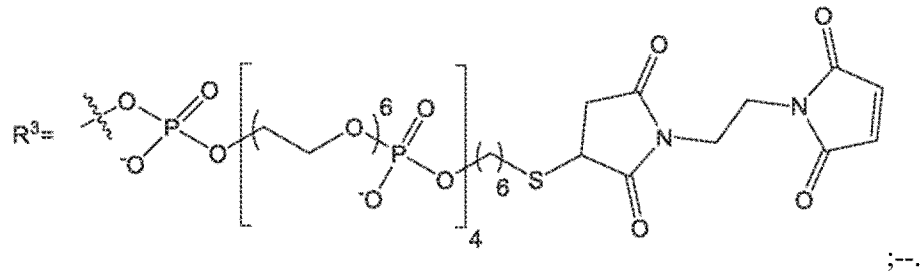
;--.